US012805922B2

(12) United States Patent
Neal, II et al.

(10) Patent No.: US 12,805,922 B2
(45) Date of Patent: Nov. 24, 2026

(54) SYSTEM AND METHOD FOR ABLATING A TISSUE SITE BY ELECTROPORATION WITH REAL-TIME MONITORING OF TREATMENT PROGRESS

(71) Applicants: Virginia Tech Intellectual Properties Inc., Blacksburg, VA (US); AngioDynamics, Inc., Latham, NY (US)

(72) Inventors: Robert Neal, II, Richmond, VA (US); Rafael V. Davalos, Aptos, CA (US)

(73) Assignees: Virginia Tech Intellectual Properties, Inc., Blacksburg, VA (US); AngioDynamics, Inc., Latham, NY (US)

( * ) Notice: Subject to any disclaimer, the term of this patent is extended or adjusted under 35 U.S.C. 154(b) by 167 days.

(21) Appl. No.: 18/528,051

(22) Filed: Dec. 4, 2023

(65) Prior Publication Data

US 2024/0173063 A1 May 30, 2024

Related U.S. Application Data

(63) Continuation of application No. 17/338,960, filed on Jun. 4, 2021, now Pat. No. 11,890,046, which is a (Continued)

(51) Int. Cl.
*A61B 18/12* (2006.01)
*A61B 18/14* (2006.01)
(Continued)

(52) U.S. Cl.
CPC .......... *A61B 18/1206* (2013.01); *A61B 18/14* (2013.01); *A61B 18/1477* (2013.01); (Continued)

(58) Field of Classification Search
CPC . A61B 18/1206; A61B 18/14; A61B 18/1477; A61B 18/16; A61B 18/18;
(Continued)

(56) References Cited

U.S. PATENT DOCUMENTS

| | | | |
|---|---|---|---|
| 1,653,819 | A | 12/1927 | Northcott |
| 3,730,238 | A | 5/1973 | Butler |

(Continued)

FOREIGN PATENT DOCUMENTS

| | | | |
|---|---|---|---|
| AU | 7656800 | A | 4/2001 |
| AU | 2002315095 | A1 | 12/2002 |

(Continued)

OTHER PUBLICATIONS

Valdez, C. M. et al., "The interphase interval within a bipolar nanosecond electric pulse modulates bipolar cancellation," Bioelectromagnetics, vol. 39, No. 6, 441-450, 2018, 28 pages.

(Continued)

*Primary Examiner* — Michael F Peffley
(74) *Attorney, Agent, or Firm* — New River Valley IP Law, P.C.; Michele L. Mayberry; Ashley M. Gates

(57) ABSTRACT

A medical system for ablating a tissue site with real-time monitoring during an electroporation treatment procedure. A pulse generator generates a pre-treatment (PT) test signal prior to the treatment procedure and intra-treatment (IT) test signals during the treatment procedure. A treatment control module determines impedance values from the PT test signal and IT test signals and determines a progress of electroporation and an end point of treatment in real-time based on the determined impedance values while the treatment progresses.

8 Claims, 8 Drawing Sheets

Related U.S. Application Data continuation of application No. 16/280,511, filed on Feb. 20, 2019, now abandoned, which is a continuation of application No. 14/940,863, filed on Nov. 13, 2015, now Pat. No. 10,238,447, which is a continuation-in-part of application No. 14/012,832, filed on Aug. 28, 2013, now Pat. No. 9,283,051, which is a continuation-in-part of application No. 12/491,151, filed on Jun. 24, 2009, now Pat. No. 8,992,517, which is a continuation-in-part of application No. 12/432,295, filed on Apr. 29, 2009, now Pat. No. 9,598,691.

(60) Provisional application No. 62/173,538, filed on Jun. 10, 2015, provisional application No. 62/079,061, filed on Nov. 13, 2014, provisional application No. 61/171,564, filed on Apr. 22, 2009, provisional application No. 61/167,997, filed on Apr. 9, 2009, provisional application No. 61/075,216, filed on Jun. 24, 2008, provisional application No. 61/125,840, filed on Apr. 29, 2008.

(51) Int. Cl.
*A61B 18/18* (2006.01)
*A61B 34/10* (2016.01)
*C12N 13/00* (2006.01)
*A61B 18/00* (2006.01)

(52) U.S. Cl.
CPC .............. *A61B 18/18* (2013.01); *A61B 34/10* (2016.02); *C12N 13/00* (2013.01); *A61B 2018/0016* (2013.01); *A61B 2018/00577* (2013.01); *A61B 2018/00613* (2013.01); *A61B 2018/00666* (2013.01); *A61B 2018/00672* (2013.01); *A61B 2018/00678* (2013.01); *A61B 2018/00767* (2013.01); *A61B 2018/00875* (2013.01); *A61B 2018/1425* (2013.01); *A61B 2034/104* (2016.02)

(58) Field of Classification Search
CPC .. A61B 2018/0016; A61B 2018/00577; A61B 2018/00613; A61B 2018/00666; A61B 2018/00672; A61B 2018/00678; A61B 2018/00708; A61B 2018/00761; A61B 2018/00767; A61B 2018/00875; A61B 2018/124; A61B 2018/1425; A61B 2034/104; A61B 34/10; C12N 13/00
See application file for complete search history.

(56) References Cited

U.S. PATENT DOCUMENTS 3,746,004 A 7/1973 Jankelson
3,871,359 A 3/1975 Pacela
4,016,886 A 4/1977 Doss et al.
4,037,341 A 7/1977 Odle et al.
4,216,860 A 8/1980 Heimann
4,226,246 A 10/1980 Fragnet
4,262,672 A 4/1981 Kief
4,267,047 A 5/1981 Henne et al.
4,278,092 A 7/1981 Borsanyi et al.
4,299,217 A 11/1981 Sagae et al.
4,311,148 A 1/1982 Courtney et al.
4,336,881 A 6/1982 Babb et al.
4,344,436 A 8/1982 Kubota
4,392,855 A 7/1983 Oreopoulos et al.
4,406,827 A 9/1983 Carim
4,407,943 A 10/1983 Cole et al.
4,416,276 A 11/1983 Newton et al.
4,447,235 A 5/1984 Clarke
4,469,098 A 9/1984 Davi
4,489,535 A 12/1984 Veltman
4,512,765 A 4/1985 Muto
4,580,572 A 4/1986 Granek et al.
4,636,199 A 1/1987 Victor
4,672,969 A 6/1987 Dew
4,676,258 A 6/1987 Inokuchi et al.
4,676,782 A 6/1987 Yamamoto et al.
4,687,471 A 8/1987 Twardowski et al.
4,716,896 A 1/1988 Ackerman
4,723,549 A 2/1988 Wholey et al.
D294,519 S 3/1988 Hardy
4,756,838 A 7/1988 Veltman
4,772,269 A 9/1988 Twardowski et al.
4,798,585 A 1/1989 Inoue et al.
4,810,963 A 3/1989 Blake-Coleman et al.
4,813,929 A 3/1989 Semrad
4,819,637 A 4/1989 Dormandy et al.
4,822,470 A 4/1989 Chang
4,836,204 A 6/1989 Landymore et al.
4,840,172 A 6/1989 Augustine et al.
4,863,426 A 9/1989 Ferragamo et al.
4,885,003 A 12/1989 Hillstead
4,886,496 A 12/1989 Conoscenti et al.
4,886,502 A 12/1989 Poirier et al.
4,889,634 A 12/1989 El-Rashidy
4,903,707 A 2/1990 Knute et al.
4,907,601 A 3/1990 Frick
4,919,148 A 4/1990 Muccio
4,920,978 A 5/1990 Colvin
4,921,484 A 5/1990 Hillstead
4,946,793 A 8/1990 Marshall, III
4,976,709 A 12/1990 Sand
4,981,477 A 1/1991 Schon et al.
4,986,810 A 1/1991 Semrad
4,987,895 A 1/1991 Heimlich
5,019,034 A 5/1991 Weaver et al.
5,031,775 A 7/1991 Kane
5,052,391 A 10/1991 Silberstone et al.
5,053,013 A 10/1991 Ensminger et al.
5,058,605 A 10/1991 Slovak
5,071,558 A 12/1991 Itoh
5,098,843 A 3/1992 Calvin
5,122,137 A 6/1992 Lennox
5,134,070 A 7/1992 Casnig
5,137,517 A 8/1992 Loney et al.
5,141,499 A 8/1992 Zappacosta
D329,496 S 9/1992 Wotton
5,156,597 A 10/1992 Verreet et al.
5,173,158 A 12/1992 Schmukler
5,186,715 A 2/1993 Phillips et al.
5,186,800 A 2/1993 Dower
5,188,592 A 2/1993 Hakki
5,190,541 A 3/1993 Abele et al.
5,192,312 A 3/1993 Orton
5,193,537 A 3/1993 Freeman
5,209,723 A 5/1993 Twardowski et al.
5,215,530 A 6/1993 Hogan
5,224,933 A 7/1993 Bromander
5,227,730 A 7/1993 King et al.
5,242,415 A 9/1993 Kantrowitz et al.
5,273,525 A 12/1993 Hofmann
D343,687 S 1/1994 Houghton et al.
5,277,201 A 1/1994 Stern
5,279,564 A 1/1994 Taylor
5,281,213 A 1/1994 Milder
5,283,194 A 2/1994 Schmukler
5,290,263 A 3/1994 Wigness et al.
5,308,325 A 5/1994 Quinn et al.
5,308,338 A 5/1994 Helfrich
5,318,543 A 6/1994 Ross et al.
5,318,563 A 6/1994 Malis et al.
5,328,451 A 7/1994 Davis et al.
5,334,167 A 8/1994 Cocanower
5,348,554 A 9/1994 Imran et al.
D351,661 S 10/1994 Fischer
5,383,917 A 1/1995 Desai et al.
5,389,069 A 2/1995 Weaver
5,391,158 A 2/1995 Peters
5,403,311 A 4/1995 Abele et al.

(56) References Cited

U.S. PATENT DOCUMENTS 5,405,320 A 4/1995 Twardowski et al.
5,425,752 A 6/1995 Nguyen
5,439,440 A 8/1995 Hofmann
5,458,625 A 10/1995 Kendall
5,484,400 A 1/1996 Edwards et al.
5,484,401 A 1/1996 Rodriguez et al.
5,533,999 A 7/1996 Hood et al.
5,536,240 A 7/1996 Edwards et al.
5,536,267 A 7/1996 Edwards et al.
5,540,737 A 7/1996 Fenn
5,546,940 A 8/1996 Panescu et al.
5,562,720 A 10/1996 Stern et al.
5,575,811 A 11/1996 Reid et al.
D376,652 S 12/1996 Hunt et al.
5,582,588 A 12/1996 Sakurai et al.
5,586,982 A 12/1996 Abela
5,588,424 A 12/1996 Insler et al.
5,588,960 A 12/1996 Edwards et al.
5,599,294 A 2/1997 Edwards et al.
5,599,311 A 2/1997 Raulerson
5,616,126 A 4/1997 Malekmehr et al.
5,620,479 A 4/1997 Diederich
5,626,146 A 5/1997 Barber et al.
D380,272 S 6/1997 Partika et al.
5,634,899 A 6/1997 Shapland et al.
5,643,197 A 7/1997 Brucker et al.
5,645,855 A 7/1997 Lorenz
5,672,173 A 9/1997 Gough et al.
5,674,267 A 10/1997 Mir et al.
5,683,384 A 11/1997 Gough et al.
5,687,723 A 11/1997 Avitall
5,690,620 A 11/1997 Knott
5,697,905 A 12/1997 d'Ambrosio
5,700,252 A 12/1997 Klingenstein
5,702,359 A 12/1997 Hofmann et al.
5,718,246 A 2/1998 Vona
5,720,921 A 2/1998 Meserol
5,735,847 A 4/1998 Gough et al.
5,752,939 A 5/1998 Makoto
5,778,894 A 7/1998 Dorogi et al.
5,782,882 A 7/1998 Lerman et al.
5,800,378 A 9/1998 Edwards et al.
5,800,484 A 9/1998 Gough et al.
5,807,272 A 9/1998 Kun et al.
5,807,306 A 9/1998 Shapland et al.
5,807,395 A 9/1998 Mulier et al.
5,810,742 A 9/1998 Pearlman
5,810,762 A 9/1998 Hofmann
5,830,184 A 11/1998 Basta
5,836,897 A 11/1998 Sakurai et al.
5,836,905 A 11/1998 Lemelson et al.
5,843,026 A 12/1998 Edwards et al.
5,843,182 A 12/1998 Goldstein
5,865,787 A 2/1999 Shapland et al.
5,868,708 A 2/1999 Hart et al.
5,873,849 A 2/1999 Bernard
5,904,648 A 5/1999 Arndt et al.
5,919,142 A 7/1999 Boone et al.
5,919,191 A 7/1999 Lennox et al.
5,921,982 A 7/1999 Lesh et al.
5,944,710 A 8/1999 Dev et al.
5,947,284 A 9/1999 Foster
5,947,889 A 9/1999 Hehrlein
5,951,546 A 9/1999 Lorentzen
5,954,745 A 9/1999 Gertler et al.
5,957,919 A 9/1999 Laufer
5,957,963 A 9/1999 Dobak, III
5,968,006 A 10/1999 Hofmann
5,983,131 A 11/1999 Weaver et al.
5,984,896 A 11/1999 Boyd
5,991,697 A 11/1999 Nelson et al.
5,999,847 A 12/1999 Elstrom
6,004,339 A 12/1999 Wijay
6,009,347 A 12/1999 Hofmann
6,009,877 A 1/2000 Edwards
6,010,613 A 1/2000 Walters et al.
6,016,452 A 1/2000 Kasevich
6,029,090 A 2/2000 Herbst
6,041,252 A 3/2000 Walker et al.
6,043,066 A 3/2000 Mangano et al.
6,050,994 A 4/2000 Sherman
6,055,453 A 4/2000 Hofmann et al.
6,059,780 A 5/2000 Gough et al.
6,066,134 A 5/2000 Eggers et al.
6,068,121 A 5/2000 McGlinch
6,068,650 A 5/2000 Hofmann et al.
6,071,281 A 6/2000 Burnside et al.
6,074,374 A 6/2000 Fulton
6,074,389 A 6/2000 Levine et al.
6,085,115 A 7/2000 Weaver et al.
6,090,016 A 7/2000 Kuo
6,090,105 A 7/2000 Zepeda et al.
6,090,106 A 7/2000 Goble et al.
D430,015 S 8/2000 Himbert et al.
6,096,035 A 8/2000 Sodhi et al.
6,102,885 A 8/2000 Bass
6,106,521 A 8/2000 Blewett et al.
6,109,270 A 8/2000 Mah et al.
6,110,192 A 8/2000 Ravenscroft et al.
6,113,593 A 9/2000 Tu et al.
6,116,330 A 9/2000 Salyer
6,120,493 A 9/2000 Hofmann
6,122,599 A 9/2000 Mehta
6,123,701 A 9/2000 Nezhat
6,132,397 A 10/2000 Davis et al.
6,132,419 A 10/2000 Hofmann
6,134,460 A 10/2000 Chance
6,135,999 A 10/2000 Fanton et al.
6,139,545 A 10/2000 Utley et al.
6,150,148 A 11/2000 Nanda et al.
6,159,163 A 12/2000 Strauss et al.
6,178,354 B1 1/2001 Gibson
D437,941 S 2/2001 Frattini
6,193,715 B1 2/2001 Wrublewski et al.
6,198,970 B1 3/2001 Freed et al.
6,200,314 B1 3/2001 Sherman
6,208,893 B1 3/2001 Hofmann
6,210,402 B1 4/2001 Olsen et al.
6,212,433 B1 4/2001 Behl
6,216,034 B1 4/2001 Hofmann et al.
6,219,577 B1 4/2001 Brown, III et al.
D442,697 S 5/2001 Hajianpour
6,233,490 B1 5/2001 Kasevich
6,235,023 B1 5/2001 Lee et al.
D443,360 S 6/2001 Haberland
6,241,702 B1 6/2001 Lundquist et al.
6,241,725 B1 6/2001 Cosman
D445,198 S 7/2001 Frattini
6,258,100 B1 7/2001 Alferness et al.
6,261,831 B1 7/2001 Agee
6,277,114 B1 8/2001 Bullivant et al.
6,278,895 B1 8/2001 Bernard
6,280,441 B1 8/2001 Ryan
6,283,988 B1 9/2001 Laufer et al.
6,283,989 B1 9/2001 Laufer et al.
6,284,140 B1 9/2001 Sommermeyer et al.
6,287,293 B1 9/2001 Jones et al.
6,287,304 B1 9/2001 Eggers et al.
6,296,636 B1 10/2001 Cheng et al.
6,298,726 B1 10/2001 Adachi et al.
6,299,633 B1 10/2001 Laufer
6,300,108 B1 10/2001 Rubinsky et al.
D450,391 S 11/2001 Hunt et al.
6,312,428 B1 11/2001 Eggers et al.
6,326,177 B1 12/2001 Schoenbach et al.
6,327,505 B1 12/2001 Medhkour et al.
6,328,689 B1 12/2001 Gonzalez et al.
6,347,247 B1 2/2002 Dev et al.
6,349,233 B1 2/2002 Adams
6,351,674 B2 2/2002 Silverstone
6,375,634 B1 4/2002 Carroll
6,387,671 B1 5/2002 Rubinsky et al.
6,398,779 B1 6/2002 Buysse et al.
6,403,348 B1 6/2002 Rubinsky et al.

(56) References Cited

U.S. PATENT DOCUMENTS 6,405,732 B1 6/2002 Edwards et al.
6,411,852 B1 6/2002 Danek et al.
6,419,674 B1 7/2002 Bowser et al.
6,428,802 B1 8/2002 Atala
6,443,952 B1 9/2002 Mulier et al.
6,463,331 B1 10/2002 Edwards
6,470,211 B1 10/2002 Ideker et al.
6,478,793 B1 11/2002 Cosman et al.
6,482,221 B1 11/2002 Hebert et al.
6,482,619 B1 11/2002 Rubinsky et al.
6,485,487 B1 11/2002 Sherman
6,488,673 B1 12/2002 Laufer et al.
6,488,678 B2 12/2002 Sherman
6,488,680 B1 12/2002 Francischelli et al.
6,491,706 B1 12/2002 Alferness et al.
6,493,589 B1 12/2002 Medhkour et al.
6,493,592 B1 12/2002 Leonard et al.
6,500,173 B2 12/2002 Underwood et al.
6,503,248 B1 1/2003 Levine
6,506,189 B1 1/2003 Rittman et al.
6,514,248 B1 2/2003 Eggers et al.
6,520,183 B2 2/2003 Amar
6,526,320 B2 2/2003 Mitchell
D471,640 S 3/2003 McMichael et al.
D471,641 S 3/2003 McMichael et al.
6,530,922 B2 3/2003 Cosman et al.
6,533,784 B2 3/2003 Truckai et al.
6,537,976 B1 3/2003 Gupta
6,540,695 B1 4/2003 Burbank et al.
6,558,378 B2 5/2003 Sherman et al.
6,562,604 B2 5/2003 Rubinsky et al.
6,569,162 B2 5/2003 He
6,575,969 B1 6/2003 Rittman et al.
6,589,161 B2 7/2003 Corcoran
6,592,594 B2 7/2003 Rimbaugh et al.
6,607,529 B1 8/2003 Jones et al.
6,610,054 B1 8/2003 Edwards et al.
6,611,706 B2 8/2003 Avrahami et al.
6,613,211 B1 9/2003 Mccormick et al.
6,616,657 B2 9/2003 Simpson et al.
6,627,421 B1 9/2003 Unger et al.
D480,816 S 10/2003 McMichael et al.
6,634,363 B1 10/2003 Danek et al.
6,638,253 B2 10/2003 Breznock
6,653,091 B1 11/2003 Dunn et al.
6,666,858 B2 12/2003 Lafontaine
6,669,691 B1 12/2003 Taimisto
6,673,070 B2 1/2004 Edwards et al.
6,678,558 B1 1/2004 Dimmer et al.
6,689,096 B1 2/2004 Loubens et al.
6,692,493 B2 2/2004 Mcgovern et al.
6,694,979 B2 2/2004 Deem et al.
6,694,984 B2 2/2004 Habib
6,695,861 B1 2/2004 Rosenberg et al.
6,697,669 B2 2/2004 Dev et al.
6,697,670 B2 2/2004 Chomenky et al.
6,702,808 B1 3/2004 Kreindel
6,712,811 B2 3/2004 Underwood et al.
D489,973 S 5/2004 Root et al.
6,733,516 B2 5/2004 Simons et al.
6,753,171 B2 6/2004 Karube et al.
6,761,716 B2 7/2004 Kadhiresan et al.
D495,807 S 9/2004 Agbodoe et al.
6,795,728 B2 9/2004 Chornenky et al.
6,796,981 B2 9/2004 Wham et al.
6,801,804 B2 10/2004 Miller et al.
6,812,204 B1 11/2004 McHale et al.
6,837,886 B2 1/2005 Collins et al.
6,847,848 B2 1/2005 Sterzer et al.
6,860,847 B2 3/2005 Alferness et al.
6,865,416 B2 3/2005 Dev et al.
6,881,213 B2 4/2005 Ryan et al.
6,892,099 B2 5/2005 Jaafar et al.
6,895,267 B2 5/2005 Panescu et al.
6,905,480 B2 6/2005 McGuckin et al.
6,912,417 B1 6/2005 Bernard et al.
6,927,049 B2 8/2005 Rubinsky et al.
6,941,950 B2 9/2005 Wilson et al.
6,942,681 B2 9/2005 Johnson
6,958,062 B1 10/2005 Gough et al.
6,960,189 B2 11/2005 Bates et al.
6,962,587 B2 * 11/2005 Johnson ............. A61B 18/1477 606/41
6,972,013 B1 12/2005 Zhang et al.
6,972,014 B2 12/2005 Eum et al.
6,989,010 B2 1/2006 Francischelli et al.
6,994,689 B1 2/2006 Zadno-Azizi et al.
6,994,706 B2 2/2006 Chornenky et al.
7,011,094 B2 3/2006 Rapacki et al.
7,012,061 B1 3/2006 Reiss et al.
7,027,869 B2 4/2006 Danek et al.
7,036,510 B2 5/2006 Zgoda et al.
7,053,063 B2 5/2006 Rubinsky et al.
7,054,685 B2 5/2006 Dimmer et al.
7,063,698 B2 6/2006 Whayne et al.
7,087,040 B2 8/2006 McGuckin et al.
7,097,612 B2 8/2006 Bertolero et al.
7,100,616 B2 9/2006 Springmeyer
7,113,821 B1 9/2006 Sun et al.
7,130,697 B2 10/2006 Chornenky et al.
7,211,083 B2 5/2007 Chornenky et al.
7,232,437 B2 6/2007 Berman et al.
7,250,048 B2 7/2007 Francischelli et al.
D549,332 S 8/2007 Matsumoto et al.
7,257,450 B2 8/2007 Auth et al.
7,264,002 B2 9/2007 Danek et al.
7,267,676 B2 9/2007 Chornenky et al.
7,273,055 B2 9/2007 Danek et al.
7,291,146 B2 11/2007 Steinke et al.
7,331,940 B2 2/2008 Sommerich
7,331,949 B2 2/2008 Marisi
7,341,558 B2 3/2008 Torre et al.
7,344,533 B2 * 3/2008 Pearson ............. A61B 18/1477 606/41
D565,743 S 4/2008 Phillips et al.
D571,478 S 6/2008 Horacek
7,387,626 B2 6/2008 Edwards et al.
7,399,747 B1 7/2008 Clair et al.
D575,399 S 8/2008 Matsumoto et al.
D575,402 S 8/2008 Sandor
7,419,487 B2 9/2008 Johnson et al.
7,434,578 B2 10/2008 Dillard et al.
7,449,019 B2 11/2008 Uchida et al.
7,451,765 B2 11/2008 Adler
7,455,675 B2 11/2008 Schur et al.
7,476,203 B2 1/2009 DeVore et al.
7,520,877 B2 4/2009 Lee et al.
7,533,671 B2 5/2009 Gonzalez et al.
D595,422 S 6/2009 Mustapha
7,544,301 B2 6/2009 Shah et al.
7,549,984 B2 6/2009 Mathis
7,565,208 B2 7/2009 Harris et al.
7,571,729 B2 8/2009 Saadat et al.
7,632,291 B2 12/2009 Stephens et al.
7,655,004 B2 2/2010 Long
7,674,249 B2 3/2010 Ivorra et al.
7,680,543 B2 * 3/2010 Azure ...................... A61N 1/06 606/41
D613,418 S 4/2010 Ryan et al.
7,718,409 B2 5/2010 Rubinsky et al.
7,722,606 B2 5/2010 Azure
7,742,795 B2 6/2010 Stone et al.
7,765,010 B2 7/2010 Chornenky et al.
7,771,401 B2 8/2010 Hekmat et al.
RE42,016 E 12/2010 Chornenky et al.
D630,321 S 1/2011 Hamilton
D631,154 S 1/2011 Hamilton
7,871,406 B2 1/2011 Nields et al.
RE42,277 E 4/2011 Jaafar et al.
7,918,852 B2 4/2011 Tullis et al.
7,937,143 B2 5/2011 Demarais et al.
7,938,824 B2 5/2011 Chornenky et al.
7,951,582 B2 5/2011 Gazit et al.
7,955,827 B2 6/2011 Rubinsky et al.

(56) References Cited

U.S. PATENT DOCUMENTS

| | | | |
|---|---|---|---|
| RE42,835 | E | 10/2011 | Chornenky et al. |
| D647,628 | S | 10/2011 | Helfteren |
| 8,048,067 | B2 | 11/2011 | Davalos et al. |
| 8,055,323 | B2 | 11/2011 | Sawyer |
| RE43,009 | E | 12/2011 | Chornenky et al. |
| 8,109,926 | B2 | 2/2012 | Azure |
| 8,114,070 | B2 | 2/2012 | Rubinsky et al. |
| 8,162,918 | B2 | 4/2012 | Ivorra et al. |
| 8,187,269 | B2 | 5/2012 | Shadduck et al. |
| 8,221,411 | B2 | 7/2012 | Francischelli et al. |
| 8,231,603 | B2 | 7/2012 | Hobbs et al. |
| 8,240,468 | B2 | 8/2012 | Wilkinson et al. |
| 8,251,986 | B2 | 8/2012 | Chornenky et al. |
| 8,267,927 | B2 | 9/2012 | Dalal et al. |
| 8,267,936 | B2 | 9/2012 | Hushka et al. |
| 8,282,631 | B2 | 10/2012 | Davalos et al. |
| 8,298,222 | B2 | 10/2012 | Rubinsky et al. |
| 8,348,921 | B2 | 1/2013 | Ivorra et al. |
| 8,361,066 | B2 | 1/2013 | Long et al. |
| D677,798 | S | 3/2013 | Hart et al. |
| 8,403,925 | B2 | 3/2013 | Miller et al. |
| 8,425,455 | B2 | 4/2013 | Nentwick |
| 8,425,505 | B2 | 4/2013 | Long |
| 8,454,594 | B2 | 6/2013 | Demarais et al. |
| 8,465,464 | B2 | 6/2013 | Travis et al. |
| 8,465,484 | B2 | 6/2013 | Davalos et al. |
| 8,506,564 | B2 | 8/2013 | Long et al. |
| 8,511,317 | B2 | 8/2013 | Thapliyal et al. |
| 8,518,031 | B2 | 8/2013 | Boyden et al. |
| 8,562,588 | B2 | 10/2013 | Hobbs et al. |
| 8,603,087 | B2 | 12/2013 | Rubinsky et al. |
| 8,632,534 | B2 | 1/2014 | Pearson et al. |
| 8,634,929 | B2 | 1/2014 | Chornenky et al. |
| 8,647,338 | B2 | 2/2014 | Chornenky et al. |
| 8,670,816 | B2 | 3/2014 | Green et al. |
| 8,715,276 | B2 | 5/2014 | Thompson et al. |
| 8,753,335 | B2 | 6/2014 | Moshe et al. |
| 8,814,860 | B2 | 8/2014 | Davalos et al. |
| 8,835,166 | B2 | 9/2014 | Phillips et al. |
| 8,845,635 | B2 | 9/2014 | Daniel et al. |
| 8,880,195 | B2 | 11/2014 | Azure |
| 8,903,488 | B2 | 12/2014 | Callas et al. |
| 8,906,006 | B2 | 12/2014 | Chornenky et al. |
| 8,926,606 | B2 | 1/2015 | Davalos et al. |
| 8,958,888 | B2 | 2/2015 | Chornenky et al. |
| 8,968,542 | B2 | 3/2015 | Davalos et al. |
| 8,992,517 | B2 | 3/2015 | Davalos et al. |
| 9,005,189 | B2 | 4/2015 | Davalos et al. |
| 9,014,789 | B2 | 4/2015 | Mercader et al. |
| 9,078,665 | B2 | 7/2015 | Moss et al. |
| 9,149,331 | B2 | 10/2015 | Deem et al. |
| 9,173,704 | B2 | 11/2015 | Hobbs et al. |
| 9,198,733 | B2 | 12/2015 | Neal, II et al. |
| 9,283,051 | B2 | 3/2016 | Garcia et al. |
| 9,414,881 | B2 | 8/2016 | Callas et al. |
| 9,598,691 | B2 | 3/2017 | Davalos |
| 9,700,368 | B2 | 7/2017 | Callas et al. |
| 9,764,145 | B2 | 9/2017 | Callas et al. |
| 9,867,652 | B2 | 1/2018 | Sano et al. |
| 9,943,599 | B2 | 4/2018 | Gehl et al. |
| 10,117,701 | B2 | 11/2018 | Davalos et al. |
| 10,117,707 | B2 | 11/2018 | Garcia et al. |
| 10,154,874 | B2 | 12/2018 | Davalos et al. |
| 10,238,447 | B2 | 3/2019 | Neal et al. |
| 10,245,098 | B2 | 4/2019 | Davalos et al. |
| 10,245,105 | B2 | 4/2019 | Davalos et al. |
| 10,272,178 | B2 | 4/2019 | Davalos et al. |
| 10,286,108 | B2 | 5/2019 | Davalos et al. |
| 10,292,755 | B2 | 5/2019 | Davalos et al. |
| 10,448,989 | B2 | 10/2019 | Arena et al. |
| 10,470,822 | B2 | 11/2019 | Garcia et al. |
| 10,471,254 | B2 | 11/2019 | Sano et al. |
| 10,537,379 | B2 | 1/2020 | Sano et al. |
| 10,694,972 | B2 | 6/2020 | Davalos et al. |
| 10,702,326 | B2 | 7/2020 | Neal et al. |
| 10,828,085 | B2 | 11/2020 | Davalos et al. |
| 10,828,086 | B2 | 11/2020 | Davalos et al. |
| 10,959,772 | B2 | 3/2021 | Davalos et al. |
| 11,254,926 | B2 | 2/2022 | Garcia et al. |
| 11,272,979 | B2 | 3/2022 | Garcia et al. |
| 11,311,329 | B2 | 4/2022 | Davalos et al. |
| 11,382,681 | B2 | 7/2022 | Arena et al. |
| 11,406,820 | B2 | 8/2022 | Sano et al. |
| 11,453,873 | B2 | 9/2022 | Davalos et al. |
| 11,607,271 | B2 | 3/2023 | Garcia et al. |
| 11,607,537 | B2 | 3/2023 | Latouche et al. |
| 11,638,603 | B2 | 5/2023 | Sano et al. |
| 11,655,466 | B2 | 5/2023 | Neal et al. |
| 11,737,810 | B2 | 8/2023 | Davalos et al. |
| 11,890,046 | B2 | 2/2024 | Neal et al. |
| 11,903,690 | B2 | 2/2024 | Davalos et al. |
| 11,925,405 | B2 | 3/2024 | Davalos et al. |
| 11,950,835 | B2 | 4/2024 | O'Brien et al. |
| 11,952,568 | B2 | 4/2024 | Neal, II et al. |
| 11,974,800 | B2 | 5/2024 | Sano et al. |
| 12,059,197 | B2 | 8/2024 | Davalos et al. |
| 12,173,280 | B2 | 12/2024 | Neal, II et al. |
| 12,214,189 | B2 | 2/2025 | Lorenzo et al. |
| 12,232,792 | B2 | 2/2025 | Neal et al. |
| 12,390,262 | B2 | 8/2025 | Davalos et al. |
| 12,390,268 | B2 | 8/2025 | Garcia et al. |
| 12,485,279 | B2 | 12/2025 | Aycock et al. |
| 12,697,172 | B2 | 8/2026 | Garcia et al. |
| 12,708,766 | B2 | 8/2026 | Sano et al. |
| 2001/0039393 | A1 | 11/2001 | Mori et al. |
| 2001/0044596 | A1 | 11/2001 | Jaafar |
| 2001/0046706 | A1 | 11/2001 | Rubinsky et al. |
| 2001/0047167 | A1 | 11/2001 | Heggeness |
| 2001/0051366 | A1 | 12/2001 | Rubinsky et al. |
| 2002/0002393 | A1 | 1/2002 | Mitchell |
| 2002/0010491 | A1 | 1/2002 | Schoenbach et al. |
| 2002/0022864 | A1 | 2/2002 | Mahvi et al. |
| 2002/0040204 | A1 | 4/2002 | Dev et al. |
| 2002/0049370 | A1 | 4/2002 | Laufer et al. |
| 2002/0052601 | A1 | 5/2002 | Goldberg et al. |
| 2002/0055731 | A1 | 5/2002 | Atala et al. |
| 2002/0065541 | A1 | 5/2002 | Fredricks et al. |
| 2002/0072742 | A1 | 6/2002 | Schaefer et al. |
| 2002/0077314 | A1 | 6/2002 | Falk et al. |
| 2002/0077627 | A1 | 6/2002 | Johnson et al. |
| 2002/0077676 | A1 | 6/2002 | Schroeppel et al. |
| 2002/0082543 | A1 | 6/2002 | Park et al. |
| 2002/0099323 | A1 | 7/2002 | Dev et al. |
| 2002/0104318 | A1 | 8/2002 | Jaafar et al. |
| 2002/0111615 | A1 | 8/2002 | Cosman et al. |
| 2002/0112729 | A1 | 8/2002 | DeVore et al. |
| 2002/0115208 | A1 | 8/2002 | Mitchell et al. |
| 2002/0119437 | A1 | 8/2002 | Grooms et al. |
| 2002/0133324 | A1 | 9/2002 | Weaver et al. |
| 2002/0137121 | A1 | 9/2002 | Rubinsky et al. |
| 2002/0138075 | A1 | 9/2002 | Edwards et al. |
| 2002/0138117 | A1 | 9/2002 | Son |
| 2002/0143365 | A1 | 10/2002 | Herbst |
| 2002/0147462 | A1 | 10/2002 | Mair et al. |
| 2002/0156472 | A1 | 10/2002 | Lee et al. |
| 2002/0161361 | A1 | 10/2002 | Sherman et al. |
| 2002/0183684 | A1 | 12/2002 | Dev et al. |
| 2002/0183735 | A1 | 12/2002 | Edwards et al. |
| 2002/0183740 | A1 | 12/2002 | Edwards et al. |
| 2002/0188242 | A1 | 12/2002 | Wu |
| 2002/0193784 | A1 | 12/2002 | McHale et al. |
| 2002/0193831 | A1 | 12/2002 | Edward |
| 2003/0009110 | A1 | 1/2003 | Tu et al. |
| 2003/0016168 | A1 | 1/2003 | Jandrell |
| 2003/0055220 | A1 | 3/2003 | Legrain |
| 2003/0055420 | A1 | 3/2003 | Kadhiresan et al. |
| 2003/0059945 | A1 | 3/2003 | Dzekunov et al. |
| 2003/0060856 | A1 | 3/2003 | Chornenky et al. |
| 2003/0078490 | A1 | 4/2003 | Damasco et al. |
| 2003/0088189 | A1 | 5/2003 | Tu et al. |
| 2003/0088199 | A1 | 5/2003 | Kawaji |
| 2003/0096407 | A1 | 5/2003 | Atala et al. |
| 2003/0105454 | A1 | 6/2003 | Cucin |
| 2003/0109871 | A1 | 6/2003 | Johnson et al. |

(56) References Cited

U.S. PATENT DOCUMENTS

| | | | |
|---|---|---|---|
| 2003/0127090 | A1 | 7/2003 | Gifford et al. |
| 2003/0130711 | A1 | 7/2003 | Pearson et al. |
| 2003/0135242 | A1 | 7/2003 | Mongeon et al. |
| 2003/0149451 | A1 | 8/2003 | Chomenky et al. |
| 2003/0153960 | A1 | 8/2003 | Chornenky et al. |
| 2003/0154988 | A1 | 8/2003 | DeVore et al. |
| 2003/0159700 | A1 | 8/2003 | Laufer et al. |
| 2003/0166181 | A1 | 9/2003 | Rubinsky et al. |
| 2003/0170898 | A1 | 9/2003 | Gundersen et al. |
| 2003/0194808 | A1 | 10/2003 | Rubinsky et al. |
| 2003/0195385 | A1 | 10/2003 | DeVore |
| 2003/0195406 | A1 | 10/2003 | Jenkins et al. |
| 2003/0199050 | A1 | 10/2003 | Mangano et al. |
| 2003/0208200 | A1 | 11/2003 | Palanker et al. |
| 2003/0208236 | A1 | 11/2003 | Heil et al. |
| 2003/0212394 | A1 | 11/2003 | Pearson et al. |
| 2003/0212412 | A1 | 11/2003 | Dillard et al. |
| 2003/0225360 | A1 | 12/2003 | Eppstein et al. |
| 2003/0228344 | A1 | 12/2003 | Fields et al. |
| 2004/0009459 | A1 | 1/2004 | Anderson et al. |
| 2004/0019371 | A1 | 1/2004 | Jaafar et al. |
| 2004/0055606 | A1 | 3/2004 | Hendricksen et al. |
| 2004/0059328 | A1 | 3/2004 | Daniel et al. |
| 2004/0059389 | A1 | 3/2004 | Chornenky et al. |
| 2004/0068228 | A1 | 4/2004 | Cunningham |
| 2004/0116965 | A1 | 6/2004 | Falkenberg |
| 2004/0133194 | A1 | 7/2004 | Eum et al. |
| 2004/0138715 | A1 | 7/2004 | Groeningen et al. |
| 2004/0146877 | A1 | 7/2004 | Diss et al. |
| 2004/0153057 | A1 | 8/2004 | Davison |
| 2004/0176855 | A1 | 9/2004 | Badylak |
| 2004/0187875 | A1 | 9/2004 | He et al. |
| 2004/0193042 | A1 | 9/2004 | Scampini et al. |
| 2004/0193097 | A1 | 9/2004 | Hofmann et al. |
| 2004/0199159 | A1 | 10/2004 | Lee et al. |
| 2004/0200484 | A1 | 10/2004 | Springmeyer |
| 2004/0206349 | A1 | 10/2004 | Alferness et al. |
| 2004/0210248 | A1 | 10/2004 | Gordon et al. |
| 2004/0230187 | A1 | 11/2004 | Lee et al. |
| 2004/0236376 | A1 | 11/2004 | Miklavcic et al. |
| 2004/0243107 | A1 | 12/2004 | Macoviak et al. |
| 2004/0267189 | A1 | 12/2004 | Mavor et al. |
| 2004/0267340 | A1 | 12/2004 | Cioanta et al. |
| 2005/0004507 | A1 | 1/2005 | Schroeppel et al. |
| 2005/0010209 | A1 | 1/2005 | Lee et al. |
| 2005/0010259 | A1 | 1/2005 | Gerber |
| 2005/0013870 | A1 | 1/2005 | Freyman et al. |
| 2005/0020965 | A1 | 1/2005 | Rioux et al. |
| 2005/0043726 | A1 | 2/2005 | McHale et al. |
| 2005/0048651 | A1 | 3/2005 | Ryttsen et al. |
| 2005/0049541 | A1 | 3/2005 | Behar et al. |
| 2005/0061322 | A1 | 3/2005 | Freitag |
| 2005/0066974 | A1 | 3/2005 | Fields et al. |
| 2005/0112141 | A1 | 5/2005 | Terman |
| 2005/0143817 | A1 | 6/2005 | Hunter et al. |
| 2005/0165393 | A1 | 7/2005 | Eppstein |
| 2005/0171522 | A1 | 8/2005 | Christopherson |
| 2005/0171523 | A1 | 8/2005 | Rubinsky et al. |
| 2005/0171574 | A1 | 8/2005 | Rubinsky et al. |
| 2005/0182462 | A1 | 8/2005 | Chornenky et al. |
| 2005/0197619 | A1 | 9/2005 | Rule et al. |
| 2005/0261672 | A1 | 11/2005 | Deem et al. |
| 2005/0267407 | A1 | 12/2005 | Goldman |
| 2005/0282284 | A1 | 12/2005 | Rubinsky et al. |
| 2005/0283149 | A1 | 12/2005 | Thorne et al. |
| 2005/0288684 | A1 | 12/2005 | Aronson et al. |
| 2005/0288702 | A1 | 12/2005 | McGurk et al. |
| 2005/0288730 | A1 | 12/2005 | Deem et al. |
| 2006/0004356 | A1 | 1/2006 | Bilski et al. |
| 2006/0004400 | A1 | 1/2006 | McGurk et al. |
| 2006/0009748 | A1 | 1/2006 | Mathis |
| 2006/0015147 | A1 | 1/2006 | Persson et al. |
| 2006/0020347 | A1 | 1/2006 | Barrett et al. |
| 2006/0024359 | A1 | 2/2006 | Walker et al. |
| 2006/0025760 | A1 | 2/2006 | Podhajsky |
| 2006/0074413 | A1 | 4/2006 | Behzadian |
| 2006/0079838 | A1 | 4/2006 | Walker et al. |
| 2006/0079845 | A1 | 4/2006 | Howard et al. |
| 2006/0079883 | A1 | 4/2006 | Elmouelhi et al. |
| 2006/0085054 | A1 | 4/2006 | Zikorus et al. |
| 2006/0089635 | A1 | 4/2006 | Young et al. |
| 2006/0121610 | A1 | 6/2006 | Rubinsky et al. |
| 2006/0142801 | A1 | 6/2006 | Demarais et al. |
| 2006/0149123 | A1 | 7/2006 | Vidlund et al. |
| 2006/0173490 | A1 | 8/2006 | Lafontaine et al. |
| 2006/0182684 | A1 | 8/2006 | Beliveau |
| 2006/0195146 | A1 | 8/2006 | Tracey et al. |
| 2006/0212032 | A1 | 9/2006 | Daniel et al. |
| 2006/0212078 | A1 | 9/2006 | Demarais et al. |
| 2006/0217703 | A1 | 9/2006 | Chornenky et al. |
| 2006/0224188 | A1 | 10/2006 | Libbus et al. |
| 2006/0235474 | A1 | 10/2006 | Demarais |
| 2006/0247619 | A1 | 11/2006 | Kaplan et al. |
| 2006/0264752 | A1 * | 11/2006 | Rubinsky ............. A61B 8/0833 606/41 |
| 2006/0264807 | A1 | 11/2006 | Westersten et al. |
| 2006/0269531 | A1 | 11/2006 | Beebe et al. |
| 2006/0276710 | A1 | 12/2006 | Krishnan |
| 2006/0278241 | A1 | 12/2006 | Ruano |
| 2006/0283462 | A1 | 12/2006 | Fields et al. |
| 2006/0293713 | A1 | 12/2006 | Rubinsky et al. |
| 2006/0293725 | A1 | 12/2006 | Rubinsky et al. |
| 2006/0293730 | A1 | 12/2006 | Rubinsky et al. |
| 2006/0293731 | A1 | 12/2006 | Rubinsky et al. |
| 2006/0293734 | A1 | 12/2006 | Scott et al. |
| 2007/0010805 | A1 | 1/2007 | Fedewa et al. |
| 2007/0016125 | A1 | 1/2007 | Wong et al. |
| 2007/0016183 | A1 | 1/2007 | Lee et al. |
| 2007/0016185 | A1 | 1/2007 | Tullis et al. |
| 2007/0021803 | A1 | 1/2007 | Deem et al. |
| 2007/0025919 | A1 | 2/2007 | Deem et al. |
| 2007/0043345 | A1 | 2/2007 | Davalos et al. |
| 2007/0060989 | A1 | 3/2007 | Deem et al. |
| 2007/0078391 | A1 | 4/2007 | Wortley et al. |
| 2007/0088347 | A1 | 4/2007 | Young et al. |
| 2007/0093789 | A1 | 4/2007 | Smith |
| 2007/0096048 | A1 | 5/2007 | Clerc |
| 2007/0118069 | A1 | 5/2007 | Persson et al. |
| 2007/0129711 | A1 | 6/2007 | Altshuler et al. |
| 2007/0129720 | A1 | 6/2007 | Demarais et al. |
| 2007/0129760 | A1 | 6/2007 | Demarais et al. |
| 2007/0151848 | A1 | 7/2007 | Novak et al. |
| 2007/0156135 | A1 | 7/2007 | Rubinsky et al. |
| 2007/0191889 | A1 | 8/2007 | Lang |
| 2007/0203486 | A1 | 8/2007 | Young |
| 2007/0230757 | A1 | 10/2007 | Trachtenberg et al. |
| 2007/0239099 | A1 | 10/2007 | Goldfarb et al. |
| 2007/0244521 | A1 | 10/2007 | Bornzin et al. |
| 2007/0287950 | A1 | 12/2007 | Kjeken et al. |
| 2007/0295336 | A1 | 12/2007 | Nelson et al. |
| 2007/0295337 | A1 | 12/2007 | Nelson et al. |
| 2008/0009102 | A1 | 1/2008 | Yang et al. |
| 2008/0015571 | A1 | 1/2008 | Rubinsky et al. |
| 2008/0021371 | A1 | 1/2008 | Rubinsky et al. |
| 2008/0027314 | A1 | 1/2008 | Miyazaki et al. |
| 2008/0027343 | A1 | 1/2008 | Fields et al. |
| 2008/0033340 | A1 | 2/2008 | Heller et al. |
| 2008/0033417 | A1 | 2/2008 | Nields et al. |
| 2008/0045880 | A1 | 2/2008 | Kjeken et al. |
| 2008/0052786 | A1 | 2/2008 | Lin et al. |
| 2008/0065062 | A1 | 3/2008 | Leung et al. |
| 2008/0071262 | A1 | 3/2008 | Azure |
| 2008/0071264 | A1 | 3/2008 | Azure |
| 2008/0097139 | A1 | 4/2008 | Clerc et al. |
| 2008/0097422 | A1 | 4/2008 | Edwards et al. |
| 2008/0103529 | A1 | 5/2008 | Schoenbach et al. |
| 2008/0112963 | A1 | 5/2008 | Har-Noy |
| 2008/0121375 | A1 | 5/2008 | Richason et al. |
| 2008/0125772 | A1 | 5/2008 | Stone et al. |
| 2008/0132826 | A1 | 6/2008 | Shadduck et al. |
| 2008/0132884 | A1 | 6/2008 | Rubinsky et al. |
| 2008/0132885 | A1 | 6/2008 | Rubinsky et al. |
| 2008/0140064 | A1 | 6/2008 | Vegesna |
| 2008/0146934 | A1 | 6/2008 | Czygan et al. |

(56) References Cited

U.S. PATENT DOCUMENTS

| | | | |
|---|---|---|---|
| 2008/0154259 | A1 | 6/2008 | Gough et al. |
| 2008/0167649 | A1 | 7/2008 | Edwards et al. |
| 2008/0171985 | A1 | 7/2008 | Karakoca |
| 2008/0190434 | A1 | 8/2008 | Wai |
| 2008/0200911 | A1 | 8/2008 | Long |
| 2008/0200912 | A1 | 8/2008 | Long |
| 2008/0208052 | A1 | 8/2008 | LePivert et al. |
| 2008/0210243 | A1 | 9/2008 | Clayton et al. |
| 2008/0214986 | A1 | 9/2008 | Ivorra et al. |
| 2008/0236593 | A1 | 10/2008 | Nelson et al. |
| 2008/0249503 | A1 | 10/2008 | Fields et al. |
| 2008/0262489 | A1 | 10/2008 | Steinke |
| 2008/0269586 | A1 | 10/2008 | Rubinsky et al. |
| 2008/0269838 | A1 | 10/2008 | Brighton et al. |
| 2008/0275465 | A1 | 11/2008 | Paul et al. |
| 2008/0281319 | A1 | 11/2008 | Paul et al. |
| 2008/0283065 | A1 | 11/2008 | Chang et al. |
| 2008/0288038 | A1 | 11/2008 | Paul et al. |
| 2008/0300589 | A1 | 12/2008 | Paul et al. |
| 2008/0306427 | A1 | 12/2008 | Bailey |
| 2008/0312599 | A1 | 12/2008 | Rosenberg |
| 2009/0018206 | A1 | 1/2009 | Barkan et al. |
| 2009/0024075 | A1 | 1/2009 | Schroeppel et al. |
| 2009/0029407 | A1 | 1/2009 | Gazit et al. |
| 2009/0038752 | A1 | 2/2009 | Weng et al. |
| 2009/0062788 | A1 | 3/2009 | Long et al. |
| 2009/0062792 | A1 | 3/2009 | Vakharia et al. |
| 2009/0062795 | A1 | 3/2009 | Vakharia et al. |
| 2009/0081272 | A1 | 3/2009 | Clarke et al. |
| 2009/0105703 | A1 | 4/2009 | Shadduck |
| 2009/0114226 | A1 | 5/2009 | Deem et al. |
| 2009/0125009 | A1 | 5/2009 | Zikorus et al. |
| 2009/0138014 | A1 | 5/2009 | Bonutti |
| 2009/0143705 | A1 | 6/2009 | Danek et al. |
| 2009/0157166 | A1 | 6/2009 | Singhal et al. |
| 2009/0163904 | A1 | 6/2009 | Miller et al. |
| 2009/0171280 | A1 | 7/2009 | Samuel et al. |
| 2009/0177111 | A1 | 7/2009 | Miller et al. |
| 2009/0186850 | A1 | 7/2009 | Kiribayashi et al. |
| 2009/0192508 | A1 | 7/2009 | Laufer et al. |
| 2009/0198231 | A1 | 8/2009 | Esser et al. |
| 2009/0228001 | A1 | 9/2009 | Pacey |
| 2009/0247933 | A1 | 10/2009 | Maor et al. |
| 2009/0248012 | A1 | 10/2009 | Maor et al. |
| 2009/0269317 | A1 | 10/2009 | Davalos |
| 2009/0275827 | A1 | 11/2009 | Aiken et al. |
| 2009/0281477 | A1* | 11/2009 | Mikus ................ A61B 18/1477 606/41 |
| 2009/0292342 | A1 | 11/2009 | Rubinsky et al. |
| 2009/0301480 | A1 | 12/2009 | Elsakka et al. |
| 2009/0306544 | A1 | 12/2009 | Ng et al. |
| 2009/0306545 | A1 | 12/2009 | Elsakka et al. |
| 2009/0318905 | A1* | 12/2009 | Bhargav ................. A61B 18/14 606/1 |
| 2009/0326346 | A1 | 12/2009 | Kracker et al. |
| 2009/0326366 | A1 | 12/2009 | Krieg |
| 2009/0326436 | A1 | 12/2009 | Rubinsky et al. |
| 2009/0326570 | A1 | 12/2009 | Brown |
| 2010/0004623 | A1 | 1/2010 | Hamilton, Jr. et al. |
| 2010/0006441 | A1 | 1/2010 | Renaud et al. |
| 2010/0023004 | A1 | 1/2010 | Francischelli et al. |
| 2010/0030211 | A1 | 2/2010 | Davalos et al. |
| 2010/0049190 | A1 | 2/2010 | Long et al. |
| 2010/0057074 | A1 | 3/2010 | Roman et al. |
| 2010/0069921 | A1 | 3/2010 | Miller et al. |
| 2010/0087813 | A1 | 4/2010 | Long |
| 2010/0130975 | A1 | 5/2010 | Long |
| 2010/0147701 | A1 | 6/2010 | Field |
| 2010/0152725 | A1 | 6/2010 | Pearson et al. |
| 2010/0160850 | A1 | 6/2010 | Ivorra et al. |
| 2010/0168735 | A1 | 7/2010 | Deno et al. |
| 2010/0174282 | A1 | 7/2010 | Demarais et al. |
| 2010/0179530 | A1 | 7/2010 | Long et al. |
| 2010/0196984 | A1 | 8/2010 | Rubinsky et al. |
| 2010/0204560 | A1 | 8/2010 | Salahieh et al. |
| 2010/0204638 | A1 | 8/2010 | Hobbs et al. |
| 2010/0222677 | A1 | 9/2010 | Placek et al. |
| 2010/0228234 | A1 | 9/2010 | Hyde et al. |
| 2010/0228247 | A1 | 9/2010 | Paul et al. |
| 2010/0241117 | A1 | 9/2010 | Paul et al. |
| 2010/0249771 | A1 | 9/2010 | Pearson et al. |
| 2010/0250209 | A1 | 9/2010 | Pearson et al. |
| 2010/0255795 | A1 | 10/2010 | Rubinsky et al. |
| 2010/0256628 | A1 | 10/2010 | Pearson et al. |
| 2010/0256630 | A1 | 10/2010 | Hamilton, Jr. et al. |
| 2010/0261994 | A1 | 10/2010 | Davalos et al. |
| 2010/0286690 | A1 | 11/2010 | Paul et al. |
| 2010/0298823 | A1 | 11/2010 | Cao et al. |
| 2010/0331758 | A1* | 12/2010 | Davalos ............. A61B 18/1477 604/20 |
| 2011/0017207 | A1 | 1/2011 | Hendricksen et al. |
| 2011/0034209 | A1 | 2/2011 | Rubinsky et al. |
| 2011/0064671 | A1 | 3/2011 | Bynoe |
| 2011/0092973 | A1 | 4/2011 | Nuccitelli et al. |
| 2011/0106221 | A1 | 5/2011 | Neal et al. |
| 2011/0112531 | A1 | 5/2011 | Landis et al. |
| 2011/0118727 | A1 | 5/2011 | Fish et al. |
| 2011/0118732 | A1 | 5/2011 | Rubinsky et al. |
| 2011/0130834 | A1 | 6/2011 | Wilson et al. |
| 2011/0144524 | A1 | 6/2011 | Fish et al. |
| 2011/0144635 | A1 | 6/2011 | Harper et al. |
| 2011/0144657 | A1 | 6/2011 | Fish et al. |
| 2011/0152678 | A1 | 6/2011 | Aljuri et al. |
| 2011/0166499 | A1 | 7/2011 | Demarais et al. |
| 2011/0176037 | A1 | 7/2011 | Benkley, III |
| 2011/0202053 | A1 | 8/2011 | Moss et al. |
| 2011/0217730 | A1 | 9/2011 | Gazit et al. |
| 2011/0251607 | A1 | 10/2011 | Kruecker et al. |
| 2011/0301587 | A1 | 12/2011 | Deem et al. |
| 2012/0034131 | A1 | 2/2012 | Rubinsky et al. |
| 2012/0059255 | A1 | 3/2012 | Paul et al. |
| 2012/0071870 | A1 | 3/2012 | Salahieh et al. |
| 2012/0071872 | A1 | 3/2012 | Rubinsky et al. |
| 2012/0071874 | A1 | 3/2012 | Davalos et al. |
| 2012/0085649 | A1 | 4/2012 | Sano et al. |
| 2012/0089009 | A1 | 4/2012 | Omary et al. |
| 2012/0090646 | A1 | 4/2012 | Tanaka et al. |
| 2012/0095459 | A1 | 4/2012 | Callas et al. |
| 2012/0109122 | A1 | 5/2012 | Arena et al. |
| 2012/0130289 | A1 | 5/2012 | Demarais et al. |
| 2012/0139734 | A1 | 6/2012 | Olde et al. |
| 2012/0150172 | A1 | 6/2012 | Ortiz et al. |
| 2012/0165813 | A1 | 6/2012 | Lee et al. |
| 2012/0179091 | A1 | 7/2012 | Ivorra et al. |
| 2012/0226218 | A1 | 9/2012 | Phillips et al. |
| 2012/0226271 | A1 | 9/2012 | Callas et al. |
| 2012/0265186 | A1 | 10/2012 | Burger et al. |
| 2012/0277741 | A1 | 11/2012 | Davalos et al. |
| 2012/0303020 | A1 | 11/2012 | Chornenky et al. |
| 2012/0310236 | A1 | 12/2012 | Placek et al. |
| 2013/0023871 | A1 | 1/2013 | Collins |
| 2013/0030239 | A1 | 1/2013 | Weyh et al. |
| 2013/0090646 | A1 | 4/2013 | Moss et al. |
| 2013/0108667 | A1 | 5/2013 | Soikum et al. |
| 2013/0110106 | A1 | 5/2013 | Richardson |
| 2013/0184702 | A1 | 7/2013 | Neal et al. |
| 2013/0196441 | A1 | 8/2013 | Rubinsky et al. |
| 2013/0197425 | A1 | 8/2013 | Golberg et al. |
| 2013/0202766 | A1 | 8/2013 | Rubinsky et al. |
| 2013/0218157 | A1 | 8/2013 | Callas et al. |
| 2013/0253415 | A1 | 9/2013 | Sano et al. |
| 2013/0281968 | A1 | 10/2013 | Davalos et al. |
| 2013/0345697 | A1 | 12/2013 | Garcia et al. |
| 2013/0345779 | A1 | 12/2013 | Maor et al. |
| 2014/0017218 | A1 | 1/2014 | Scott et al. |
| 2014/0039489 | A1 | 2/2014 | Davalos et al. |
| 2014/0046322 | A1 | 2/2014 | Callas et al. |
| 2014/0066913 | A1 | 3/2014 | Sherman |
| 2014/0081255 | A1 | 3/2014 | Johnson et al. |
| 2014/0088578 | A1 | 3/2014 | Rubinsky et al. |
| 2014/0121663 | A1 | 5/2014 | Pearson et al. |
| 2014/0121728 | A1 | 5/2014 | Dhillon et al. |
| 2014/0163551 | A1 | 6/2014 | Maor et al. |
| 2014/0207133 | A1 | 7/2014 | Model et al. |

(56) References Cited

U.S. PATENT DOCUMENTS

| | | | |
|---|---|---|---|
| 2014/0276748 | A1 | 9/2014 | Ku et al. |
| 2014/0296844 | A1 | 10/2014 | Kevin et al. |
| 2014/0309579 | A1 | 10/2014 | Rubinsky et al. |
| 2014/0378964 | A1 | 12/2014 | Pearson |
| 2015/0088120 | A1 | 3/2015 | Garcia et al. |
| 2015/0088220 | A1 | 3/2015 | Callas et al. |
| 2015/0112333 | A1 | 4/2015 | Chorenky et al. |
| 2015/0126922 | A1 | 5/2015 | Willis |
| 2015/0152504 | A1 | 6/2015 | Lin |
| 2015/0164584 | A1 | 6/2015 | Davalos et al. |
| 2015/0173824 | A1 | 6/2015 | Davalos et al. |
| 2015/0201996 | A1 | 7/2015 | Rubinsky et al. |
| 2015/0265349 | A1 | 9/2015 | Moss et al. |
| 2015/0289923 | A1 | 10/2015 | Davalos et al. |
| 2015/0320478 | A1 | 11/2015 | Cosman, Jr. et al. |
| 2015/0320488 | A1 | 11/2015 | Moshe et al. |
| 2015/0320999 | A1 | 11/2015 | Nuccitelli et al. |
| 2015/0327944 | A1 | 11/2015 | Robert et al. |
| 2016/0022957 | A1 | 1/2016 | Hobbs et al. |
| 2016/0066977 | A1 | 3/2016 | Neal et al. |
| 2016/0074114 | A1 | 3/2016 | Pearson et al. |
| 2016/0113708 | A1 | 4/2016 | Moss et al. |
| 2016/0143698 | A1 | 5/2016 | Garcia et al. |
| 2016/0235470 | A1 | 8/2016 | Callas et al. |
| 2016/0287313 | A1 | 10/2016 | Rubinsky et al. |
| 2016/0287314 | A1 | 10/2016 | Arena et al. |
| 2016/0338758 | A9 | 11/2016 | Davalos et al. |
| 2016/0338761 | A1 | 11/2016 | Chornenky et al. |
| 2016/0354142 | A1 | 12/2016 | Pearson et al. |
| 2016/0367310 | A1 | 12/2016 | Onik et al. |
| 2017/0035501 | A1 | 2/2017 | Chornenky et al. |
| 2017/0086713 | A1 | 3/2017 | Pushpala et al. |
| 2017/0189579 | A1 | 7/2017 | Davalos |
| 2017/0209620 | A1 | 7/2017 | Davalos et al. |
| 2017/0266438 | A1 | 9/2017 | Sano |
| 2017/0319851 | A1 | 11/2017 | Athos et al. |
| 2017/0348525 | A1 | 12/2017 | Sano et al. |
| 2017/0360326 | A1 | 12/2017 | Davalos |
| 2018/0028260 | A1 | 2/2018 | Onik et al. |
| 2018/0036529 | A1 | 2/2018 | Jaroszeski et al. |
| 2018/0071014 | A1 | 3/2018 | Neal et al. |
| 2018/0125565 | A1 | 5/2018 | Sano et al. |
| 2018/0132922 | A1 | 5/2018 | Neal, II |
| 2018/0161086 | A1 | 6/2018 | Davalos et al. |
| 2018/0177543 | A1 | 6/2018 | You et al. |
| 2018/0198218 | A1 | 7/2018 | Regan et al. |
| 2019/0023804 | A1 | 1/2019 | Onik et al. |
| 2019/0029749 | A1 | 1/2019 | Garcia et al. |
| 2019/0046255 | A1 | 2/2019 | Davalos et al. |
| 2019/0069945 | A1 | 3/2019 | Davalos et al. |
| 2019/0076528 | A1 | 3/2019 | Soden et al. |
| 2019/0083169 | A1 | 3/2019 | Single et al. |
| 2019/0133671 | A1 | 5/2019 | Davalos et al. |
| 2019/0175248 | A1 | 6/2019 | Neal, II |
| 2019/0175260 | A1 | 6/2019 | Davalos |
| 2019/0223938 | A1 | 7/2019 | Arena et al. |
| 2019/0232048 | A1 | 8/2019 | Latouche et al. |
| 2019/0233809 | A1 | 8/2019 | Neal et al. |
| 2019/0256839 | A1 | 8/2019 | Neal et al. |
| 2019/0282294 | A1 | 9/2019 | Davalos et al. |
| 2019/0328445 | A1 | 10/2019 | Sano et al. |
| 2019/0351224 | A1 | 11/2019 | Sano et al. |
| 2019/0376055 | A1 | 12/2019 | Davalos et al. |
| 2020/0046432 | A1 | 2/2020 | Garcia et al. |
| 2020/0046967 | A1 | 2/2020 | Ivey et al. |
| 2020/0093541 | A9 | 3/2020 | Neal et al. |
| 2020/0197073 | A1 | 6/2020 | Sano et al. |
| 2020/0260987 | A1 | 8/2020 | Davalos et al. |
| 2020/0261718 | A1 | 8/2020 | Sarnago Andía et al. |
| 2020/0323576 | A1 | 10/2020 | Neal et al. |
| 2020/0405373 | A1 | 12/2020 | O'Brien et al. |
| 2021/0022795 | A1 | 1/2021 | Davalos et al. |
| 2021/0023362 | A1 | 1/2021 | Lorenzo et al. |
| 2021/0052882 | A1 | 2/2021 | Wasson et al. |
| 2021/0113265 | A1 | 4/2021 | D'Agostino et al. |
| 2021/0137410 | A1 | 5/2021 | O'Brien et al. |
| 2021/0186600 | A1 | 6/2021 | Davalos et al. |
| 2021/0361341 | A1 | 11/2021 | Neal et al. |
| 2021/0393312 | A1 | 12/2021 | Davalos et al. |
| 2022/0151688 | A1 | 5/2022 | Garcia et al. |
| 2022/0161027 | A1 | 5/2022 | Aycock et al. |
| 2022/0290183 | A1 | 9/2022 | Davalos et al. |
| 2022/0362549 | A1 | 11/2022 | Sano et al. |
| 2023/0000543 | A1 | 1/2023 | Sano et al. |
| 2023/0157759 | A1 | 5/2023 | Garcia et al. |
| 2023/0212551 | A1 | 7/2023 | Neal et al. |
| 2023/0248414 | A1 | 8/2023 | Sano et al. |
| 2023/0355293 | A1 | 11/2023 | Davalos et al. |
| 2023/0355968 | A1 | 11/2023 | Davalos et al. |
| 2024/0008911 | A1 | 1/2024 | Davalos et al. |
| 2024/0074804 | A1 | 3/2024 | Neal et al. |
| 2024/0173063 | A1 | 5/2024 | Neal, II et al. |
| 2024/0268878 | A1 | 8/2024 | Davalos et al. |
| 2024/0277245 | A1 | 8/2024 | Davalos et al. |
| 2024/0299076 | A1 | 9/2024 | O'Brien et al. |
| 2025/0000569 | A1 | 1/2025 | Davalos et al. |
| 2025/0120762 | A1 | 4/2025 | Neal, II et al. |
| 2025/0152230 | A1 | 5/2025 | Davalos et al. |
| 2025/0177741 | A1 | 6/2025 | Lorenzo et al. |
| 2025/0205481 | A1 | 6/2025 | Davalos et al. |
| 2025/0228602 | A1 | 7/2025 | Neal, II et al. |
| 2026/0108730 | A1 | 4/2026 | Aycock et al. |
| 2026/0124444 | A1 | 5/2026 | Davalos et al. |

FOREIGN PATENT DOCUMENTS

| | | | |
|---|---|---|---|
| AU | 2003227960 | A1 | 12/2003 |
| AU | 2005271471 | A2 | 2/2006 |
| AU | 2006321570 | A1 | 6/2007 |
| AU | 2006321574 | A1 | 6/2007 |
| AU | 2006321918 | A1 | 6/2007 |
| AU | 2009243079 | A2 | 1/2011 |
| AU | 2015259303 | A1 | 11/2016 |
| CA | 2297846 | A1 | 2/1999 |
| CA | 2378110 | A1 | 2/2001 |
| CA | 2445392 | A1 | 11/2002 |
| CA | 2458676 | A1 | 3/2003 |
| CA | 2487284 | A1 | 12/2003 |
| CA | 2575792 | A1 | 2/2006 |
| CA | 2631940 | A1 | 6/2007 |
| CA | 2631946 | A1 | 6/2007 |
| CA | 2632604 | A1 | 6/2007 |
| CA | 2722296 | A1 | 11/2009 |
| CA | 2751462 | A1 | 11/2010 |
| CN | 1525839 | A | 9/2004 |
| CN | 101534736 | A | 9/2009 |
| CN | 102238921 | A | 11/2011 |
| CN | 102421386 | A | 4/2012 |
| CN | 106715682 | A | 5/2017 |
| CN | 112807074 | A | 5/2021 |
| DE | 863111 | | 1/1953 |
| DE | 4000893 | A1 | 7/1991 |
| DE | 60038026 | | 2/2009 |
| EP | 0218275 | A1 | 4/1987 |
| EP | 0339501 | A2 | 11/1989 |
| EP | 0378132 | A | 7/1990 |
| EP | 0533511 | A1 | 3/1993 |
| EP | 0998235 | A1 | 5/2000 |
| EP | 0528891 | B1 | 7/2000 |
| EP | 1196550 | A2 | 4/2002 |
| EP | 1439792 | A1 | 7/2004 |
| EP | 1442765 | A1 | 8/2004 |
| EP | 1462065 | A2 | 9/2004 |
| EP | 1061983 | B1 | 11/2004 |
| EP | 1493397 | A1 | 1/2005 |
| EP | 1506039 | A1 | 2/2005 |
| EP | 0935482 | B1 | 5/2005 |
| EP | 1011495 | B1 | 11/2005 |
| EP | 1796568 | A1 | 6/2007 |
| EP | 1207797 | B1 | 2/2008 |
| EP | 1406685 | B1 | 6/2008 |
| EP | 1424970 | B1 | 12/2008 |
| EP | 2280741 | A1 | 2/2011 |
| EP | 2381829 | A1 | 11/2011 |

(56) References Cited

FOREIGN PATENT DOCUMENTS

| | | | |
|---|---|---|---|
| EP | 2413833 | A1 | 2/2012 |
| EP | 2488251 | A2 | 8/2012 |
| EP | 2642937 | A2 | 10/2013 |
| EP | 1791485 | B1 | 12/2014 |
| EP | 2373241 | B1 | 1/2015 |
| EP | 1962710 | B1 | 8/2015 |
| EP | 1962708 | B1 | 9/2015 |
| EP | 1962945 | B1 | 4/2016 |
| EP | 3143124 | A1 | 3/2017 |
| EP | 3852868 | A1 | 7/2021 |
| ES | 2300272 | | 6/2008 |
| ES | 2315493 | | 4/2009 |
| JP | 2001510702 | A | 8/2001 |
| JP | 2003505072 | A | 2/2003 |
| JP | 2003506064 | A | 2/2003 |
| JP | 2004203224 | A | 7/2004 |
| JP | 2004525726 | A | 8/2004 |
| JP | 2004303590 | A | 10/2004 |
| JP | 2005501596 | A | 1/2005 |
| JP | 2005526579 | A | 9/2005 |
| JP | 2008508946 | A | 3/2008 |
| JP | 4252316 | B2 | 4/2009 |
| JP | 2009518130 | A | 5/2009 |
| JP | 2009518150 | A | 5/2009 |
| JP | 2009518151 | A | 5/2009 |
| JP | 2009532077 | A | 9/2009 |
| JP | 2010503496 | A | 2/2010 |
| JP | 2011137025 | | 7/2011 |
| JP | 2011137025 | A | 7/2011 |
| JP | 2012510332 | A | 5/2012 |
| JP | 2012515018 | A | 7/2012 |
| JP | 2012521863 | A | 9/2012 |
| JP | 2014501574 | A | 1/2014 |
| JP | 2017518805 | A | 7/2017 |
| JP | 6594901 | B2 | 10/2019 |
| JP | 2019193668 | A | 11/2019 |
| JP | 7051188 | B2 | 4/2022 |
| KR | 101034682 | A | 5/2011 |
| WO | 9104014 | | 4/1991 |
| WO | 9634571 | | 11/1996 |
| WO | 9639531 | A | 12/1996 |
| WO | 9810745 | | 3/1998 |
| WO | 9814238 | A | 4/1998 |
| WO | 9901076 | | 1/1999 |
| WO | 9904710 | | 2/1999 |
| WO | 0020554 | A | 4/2000 |
| WO | 0107583 | A | 2/2001 |
| WO | 0107584 | A | 2/2001 |
| WO | 0107585 | A | 2/2001 |
| WO | 0110319 | A | 2/2001 |
| WO | 0148153 | A | 7/2001 |
| WO | 2001048153 | A1 | 7/2001 |
| WO | 0170114 | A1 | 9/2001 |
| WO | 0181533 | A | 11/2001 |
| WO | 02078527 | A | 10/2002 |
| WO | 02089686 | A | 11/2002 |
| WO | 02100459 | A | 12/2002 |
| WO | 2003020144 | A1 | 3/2003 |
| WO | 2003047684 | A2 | 6/2003 |
| WO | 03099382 | A | 12/2003 |
| WO | 2004037341 | A2 | 5/2004 |
| WO | 2004080347 | A2 | 9/2004 |
| WO | 2005065284 | A | 7/2005 |
| WO | 2006017666 | A2 | 2/2006 |
| WO | 2006031541 | A1 | 3/2006 |
| WO | 2006130194 | A2 | 12/2006 |
| WO | 2007067628 | A1 | 6/2007 |
| WO | 2007067937 | A2 | 6/2007 |
| WO | 2007067938 | A2 | 6/2007 |
| WO | 2007067939 | A2 | 6/2007 |
| WO | 2007067940 | A2 | 6/2007 |
| WO | 2007067941 | A2 | 6/2007 |
| WO | 2007067943 | A2 | 6/2007 |
| WO | 2007070361 | A2 | 6/2007 |
| WO | 2007100727 | A2 | 9/2007 |
| WO | 2007123690 | A2 | 11/2007 |
| WO | 2008063195 | A1 | 5/2008 |
| WO | 2008034103 | A3 | 11/2008 |
| WO | 2009046176 | A1 | 4/2009 |
| WO | 2007137303 | | 7/2009 |
| WO | 2009134876 | A | 11/2009 |
| WO | 2009135070 | A1 | 11/2009 |
| WO | 2009137800 | A2 | 11/2009 |
| WO | 2010064154 | A1 | 6/2010 |
| WO | 2010080974 | A1 | 7/2010 |
| WO | 2010117806 | A1 | 10/2010 |
| WO | 2010118387 | A | 10/2010 |
| WO | 2010132472 | A1 | 11/2010 |
| WO | 2010151277 | A | 12/2010 |
| WO | 2011047387 | A | 4/2011 |
| WO | 2011062653 | A1 | 5/2011 |
| WO | 2011072221 | A1 | 6/2011 |
| WO | 2012051433 | A2 | 4/2012 |
| WO | 2012071526 | A | 5/2012 |
| WO | 2012071526 | A2 | 5/2012 |
| WO | 2012088149 | A | 6/2012 |
| WO | 2015175570 | A1 | 11/2015 |
| WO | 2016100325 | A1 | 6/2016 |
| WO | 2016164930 | A1 | 10/2016 |
| WO | 2017117418 | A1 | 7/2017 |
| WO | 2020061192 | A1 | 3/2020 |
| WO | 2022066768 | A1 | 3/2022 |
| WO | 2023172773 | A1 | 9/2023 |
| WO | 2024081749 | A2 | 4/2024 |

OTHER PUBLICATIONS

Van Den Bos, W. et al., "MRI and contrast-enhanced ultrasound imaging for evaluation of focal irreversible electroporation treatment: results from a phase i-ii study in patients undergoing ire followed by radical prostatectomy," European radiology, vol. 26, No. 7, pp. 2252-2260, 2016.

Verbridge et al., "Oxygen-Controlled Three-Dimensional Cultures to Analyze Tumor Angiogenesis." Tissue Engineering, Part A vol. 16, pp. 2133-2141 (2010).

Verma, A. et al., "Primer on Pulsed Electrical Field Ablation: Understanding the Benefits and Limitations," Circ. Arrhythmia Electrophysiol., No. September, pp. 1-16, 2021, 16 pages.

Vernier, P.T., et al., "Nanoelectropulse-driven membrane perturbation and small molecule permeabilization", Bmc Cell Biology, 7 (2006).

Vidamed, Inc., Transurethral Needle Ablation (TUNA): Highlights from Worldwide Clinical Studies, Vidamed's Office TUNA System, 2001.

Vižintin, A. et al., "Effect of interphase and interpulse delay in high-frequency irreversible electroporation pulses on cell survival, membrane permeabilization and electrode material release," Bioelectrochemistry, vol. 134, Aug. 2020, 14 pages.

Voyer, D., A. Silve, L. M. Mir, R. Scorretti, and C. Poignard, "Dynamical modeling of tissue electroporation," Bioelectrochemistry, vol. 119, pp. 98-110, 2018.

Wandel, A. et al. "Optimizing Irreversible Electroporation Ablation with a Bipolar Electrode," Journal of Vascular and Interventional Radiology, vol. 27, Issue 9, 1441-1450.e2, 2016.

Wasson, Elisa M. et al. The Feasibility of Enhancing Susceptibility of Glioblastoma Cells to IRE Using a Calcium Adjuvant. Annals of Biomedical Engineering, vol. 45, No. 11, Nov. 2017 pp. 2535-2547.

Weaver et al., "A brief overview of electroporation pulse strength-duration space: A region where additional intracellular effects are expected." Bioelectrochemistry vol. 87, pp. 236-243 (2012).

Weaver, Electroporation: A General Phenomenon for Manipulating Cells and Tissues, Journal of Cellular Biochemistry, 51: 426-435, 1993.

Weaver, et al., Theory of Electroporation: A Review, Bioelectrochemistry and Bioenergetics, vol. 41, pp. 136-160, 1996.

Weaver, J. C., Electroporation of biological membranes from multicellular to nano scales, IEEE Trns. Dielectr. Electr. Insul. 10, 754-768 (2003).

(56) References Cited

OTHER PUBLICATIONS

Weaver, J.C., "Electroporation of cells and tissues", IEEE Transactions on Plasma Science, 28(1): p. 24-33 (2000).
Weisstein: Cassini Ovals. From MathWorld—A. Wolfram Web Resource; Apr. 30, 2010; http://mathworld.wolfram.com/ (updated May 18, 2011).
Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015 ; 38(1): 182-190. doi:10.1007/s00270-014-0905-2.
Yang et al., "Dielectric properties of human leukocyte subpopulations determined by electrorotation as a cell separation criterion." Biophysical Journal, vol. 76, pp. 3307-3314 (1999).
Yao et al., "Study of transmembrane potentials of inner and outer membranes induced by pulsed-electric-field model and simulation." IEEE Trans Plasma Sci, 2007. 35(5): p. 1541-1549.
Yarmush, M. L. et al., "Electroporation-Based Technologies for Medicine: Principles, Applications, and Challenges," Annu. Rev. Biomed. Eng., vol. 16, No. 1, 295-320, 2014, 29 pages.
Zhang, Y., et al., MR imaging to assess immediate response to irreversible electroporation for targeted ablation of liver tissues: preclinical feasibility studies in a rodent model. Radiology, 2010. 256(2): p. 424-32.
Zhao, J. et al. "Irreversible electroporation reverses resistance to immune checkpoint blockade in pancreatic cancer", Nature Communications (2019) 10:899, 14 pages.
Zhao, Y. et al., "Characterization of conductivity changes during high-frequency irreversible electroporation for treatment planning," IEEE Transactions on Biomedical Engineering, vol. 65, No. 8, pp. 1810-1819, 2017.
Zimmermann, et al., Dielectric Breakdown of Cell Membranes, Biophysical Journal, vol. 14, No. 11, pp. 881-899, 1974.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.
Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp. 894-899.
Pending U.S. Appl. No. 18/100,835, Second Preliminary Amendment filed Feb. 6, 2023, 6 pages.
Pending U.S. Appl. No. 18/120,158, Preliminary Amendment dated Mar. 13, 2023, 195 pages.
Pending U.S. Appl. No. 18/123,719, Preliminary Amendment dated Jun. 6, 2023, 6 pages.
Pending U.S. Appl. No. 18/130,330, Preliminary Amendment dated Jun. 20, 2023, 8 pages.
Pending U.S. Appl. No. 18/348,605, Preliminary Amendment dated Oct. 31, 2023, 7 pages.
Pending U.S. Appl. No. 18/502,967, Preliminary Amendment filed Nov. 6, 2023, 6 pages.
Pending Application No. 19861489.3 Extended European Search Report dated May 16, 2022 (8 pages).
Pending Application No. 19861489.3 Response to Communication pursuant to Rules 161(2) and 162 EPC, filed Nov. 16, 2021, 7 pages.
Pending Application No. 19861489.3 Response to May 16, 2022 Extended European Search Report, dated Dec. 13, 2022, 136 pages.
Pending Application No. AU 2009243079, First Examination Report, Jan. 24, 2014, 4 pages.
Pending Application No. AU 2009243079, Voluntary Amendment filed Dec. 6, 2010, 35 pages.
Pending Application No. AU 2015259303, Certificate of Grant dated Feb. 10, 2022, 1 page.
Pending Application No. AU 2015259303, First Examination Report dated Oct. 26, 2020, 6 pages.
Pending Application No. AU 2015259303, Notice of Acceptance and Allowed Claims, dated Oct. 15, 2021, 7 pages.
Pending Application No. AU 2015259303, Response to First Examination Report dated Sep. 20, 2021, 126 pages.
Pending Application No. CA 2,722,296 Examination Report dated Apr. 2, 2015, 6 pages.
Pending Application No. CN 201580025135.6 English translation of Apr. 29, 2020 Office action, 7 pages.
Pending Application No. CN 201580025135.6 English translation of Sep. 25, 2019 Office action.
Pending Application No. CN 201580025135.6 Preliminary Amendment filed with application Nov. 14, 2016.
Pending Application No. CN 201580025135.6 Response to Sep. 25, 2019 Office action, filed Feb. 10, 2020, English language version and original document.
Pending Application No. CN 201580025135.6, First Office Action, dated Sep. 25, 2019 (Chinese and English Versions, each 6 pages).
Pending Application No. CN 201580025135.6, Response to First Office Action, Feb. 7, 2020, (Chinese Vrsion, 13 pages, and English Version, 10 pages).
Pending Application No. CN 201580025135.6, Second Office Action, dated Apr. 29, 2020 (Chinese Version, 4 pages, and English Version, 7 pages).
Pending Application No. CN 202011281572.3, Amendment filed Sep. 8, 2021 (16 pages) with English Version of the Amended Claims (7 pages).
Pending Application No. EP 09739678.2 Extended European Search Report dated May 11, 2012, 7 pages.
Pending Application No. EP 09739678.2, Communication pursuant to Rule 94.3, Apr. 16, 2014, 3 pages.
Pending Application No. EP 09739678.2, Office Action dated Apr. 16, 2014, 3 pages.
Pending Application No. EP 09739678.2, Response to Extended European Search Report and Communication pursuant to Rules 70(2) and 70a(2) EPC, dated Dec. 10, 2012.
Pending Application No. EP 10824248.8, Extended Search Report (Jan. 20, 2014), 6 pages.
Pending Application No. EP 10824248.8, Invitation Pursuant to rule 62a(1) EPC (Sep. 25, 2013), 2 pages.
Pending Application No. EP 10824248.8, Communication Pursuant to Rule 70(2) dated Feb. 6, 2014, 1 page.
Pending Application No. EP 10824248.8, Response to Invitation Pursuant to rule 62a(1) EPC (Sep. 25, 2013), Response filed Nov. 18, 2013.
Pending Application No. EP 11842994.3, Communication Pursuant to Rules 70(2) and 70a(2) EPC dated Apr. 28, 2014, 1 page.
Pending Application No. EP 11842994.3, Extended European Search Report dated Apr. 9, 2014, 34 pages.
Pending Application No. EP 15793361.5, Claim amendment filed Jul. 18, 2018, 13 pages.
Pending Application No. EP 15793361.5, Communication Pursuant to Article 94(3) EPC, dated Apr. 4, 2023, 4 pages.
Pending Application No. EP 15793361.5, Communication Pursuant to Article 94(3) EPC, dated May 3, 2021, 4 pages.
Pending Application No. EP 15793361.5, European Search Report dated Dec. 4, 2017, 9 pages.
Pending Application No. EP 15793361.5, Response to Apr. 4, 2023 Communication Pursuant to Article 94(3) EPC, dated Oct. 16, 2023, 13 pages.
Pending Application No. EP 15793361.5, Response to May 3, 2021 Communication Pursuant to Article 94(3) EPC, dated Nov. 12, 2021, 12 pages.
Pending Application No. JP 2013-541050, Voluntary Amendment filed Oct. 29, 2013, 4 pages (with English Version of the Claims, 2 pages).
Pending Application No. JP 2016-567747 Amendment filed Jul. 18, 2019, 7 pgs.
Pending Application No. JP 2016-567747 English translation of amended claims filed Jul. 18, 2019, 6 pgs.
Pending Application No. JP 2016-567747 , First Office Action (Translation) dated Feb. 21, 2019, 5 pages.
Pending Application No. JP 2016-567747 , First Office Action dated Feb. 21, 2019, 4 pages.
Pending Application No. JP 2016-567747, Decision to Grant with English Version of allowed claims, 9 pages.

(56) References Cited

OTHER PUBLICATIONS

Pending Application No. JP 2019-133057, amended claims (English language version) filed Aug. 14, 2019, 5 pages.
Pending Application No. JP 2019-133057, Office Action dated Sep. 1, 2021, 3 pages (and English translation, 4 pages).
Pending Application No. JP 2019-133057, Office Action dated Sep. 14, 2020, 5 pages (and English translation, 6 pages).
Pending Application No. JP 2019-133057, Request for Amendment and Appeal filed Dec. 23, 2021 (8 pages) with English Translation of the Amended Claims (2 pages).
(Arena, Christopher B. et al.) Co-pending U.S. Appl. No. 15/186,653, filed Jun. 20, 2016, and published as U.S. Publication No. 2016/0287314 on Oct. 6, 2016, Specification, Claims, Figures.
(Arena, Christopher B. et al.) Co-pending U.S. Appl. No. 16/372,520, filed Apr. 2, 2019, which published as 20190223938 on Jul. 25, 2019, Specification, Claims, Figures.
(Arena, Christopher B. et al.) Co-Pending Application No. PCT/US11/66239, filed Dec. 20, 2011, Specification, Claims, Figures.
(Arena, Christopher B. et al.) Co-Pending U.S. Appl. No. 13/332,133, filed Dec. 20, 2011 and published as U.S. Publication No. 2012/0109122 on May 3, 2012, Specification, Claims, Figures.
(Aycock, Kenneth N. et al.) Co-pending U.S. Appl. No. 17/535,742, filed Nov. 26, 2021, Specification, Claims, and Figures.
(Davalos, Rafael et al.) Co-Pending Application No. PCT/US21/51551, filed Sep. 22, 2021, Specification, Claims, Figures.
(Davalos, Rafael et al.) Co-pending U.S. Appl. No. 10/571,162, filed Oct. 18, 2006 (published as 2007/0043345 on Feb. 22, 2007), Specification, Figures, Claims.
(Davalos, Rafael et al.) Co-Pending U.S. Appl. No. 12/757,901, filed Apr. 9, 2010, Specification, Claims, Figures.
(Davalos, Rafael et al.) Co-Pending Application No. PCT/US04/43477, filed Dec. 21, 2004, Specification, Claims, Figures.
(Davalos, Rafael et al.) Co-Pending Application No. PCT/US23/15118, filed Mar. 13, 2023, Specification, Claims, Figures.
(Davalos, Rafael et al.) Co-Pending Application No. PCT/US23/76626, filed Oct. 11, 2023, Specification, Claims, Figures.
(Davalos, Rafael V. et al) Co-Pending Application No. PCT/US10/53077, filed Oct. 18, 2010, Specification, Claims, Figures.
(Davalos, Rafael V. et al.) Co-Pending U.S. Appl. No. 12/491,151, filed Jun. 24, 2009, and published as U.S. Publication No. 2010/0030211 on Feb. 4, 2010, Specification, Claims, Figures.
(Davalos, Rafael V. et al.) Co-Pending U.S. Appl. No. 12/609,779, filed Oct. 30, 2009, and published as U.S. Publication No. 2010/0331758 on Dec. 30, 2010, Specification, Claims, Figures.
(Davalos, Rafael V. et al.) Co-Pending U.S. Appl. No. 13/919,640, filed Jun. 17, 2013, and published as U.S. Publication No. 2013/0281968 on Oct. 24, 2013, Specification, Claims, Figures.
(Davalos, Rafael V. et al.) Co-Pending U.S. Appl. No. 14/686,380, filed Apr. 14, 2015 and Published as US 2015/0289923 on Oct. 15, 2015, Specification, Claims, Figures.
(Davalos, Rafael V. et al.) Co-pending U.S. Appl. No. 15/424,335, filed Feb. 3, 2017, and published as U.S. Publication No. 2017/0189579 on Jul. 6, 2017, Specification, Claims, Figures.
(Davalos, Rafael V. et al.) Co-pending U.S. Appl. No. 15/536,333, filed Jun. 15, 2017, and published as U.S. Publication No. 2017/0360326 on Dec. 21, 2017, Specification, Claims, Figures.
(Davalos, Rafael V. et al.) Co-pending U.S. Appl. No. 15/881,414, filed Jan. 26, 2018, and published as U.S. Publication No. 2018/0161086 on Jun. 14, 2018, Specification, Claims, Figures.
(Davalos, Rafael V. et al.) Co-pending U.S. Appl. No. 16/177,745, filed Nov. 1, 2018, and published as U.S. Publication No. 2019/0069945 on Mar. 7, 2019, Specification, Claims, Figures.
(Davalos, Rafael V. et al.) Co-pending U.S. Appl. No. 16/232,962 filed Dec. 26, 2018, and published as U.S. Publication No. 2019/0133671 on May 9, 2019, Specification, Claims, Figures.
(Davalos, Rafael V. et al.) Co-pending U.S. Appl. No. 16/275,429, filed Feb. 14, 2019, which published as 2019/0175260 on Jun. 13, 2019, Specification, Claims, Figures.
(Davalos, Rafael V. et al.) Co-pending U.S. Appl. No. 16/352,759, filed Mar. 13, 2019, Specification, Claims, Figures.
(Davalos, Rafael V. et al.) Co-pending U.S. Appl. No. 16/535,451, filed Aug. 8, 2019, and Published as U.S. Publication No. 2019/0376055 on Dec. 12, 2019, Specification, Claims, Figures.
(Davalos, Rafael V. et al.) Co-pending U.S. Appl. No. 16/865,031, filed May 1, 2020, Specification, Claims, Figures.
(Davalos, Rafael V. et al.) Co-pending U.S. Appl. No. 17/069,359, filed Oct. 13, 2020, Specification, Claims, Drawings.
(Davalos, Rafael V. et al.) Co-pending U.S. Appl. No. 17/172,731, filed Feb. 10, 2021, Specification, Claims, Figures.
(Davalos, Rafael V. et al.) Co-pending U.S. Appl. No. 17/277,662, filed Mar. 18, 2021, Specification, Claims, Figures.
(Davalos, Rafael V. et al.) Co-Pending U.S. Appl. No. 18/027,824, filed Mar. 22, 2023, Specification, Claims, and Figures.
(Davalos, Rafael V. et al.) Co-Pending U.S. Appl. No. 18/130,330, filed Apr. 3, 2023, Specification, Claims, Figures.
(Davalos, Rafael V. et al.) Co-pending U.S. Appl. No. 18/348,605, filed Jul. 7, 2023, Specification, Claims, Drawings.
(Davalos, Rafael V. et al.) Co-pending U.S. Appl. No. 18/402,231, filed Jan. 2, 2024, Specification, Claims, Figures.
(Davalos, Rafael V. et al.) Co-pending U.S. Appl. No. 18/404,473, filed Jan. 4, 2024, Specification, Claims, Figures.
(Davalos, Rafael V. et al.) Co-pending Application No. 19861489.3 filed Apr. 16, 2021, Specification, figures (See PCT/US19/51731), and claims (3 pages).
(Davalos, Rafael V. et al.) Co-Pending Application No. AU 2009243079, filed Apr. 29, 2009 (see PCT/US2009/042100 for documents as filed), Specification, Claims, Figures.
(Davalos, Rafael V. et al.) Co-Pending Application No. PCT/US09/62806, filed Oct. 30, 2009, Specification, Claims, Figures.
(Davalos, Rafael V. et al.) Co-Pending Application No. PCT/US10/30629, filed Apr. 9, 2010, Specification, Claims, Figures.
(Davalos, Rafael V. et al.) Co-pending application No. PCT/US19/51731 filed Sep. 18, 2019, Specification, Claims, Figures.
(Davalos, Rafael V. et al.) Co-Pending U.S. Appl. No. 14/017,210, filed Sep. 3, 2013, and published as U.S. Publication No. 2014/0039489 on Feb. 6, 2014, Specification, Claims, Figures.
(Davalos, Rafael V. et al.) Co-Pending U.S. Appl. No. 14/627,046, filed Feb. 20, 2015, and published as U.S. Publication No. 2015/0164584 on Jun. 18, 2015, Specification, Claims, Figures.
(Davalos, Rafael V. et al.) Co-Pending International Application No. PCT/US15/65792, filed Dec. 15, 2015, Specification, Claims, Drawings.
(Davalos, Rafael V.) Co-Pending U.S. Appl. No. 12/432,295, filed Apr. 29, 2009, and published as U.S. Publication No. 2009/0269317-A1 on Oct. 29, 2009, Specification, Figures, Claims.
(Davalos, Rafael V.) Co-pending U.S. Appl. No. 15/423,986, filed Feb. 3, 2017, and published as U.S. Publication No. 2017/0209620 on Jul. 27, 2017, Specification, Claims, Figures.
(Davalos, Rafael V.) Co-Pending Application No. CA 2,722,296, filed Apr. 29, 2009, Amended Claims (7 pages), Specification, Figures (See PCT/US2009/042100 for Specification and figures as filed).
(Davalos, Rafael V.) Co-Pending Application No. EP 09739678.2 filed Apr. 29, 2009, Amended Claims (3 pages), Specification and Figures (See PCT/US2009/042100).
(Davalos, Rafael V.) Co-Pending Application No. PCT/US09/42100, filed Apr. 29, 2009, Specification, Claims, Figures.
(Garcia, Paulo A. et al.) Co-Pending U.S. Appl. No. 14/012,832, filed Aug. 28, 2013, and published as U.S. Publication No. 2013/0345697 on Dec. 26, 2013, Specification, Claims, Figures.
(Garcia, Paulo A. et al.) Co-Pending U.S. Appl. No. 14/558,631, filed Dec. 2, 2014, and published as U.S. Publication No. 2015/0088120 on Mar. 26, 2015, Specification, Claims, Figures.
(Garcia, Paulo A. et al.) Co-Pending U.S. Appl. No. 15/011,752, filed Feb. 1, 2016, and published as U.S. Publication No. 2016/0143698 on May 26, 2016, Specification, Claims, Figures.
(Garcia, Paulo A. et al.) Co-Pending U.S. Appl. No. 16/655,845, filed Oct. 17, 2019, Specification, Claims, Figures.
(Garcia, Paulo A. et al.) Co-Pending U.S. Appl. No. 18/100,835, filed Jan. 24, 2023, Specification, Claims, Figures.
(Garcia, Paulo A. et al.) Co-pending U.S. Appl. No. 16/152,743, filed Oct. 5, 2018, Specification, Claims, Figures.

(56) References Cited

OTHER PUBLICATIONS (Garcia, Paulo A. et al.) Co-pending U.S. Appl. No. 17/591,992, filed Feb. 3, 2022, Specification, Claims, Figures.
(Latouche, Eduardo et al.) Co-pending U.S. Appl. No. 16/210,771, filed Dec. 5, 2018, and which published as US Patent Publication No. 2019/0232048 on Aug. 1, 2019, Specification, Claims, Figures.
(Lorenzo, Melvin F. et al.) Co-pending U.S. Appl. No. 16/938,778, filed Jul. 24, 2020, Specification, Claims, Figures.
(Mahajan, Roop L. et al.) Co-Pending U.S. Appl. No. 13/958,152, filed Aug. 2, 2013, Specification, Claims, Figures.
(Neal, Robert E. et al.) Co-Pending U.S. Appl. No. 12/906,923, filed Oct. 18, 2010, Specification, Claims, Figures.
(Neal, Robert E. et al.) Co-Pending U.S. Appl. No. 14/808,679, filed Jul. 24, 2015 and Published as U.S. Publication No. 2015/0327944 on Nov. 19, 2015, Specification, Claims, Figures.
(Neal, Robert E. et al.) Co-pending U.S. Appl. No. 16/375,878, filed Apr. 5, 2019, which published on Aug. 1, 2019 as US 2019-0233809 A1, Specification, Claims, Figures.
(Neal, Robert E. et al.) Co-pending U.S. Appl. No. 16/404,392, filed May 6, 2019, and published as U.S. Publication No. 2019/0256839 on Aug. 22, 2019, Specification, Claims, Figures.
(Neal, Robert E. et al.) Co-pending U.S. Appl. No. 16/865,772, filed May 4, 2020, Specification, Claims, Figures.
(Neal, Robert E. et al.) Co-pending U.S. Appl. No. 18/120,158, filed Mar. 10, 2023, Specification, Claims, Figures.
(Neal, Robert E. et al.) Co-pending U.S. Appl. No. 18/502,967, filed Nov. 6, 2023, Specification, Claims, Figures.
(Neal, Robert E. et al.) Co-Pending U.S. Appl. No. 13/550,307, filed Jul. 16, 2012, and published as U.S. Publication No. 2013/0184702 on Jul. 18, 2013, Specification, Claims, Figures.
(Neal, Robert E. et al.) Co-Pending U.S. Appl. No. 14/940,863, filed Nov. 13, 2015 and Published as US 2016/0066977 on Mar. 10, 2016, Specification, Claims, Figures.
(Neal, Robert et al.) Co-pending U.S. Appl. No. 16/280,511, filed Feb. 20, 2019, and published as U.S. Publication No. 2019/0175248 on Jun. 13, 2019, Specification, Claims, Figures.
(Neal, Robert et al.) Co-pending U.S. Appl. No. 17/338,960, filed Jun. 4, 2021, Specification, Claims, Figures.
(Neal, Robert et al.) Co-Pending Application No. EP 10824248.8, filed May 9, 2012, Amended Claims (3 pages), Specification and Figures (See PCT/US10/53077).
(O'Brien, Timothy J. et al.) Co-Pending U.S. Appl. No. 16/915,760, filed Jun. 29, 2020, Specification, Claims, Figures.
(O'Brien, Timothy J. et al.) Co-Pending U.S. Appl. No. 17/152,379, filed Jan. 19, 2021, Specification, Claims, Figures.
(Pearson, Robert M. et al.) Co-pending Application No. PCT/US2010/029243, filed Mar. 30, 2010, published as WO 2010/117806 on Oct. 14, 2010, Specification, Claims, Figures.
(Pearson, Robert M. et al.) Co-pending U.S. Appl. No. 12/751,826, filed Mar. 31, 2010 (published as 2010/0250209 on Sep. 30, 2010), Specification, Claims, Figures.
(Pearson, Robert M. et al.) Co-pending U.S. Appl. No. 12/751,854, filed Mar. 31, 2010 (published as 2010/0249771 on Sep. 30, 2010), Specification, Claims, Figures.
(Sano, Michael B. et al.) Co-Pending Application No. PCT/US2015/030429, Filed May 12, 2015, Published on Nov. 19, 2015 as WO 2015/175570, Specification, Claims, Figures.
(Sano, Michael B. et al.) Co-Pending U.S. Appl. No. 13/989,175, filed May 23, 2013, and published as U.S. Publication No. 2013/0253415 on Sep. 26, 2013, Specification, Claims, Figures.
(Sano, Michael B. et al.) Co-Pending U.S. Appl. No. 15/310,114, filed Nov. 10, 2016, and published as U.S. Publication No. 2017/0266438 on Sep. 21, 2017, Specification, Claims, Figures.
(Sano, Michael B. et al.) Co-pending U.S. Appl. No. 15/843,888, filed Dec. 15, 2017, and published as U.S. Publication No. 2018/0125565 on May 10, 2018, Specification, Claims, Figures.
(Sano, Michael B. et al.) Co-pending U.S. Appl. No. 16/443,351, filed Jun. 17, 2019 (published as 20190328445 on Oct. 31, 2019), Specification, Claims, Figures.
(Sano, Michael B. et al.) Co-pending U.S. Appl. No. 16/520,901, filed Jul. 24, 2019, and published as U.S. Publication No. 2019/0351224 on Nov. 21, 2019, Specification, Claims, Figures.
(Sano, Michael B. et al.) Co-Pending U.S. Appl. No. 16/747,219, filed Jan. 20, 2020, Specification, Claims, Figures.
(Sano, Michael B. et al.) Co-pending U.S. Appl. No. 17/862,486, filed Jul. 12, 2022, Specification, Claims, Figures.
(Sano, Michael B. et al.) Co-pending U.S. Appl. No. 18/123,719, filed Mar. 20, 2023, Specification, Claims, Figures.
(Sano, Michael B. et al.) Co-Pending Application No. AU 2015259303, filed Oct. 24, 2016, Specification, Figures, Claims.
(Sano, Michael B. et al.) Co-Pending Application No. CN 201580025135.6, filed Nov. 14, 2016, Specification, Claims, Figures (Chinese language and english language versions).
(Sano, Michael B. et al.) Co-Pending Application No. CN 202011281572.3, filed Nov. 16, 2020, Specification, Claims, Figures (Chinese version, 129 pages (see also WO 2015/175570), English Version of claims, 2 pages).
(Sano, Michael B. et al.) Co-Pending Application No. EP 11842994.3, filed Jun. 24, 2013, Amended Claims (18 pages), Specification and Figures (See PCT/US11/62067).
(Sano, Michael B. et al.) Co-Pending Application No. EP 15793361.5, filed Dec. 12, 2016, Specification, Claims, Figures.
(Sano, Michael B. et al.) Co-pending application No. HK 17112121.8, filed Nov. 20, 2017 and published as Publication No. HK1238288 on Apr. 27, 2018, Specification, Claims, Figures (See PCT/US15/30429 for English Version of documents as filed).
(Sano, Michael B. et al.) Co-Pending Application No. JP 2013-541050, filed May 22, 2013, Claims, Specification, and Figures (See PCT/US11/62067 for English Version).
(Sano, Michael B. et al.) Co-Pending Application No. JP 2016-567747, filed Nov. 10, 2016, Specification, Claims, Figures (see PCT/US15/30429 for English Version of documents as filed).
(Sano, Michael B. et al.) Co-pending Application No. JP 2019-133057 filed Jul. 18, 2019, 155 pgs, Specification, Claims, Figures (See PCT/US15/30429 for English Version of documents as filed).
(Sano, Michael et al.) Co-Pending Application No. PCT/US11/62067, filed Nov. 23, 2011, Specification, Claims, Figures.
(Wasson, Elisa M. et al.) Co-pending U.S. Appl. No. 17/000,049, filed Aug. 21, 2020, Specification, Claims, Figures.
Abiror, I.G., et al., "Electric Breakdown of Bilayer Lipid-Membranes .1. Main Experimental Facts and Their Qualitative Discussion", Bioelectrochemistry and Bioenergetics, 6(1): p. 37-52 (1979).
Agerholm-Larsen, B., et al., "Preclinical Validation of Electrochemotherapy as an Effective Treatment for Brain Tumors", Cancer Research 71: 3753-3762 (2011).
Alberts et al., "Molecular Biology of the Cell," 3rd edition, Garland Science, New York, 1994, 1 page.
Alinezhadbalalami, N. et al., "Generation of Tumor-activated T cells Using Electroporation", Bioelectrochemistry 142 (2021) 107886, Jul. 13, 2021, 11 pages.
Al-Sakere et al., "Tumor ablation with irreversible electroporation," PLoS ONE, 2, e1135, 2007, 8 pages.
Amasha, et al., Quantitative Assessment of Impedance Tomography for Temperature Measurements in Microwave Hyperthermia, Clin. Phys. Physiol. Meas., 1998, Suppl. A, 49-53.
Andreason, Electroporation as a Technique for the Transfer of Macromolecules into Mammalian Cell Lines, J. Tiss. Cult. Meth., 15:56-62, 1993.
Sharma, A. , et al., "Review on Thermal Energy Storage with Phase Change Materials and Applications", Renewable Sustainable Energy Rev. 13(2), 318-345 (2009).
Sharma, et al., Poloxamer 188 Decreases Susceptibility of Artificial Lipid Membranes to Electroporation, Biophysical Journal, vol. 71, No. 6, pp. 3229-3241, Dec. 1996.
Shiina, S., et al., Percutaneous ethanol injection therapy for hepatocellular carcinoma: results in 146 patients. AJR, 1993, 160: p. 1023-8.
Szot et al., "3D in vitro bioengineered tumors based on collagen I hydrogels." Biomaterials vol. 32, pp. 7905-7912 (2011).

(56) References Cited

OTHER PUBLICATIONS

Talele, S. and P. Gaynor, "Non-linear time domain model of electropermeabilization: Effect of extracellular conductivity and applied electric field parameters", Journal of Electrostatics,66(5-6): p. 328-334 (2008).
Talele, S. and P. Gaynor, "Non-linear time domain model of electropermeabilization: Response of a single cell to an arbitrary applied electric field", Journal of Electrostatics, 65(12): p. 775-784 (2007).
Talele, S., et al., "Modelling single cell electroporation with bipolar pulse parameters and dynamic pore radii". Journal of Electrostatics, 68(3): p. 261-274 (2010).
Teissie, J. and T.Y. Tsong, "Electric-Field Induced Transient Pores in Phospholipid-Bilayer Vesicles". Biochemistry, 20(6): p. 1548-1554 (1981).
Tekle, Ephrem, R. Dean Astumian, and p. Boon Chock, Electroporation by using bipolar oscillating electric field: An improved method for DNA transfection of NIH 3T3 cells, Proc. Natl. Acad. Sci., vol. 88, pp. 4230-4234, May 1991, Biochemistry.
Thompson, et al., To determine whether the temperature of 2% lignocaine gel affects the initial discomfort which may be associated with its instillation into the male urethra, BJU International (1999), 84, 1035-1037.
Thomson et al., "Investigation of the safety of irreversible electroporation in humans," J Vasc Interv Radiol, 22, pp. 611-621, 2011.
Tibbitt et al., "Hydrogels as Extracellular Matrix Mimics for 3D Cell Culture", Jul. 2009, Biotechnol Bioeng, 103 (4),655-663.
TUNA—Suggested Local Anesthesia Guidelines, no date available.
U.S. Appl. No. 12/491,151 (U.S. Pat. No. 8,992,517), file history through Feb. 2015, 113 pages.
U.S. Appl. No. 12/609,779 (U.S. Pat. No. 8,465,484)), file history through May 2013, 100 pages.
U.S. Appl. No. 12/757,901 (U.S. Pat. No. 8,926,606), file history through Jan. 2015, 165 pages.
U.S. Appl. No. 12/906,923 (U.S. Pat. No. 9,198,733), file history through Nov. 2015, 55 pages.
U.S. Appl. No. 13/332,133 (U.S. Pat. No. 10,448,989), file history through Sep. 2019, 226 pages.
U.S. Appl. No. 13/550,307 (U.S. Pat. No. 10,702,326), file history through May 2020, 224 pages.
U.S. Appl. No. 13/919,640 (U.S. Pat. No. 8,814,860), file history through Jul. 2014, 41 pages.
U.S. Appl. No. 13/958,152, file history through Dec. 2019, 391 pages.
U.S. Appl. No. 13/989,175 (U.S. Pat. No. 9,867,652), file history through Dec. 2017, 200 pages.
U.S. Appl. No. 14/012,832 (U.S. Pat. No. 9,283,051), file history through Nov. 2015, 17 pages.
U.S. Appl. No. 14/017,210 (U.S. Pat. No. 10,245,098), file history through Jan. 2019, 294 pages.
U.S. Appl. No. 14/558,631 (U.S. Pat. No. 10,117,707), file history through Jul. 2018, 58 pages.
U.S. Appl. No. 14/627,046 (U.S. Pat. No. 10,245,105), file history through Feb. 2019, 77 pages.
U.S. Appl. No. 14/808,679 (U.S. Pat. No. 11,655,466), file history through Aug. 2022, 253 pages.
U.S. Appl. No. 14/940,863 (U.S. Pat. No. 10,238,447), file history through Oct. 2019, 23 pages.
U.S. Appl. No. 15/011,752 (U.S. Pat. No. 10,470,822), file history through Jul. 2019, 54 pages.
U.S. Appl. No. 15/186,653 (U.S. Pat. No. 10,292,755), file history through Mar. 2019, 21 pages.
U.S. Appl. No. 15/310,114 (U.S. Pat. No. 10,471,254), file history through Aug. 2019, 44 pages.
U.S. Appl. No. 15/423,986 (U.S. Pat. No. 10,286,108), file history through Jan. 2019, 124 pages.
U.S. Appl. No. 15/424,335 (U.S. Pat. No. 10,272,178), file history through Feb. 2019, 57 pages.
U.S. Appl. No. 15/536,333 (U.S. Pat. No. 10,694,972), file history through Apr. 2020, 78 pages.
U.S. Appl. No. 15/843,888 (U.S. Pat. No. 10,537,379), file history through Sep. 2019, 83 pages.
U.S. Appl. No. 15/881,414 (U.S. Pat. No. 10,154,874), file history through Nov. 2018, 43 pages.
U.S. Appl. No. 16/152,743 (U.S. Pat. No. 11,272,979), file history through Jan. 2022, 89 pages.
U.S. Appl. No. 16/177,745 (U.S. Pat. No. 10,828,085), file history through Jun. 2020, 57 pages.
U.S. Appl. No. 16/210,771 (U.S. Pat. No. 11,607,537), file history through Dec. 2022, 139 pages.
U.S. Appl. No. 16/232,962 (U.S. Pat. No. 10,828,086), file history through Jun. 2020, 44 pages.
U.S. Appl. No. 16/275,429 (U.S. Pat. No. 10,959,772), file history through Feb. 2021, 18 pages.
U.S. Appl. No. 16/280,511, file history through Aug. 2021, 31 pages.
U.S. Appl. No. 16/352,759 (U.S. Pat. No. 11,311,329), file history through Mar. 2022, 258 pages.
U.S. Appl. No. 16/372,520 (U.S. Pat. No. 11,382,681), file history through Jun. 2022, 107 pages.
U.S. Appl. No. 16/404,392 (U.S. Pat. No. 11,254,926), file history through Jan. 2022, 153 pages.
U.S. Appl. No. 16/443,351 (U.S. Pat. No. 11,638,603), file history through Mar. 2023, 114 pages.
U.S. Appl. No. 16/520,901 (U.S. Pat. No. 11,406,820), file history through May 2022, 39 pages.
U.S. Appl. No. 16/535,451 (U.S. Pat. No. 11,453,873), file history through Aug. 2022, 85 pages.
U.S. Appl. No. 16/655,845 (U.S. Pat. No. 11,607,271), file history through Jan. 2023, 68 pages.
U.S. Appl. No. 17/069,359 (U.S. Pat. No. 11,737,810), file history through Apr. 2023, 27 pages.
Gascoyne et al., "Membrane changes accompanying the induced differentiation of Friend murine erythroleukemia cells studied by dielectrophoresis." Biochimica et Biophysica Acta (BBA)-Biomembranes, vol. 1149, pp. 119-126 (1993).
Gauger, et al., A Study of Dielectric Membrane Breakdown in the Fucus Egg, J. Membrane Biol., vol. 48, No. 3, pp. 249-264, 1979.
Gawad, S., T. Sun, N. G. Green, and H. Morgan, "Impedance spectroscopy using maximum length sequences: Application to single cell analysis," Review of Scientific Instruments, vol. 78, No. 5, p. 054301, 2007.
Gehl, et al., In Vivo Electroporation of Skeletal Muscle: Threshold, Efficacy and Relation to Electric Field Distribution, Biochimica et Biphysica Acta 1428, 1999, pp. 233-240.
Gençer, et al., Electrical Impedance Tomography: Induced-Current Imaging Achieved with a Multiple Coil System, IEEE Transactions on Biomedical Engineering, vol. 43, No. 2, Feb. 1996.
Gilbert, et al., Novel Electrode Designs for Electrochemotherapy, Biochimica et Biophysica Acta 1334, 1997, pp. 9-14.
Gilbert, et al., The Use of Ultrasound Imaging for Monitoring Cryosurgery, Proceedings 6th Annual Conference, IEEE Engineering in Medicine and Biology, 107-111, 1984.
Gilbert, T. W., et al., "Decellularization of tissues and organs", Biomaterials, Elsevier Science Publishers, Barking, GB, vol. 27, No. 19, Jul. 1, 2006, pp. 3675-3683.
Gimsa et al., "Dielectric spectroscopy of single human erythrocytes at physiological ionic strength: dispersion of the cytoplasm." Biophysical Journal, vol. 71, pp. 495-506 (1996).
Glidewell, et al., The Use of Magnetic Resonance Imaging Data and the Inclusion of Anisotropic Regions in Electrical Impedance Tomography, Biomed, Sci. Instrum. 1993; 29: 251-7.
Golberg, A. and Rubinsky, B., "A statistical model for multidimensional irreversible electroporation cell death in tissue." Biomed Eng Online, 9, 13 pages, 2010.
Gothelf, et al., Electrochemotherapy: Results of Cancer Treatment Using Enhanced Delivery of Bleomycin by Electroporation, Cancer Treatment Reviews 2003: 29: 371-387.
Gowrishankar T.R., et al., "Microdosimetry for conventional and supra-electroporation in cells with organelles". Biochem Biophys Res Commun, 341(4): p. 1266-76 (2006).

(56) References Cited

OTHER PUBLICATIONS

Granot, Y., A. Ivorra, E. Maor, and B. Rubinsky, "In vivo imaging of irreversible electroporation by means of electrical impedance tomography," Physics in Medicine & Biology, vol. 54, No. 16, p. 4927, 2009.
Griffiths, et al., A Dual-Frequency Electrical Impedance Tomography System, Phys. Med. Biol., 1989, vol. 34, No. 10, pp. 1465-1476.
Griffiths, The Importance of Phase Measurement in Electrical Impedance Tomography, Phys. Med. Biol., 1987, vol. 32, No. 11, pp. 1435-1444.
Griffiths, Tissue Spectroscopy with Electrical Impedance Tomography: Computer Simulations, IEEE Transactions on Biomedical Engineering, vol. 42, No. 9, Sep. 1995.
Groen, M. H. A. et al., "In Vivo Analysis of the Origin and Characteristics of Gaseous Microemboli during Catheter-Mediated Irreversible Electroporation," Europace, 2021, 23(1), 139-146.
Guenther, E. et al., "Electrical breakdown in tissue electroporation," Biochem. Biophys. Res. Commun., vol. 467, No. 4, 736-741, Nov. 2015, 15 pages.
Gumerov, et al., The Dipole Approximation Method and Its Coupling with the Regular Boundary Element Method for Efficient Electrical Impedance Tomography, Boundary Element Technology XIII, 1999.
Hapala, Breaking the Barrier: Methods for Reversible Permeabilization of Cellular Membranes, Critical Reviews in Biotechnology, 17(2): 105-122, 1997.
Helczynska et al., "Hypoxia promotes a dedifferentiated phenotype in ductal breast carcinoma in situ." Cancer Research, vol. 63, pp. 1441-1444 (2003).
Heller, et al., Clinical Applications of Electrochemotherapy, Advanced Drug Delivery Reviews, vol. 35, pp. 119-129, 1999.
Hjouj, M. et al., "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, p. iii114.
Hjouj, M., et al., "MRI Study on Reversible and Irreversible Electroporation Induced Blood Brain Barrier Disruption", Plos One, Aug. 2012, 7:8, e42817.
Ho, et al., Electroporation of Cell Membranes: A Review, Critical Reviews in Biotechnology, 16(4): 349-362, 1996.
Hoejholt, K. L. et al. Calcium electroporation and electrochemotherapy for cancer treatment: Importance of cell membrane composition investigated by lipidomics, calorimetry and in vitro efficacy. Scientific Reports (Mar. 18, 2019) 9:4758, p. 1-12.
Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical Bi, pp. 512-519, 1999.
Hu, Q., et al., "Simulations of transient membrane behavior in cells subjected to a high-intensity ultrashort electric pulse", Physical Review E, 71(3) (2005).
Huang, et al., Micro-Electroporation: Improving the Efficiency and Understanding of Electrical Permeabilization of Cells, Biomedical Microdevices, vol. 2, pp. 145-150, 1999.
Hughes, et al., An Analysis of Studies Comparing Electrical Impedance Tomography with X-Ray Videofluoroscopy in the Assessment of Swallowing, Physiol. Meas. 15, 1994, pp. A199-A209.
Ibey et al., "Selective cytotoxicity of intense nanosecond-duration electric pulses in mammalian cells." Biochimica Et Biophysica Acta-General Subjects, vol. 1800, pp. 1210-1219 (2010).
Issa, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998.
Ivanusa, et al., MRI Macromolecular Contrast Agents as Indicators of Changed Tumor Blood Flow, Radiol. Oncol. 2001; 35(2): 139-47.
Ivey, J. W., E. L. Latouche, M. B. Sano, J. H. Rossmeisl, R. V. Davalos, and S. S. Verbridge, "Targeted cellular ablation based on the morphology of malignant cells," Sci. Rep., vol. 5, pp. 1-17, 2015.
Ivorra et al., "In vivo electric impedance measurements during and after electroporation of rat live." Bioelectrochemistry, vol. 70, pp. 287-295 (2007).
Ivorra et al., "In vivo electrical conductivity measurements during and after tumor electroporation: conductivity changes reflect the treatment outcome." Physics in Medicine and Biology, vol. 54, pp. 5949-5963 (2009).
Ivorra, "Bioimpedance monitoring for physicians: an overview." Biomedical Applications Group, 35 pages (2002).
Ivorra, A., ed. "Tissue Electroporation as a Bioelectric Phenomenon: Basic Concepts. Irreversible Electroporation", ed. B. Rubinsky., Springer Berlin Heidelberg. 23-61 (2010).
Jarm et al., "Antivascular effects of electrochemotherapy: implications in treatment of bleeding metastases." Expert Rev Anticancer Ther. vol. 10, pp. 729-746 (2010).
Jaroszeski, et al., In Vivo Gene Delivery by Electroporation, Advanced Drug Delivery Review, vol. 35, pp. 131-137, 1999.
Jensen et al., "Tumor volume in subcutaneous mouse xenografts measured by microCT is more accurate and reproducible than determined by 18FFDG-microPET or external caliper." BMC medical Imaging vol. 8:16, 9 Pages (2008).
Jordan, D.W., et al., "Effect of pulsed, high-power radiofrequency radiation on electroporation of mammalian cells". Ieee Transactions on Plasma Science, 32(4): p. 1573-1578 (2004).
Jossinet et al., Electrical Impedance Endo-Tomography: Imaging Tissue From Inside, IEEE Transactions on Medical Imaging, vol. 21, No. 6, Jun. 2002, pp. 560-565.
Katsuki, S., et al., "Biological effects of narrow band pulsed electric fields", Ieee Transactions on Dielectrics and Electrical Insulation,. 14(3): p. 663-668 (2007).
Kingham et al., "Ablation of perivascular hepatic malignant tumors with irreversible electroporation." Journal of the American College of Surgeons, 2012. 215(3), p. 379-387.
Kinosita and Tsong, "Formation and resealing of pores of controlled sizes in human erythrocyte membrane." Nature, vol. 268 (1977) pp. 438-441.
Kinosita and Tsong, "Voltage-induced pore formation and hemolysis of human erythrocytes." Biochimica et Biophysica Acta (BBA)-Biomembranes, 471 (1977) pp. 227-242.
Kinosita et al., "Electroporation of cell membrane visualized under a pulsed-laser fluorescence microscope." Biophysical Journal, vol. 53, pp. 1015-1019 (1988).
Kinosita, et al., Hemolysis of Human Erythrocytes by a Transient Electric Field, Proc. Natl. Acad. Sci. USA, vol. 74, No. 5, pp. 1923-1927, 1977.
Kirson et al., "Alternating electric fields arrest cell proliferation in animal tumor models and human brain tumors." Proceedings of the National Academy of Sciences vol. 104, pp. 10152-10157 (2007).
Kolb, J.F., et al., "Nanosecond pulsed electric field generators for the study of subcellular effects", Bioelectromagnetics, 27(3): p. 172-187 (2006).
Kotnik and Miklavcic, "Theoretical evaluation of voltage inducement on internal membranes of biological cells exposed to electric fields." Biophysical Journal, vol. 90(2), pp. 480-491 (2006).
Kotnik et al., "Sensitivity of transmembrane voltage induced by applied electric fields—A theoretical analysis", Bioelectrochemistry and Bioenergetics,vol. 43, Issue 2, 1997, pp. 285-291.
Kotnik, T. and D. Miklavcic, "Theoretical evaluation of the distributed power dissipation in biological cells exposed to electric fields", Bioelectromagnetics, 21(5): p. 385-394 (2000).
Kotnik, T., et al., "Cell membrane electropermeabilization by symmetrical bipolar rectangular pulses. Part II. Reduced electrolytic contamination", Bioelectrochemistry, 54(1): p. 91-5 (2001).
Kotnik, T., et al., "Role of pulse shape in cell membrane electropermeabilization", Biochimica Et Biophysica Acta—Biomembranes, 1614(2): p. 193-200 (2003).
Kranjc, M., S. Kranjc, F. Bajd, G. Sersa, I. Sersa, and D. Miklavcic, "Predicting irreversible electroporation-induced tissue damage by

(56) References Cited

OTHER PUBLICATIONS means of magnetic resonance electrical impedance tomography," Scientific reports, vol. 7, No. 1, pp. 1-10, 2017.
Labeed et al., "Differences in the biophysical properties of membrane and cytoplasm of apoptotic cells revealed using dielectrophoresis." Biochimica et Biophysica Acta (BBA)—General Subjects, vol. 1760, pp. 922-929 (2006).
Lackovic, I., et al., "Three-dimensional Finite-element Analysis of Joule Heating in Electrochemotherapy and in vivo Gene Electrotransfer, Ieee Transactions on Dielectrics and Electrical Insulation", 16(5): p. 1338-1347 (2009).
Latouche, E. L., M. B. Sano, M. F. Lorenzo, R. V. Davalos, and R. C. G. Martin, "Irreversible electroporation for the ablation of pancreatic malignancies: A patient-specific methodology," J. Surg. Oncol., vol. 115, No. 6, pp. 711-717, 2017.
Laufer et al., "Electrical impedance characterization of normal and cancerous human hepatic tissue." Physiological Measurement, vol. 31, pp. 995-1009 (2010).
Lebar et al., "Inter-pulse interval between rectangular voltage pulses affects electroporation threshold of artificial lipid bilayers." IEEE Transactions on NanoBioscience, vol. 1 (2002) pp. 116-120.
Lee, E. W. et al. Advanced Hepatic Ablation Technique for Creating Complete Cell Death : Irreversible Electroporation. Radiology 255, 426-433, doi:10.1148/radiol.10090337 (2010).
Lee, E.W., et al., "Imaging guided percutaneous irreversible electroporation: ultrasound and immunohistological correlation", Technol Cancer Res Treat 6: 287-294 (2007).
Lee, R. C., D. J. Canaday, and S. M. Hammer. Transient and stable ionic permeabilization of isolated skeletal muscle cells after electrical shock. J. Burn Care Rehabil. 14:528-540, 1993.
Li, W., et al., "The Effects of Irreversible Electroporation (IRE) on Nerves" PloS One, Apr. 2011, 6(4), e18831.
Liu, et al., Measurement of Pharyngeal Transit Time by Electrical Impedance Tomography, Clin. Phys. Physiol. Meas., 1992, vol. 13, Suppl. A, pp. 197-200.
Long, G., et al., "Targeted Tissue Ablation With Nanosecond Pulses". Ieee Transactions on Biomedical Engineering, 58(8) (2011).
Lundqvist, et al., Altering the Biochemical State of Individual Cultured Cells and Organelles with Ultramicroelectrodes, Proc. Natl. Acad. Sci. USA, vol. 95, pp. 10356-10360, Sep. 1998.
Lurquin, Gene Transfer by Electroporation, Molecular Biotechnology, vol. 7, 1997.
Lynn, et al., A New Method for the Generation and Use of Focused Ultrasound in Experimental Biology, The Journal of General Physiology, vol. 26, 179-193, 1942.
Maček Lebar and Miklavčič, "Cell electropermeabilization to small molecules in vitro: control by pulse parameters." Radiology and Oncology, vol. 35(3), pp. 193-202 (2001).
Macherey, O. et al., "Asymmetric pulses in cochlear implants: Effects of pulse shape, polarity, and rate," JARO—J. Assoc. Res. Otolaryngol., vol. 7, No. 3, 253-266, 2006, 14 pages.
Mahmood, F., et al., "Diffusion-Weighted MRI for Verification of Electroporation-Based Treatments", Journal of Membrane Biology 240: 131-138 (2011).
Mahnic-Kalamiza, et al., "Educational application for visualization and analysis of electric field strength in multiple electrode electroporation," BMC Med Educ, vol. 12:102, 13 pages, 2012.
Malpica et al., "Grading ovarian serous carcinoma using a two-tier system." The American Journal of Surgical Pathology, vol. 28, pp. 496-504 (2004).
Maor et al., The Effect of Irreversible Electroporation on Blood Vessels, Tech. in Cancer Res. and Treatment, vol. 6, No. 4, Aug. 2007, pp. 307-312.
Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757.
Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.
Marszalek et al., "Schwan equation and transmembrane potential induced by alternating electric field." Biophysical Journal, vol. 58, pp. 1053-1058 (1990).
Martin, n.R.C.G., et al., "Irreversible electroporation therapy in the management of locally advanced pancreatic adenocarcinoma." Journal of the American College of Surgeons, 2012. 215(3): p. 361-369.
Martinsen, O. G. and Grimnes, S., Bioimpedance and bioelectricity basics. Academic press, 2011.
Marty, M., et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006.
McIntyre, C. C. et al., "Modeling the excitability of mammalian nerve fibers: Influence of afterpotentials on the recovery cycle," J. Neurophysiol., vol. 87, No. 2, 995-1006, 2002, 12 pages.
McNeal, D. R., "Analysis of a Model for Excitation of Myelinated Nerve," IEEE Trans. Biomed. Eng., vol. BME-23, No. 4, 329-337, 1976, 9 pages.
Mercadal, B. et al., "Avoiding nerve stimulation in irreversible electroporation: A numerical modeling study," Phys. Med. Biol., vol. 62, No. 20, 8060-8079, 2017, 28 pages.
Mercadal, Borja et al. "Dynamics of Cell Death After Conventional IRE and H-FIRE Treatments", Annals of Biomedical Engineering, vol. 48, No. 5, 2020, p. 1451-1462.
Miklavčič, D. et al., "The effect of high frequency electric pulses on muscle contractions and antitumor efficiency in vivo for a potential use in clinical electrochemotherapy," Bioelectrochemistry, vol. 65, 121-128, 2004, 8 pages.
Miklavčič, et al., A Validated Model of an in Vivo Electric Field Distribution in Tissues for Electrochemotherapy and for DNA Electrotransfer for Gene Therapy, Biochimica et Biophysica Acta 1523 (2000), pp. 73-83.
Miklavčič, et al., The Importance of Electric Field Distribution for Effective in Vivo Electroporation of Tissues, Biophysical Journal, vol. 74, May 1998, pp. 2152-2158.
Miller, L., et al., Cancer cells ablation with irreversible electroporation, Technology in Cancer Research and Treatment 4 (2005) 699-706.
Min, M., A. Giannitsis, R. Land, B. Cahill, U. Pliquett, T. Nacke, D. Frense, G. Gastrock, and D. Beckmann, "Comparison of rectangular wave excitations in broad band impedance spectroscopy for microfluidic applications," in World Congress on Medical Physics and Biomedical Engineering, Sep. 7-12, 2009, Munich, Germany. Springer, 2009, pp. 85-88.
Min, M., U. Pliquett, T. Nacke, A. Barthel, P. Annus, and R. Land, "Broadband excitation for short-time impedance spectroscopy," Physiological measurement, vol. 29, No. 6, p. S185, 2008.
Mir et al., "Mechanisms of Electrochemotherapy" Advanced Drug Delivery Reviews 35:107-118 (1999).
Mir, et al., Effective Treatment of Cutaneous and Subcutaneous Malignant Tumours by Electrochemotherapy, British Journal of Cancer, vol. 77, No. 12, pp. 2336-2342, 1998.
Mir, et al., Electrochemotherapy Potentiation of Antitumour Effect of Bleomycin by Local Electric Pulses, European Journal of Cancer, vol. 27, No. 1, pp. 68-72, 1991.
Mir, et al., Electrochemotherapy, a Novel Antitumor Treatment: First Clinical Trial, C.R. Acad. Sci. Paris, Ser. III, vol. 313, pp. 613-618, 1991.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Mir, L.M., et al., Electric Pulse-Mediated Gene Delivery to Various Animal Tissues, in Advances in Genetics, Academic Press, 2005, p. 83-114.
Pending U.S. Appl. No. 16/865,031, Notice of Allowance dated Oct. 4, 2023, 10 pages.
Pending U.S. Appl. No. 16/865,031, Preliminary Amendment filed May 1, 2020, 7 pages.
Pending U.S. Appl. No. 16/865,031, Response to May 24, 2023 Final Office Action, dated Jul. 25, 2023, 8 pages.

(56) References Cited

OTHER PUBLICATIONS

Pending U.S. Appl. No. 16/865,031, Response to Nov. 28, 2022 Non-Final Office Action, dated Feb. 27, 2023, 10 pages.
Pending U.S. Appl. No. 16/865,031, Second Preliminary Amendment, filed Sep. 17, 2021, 10 pages.
Pending U.S. Appl. No. 16/865,772, Final Office Action dated Aug. 22, 2022, 18 pages.
Pending U.S. Appl. No. 16/865,772, Final Office Action dated Aug. 4, 2023, 19 pages.
Pending U.S. Appl. No. 16/865,772, Non-Final Office Action dated Apr. 11, 2022, 16 pages.
Pending U.S. Appl. No. 16/865,772, Non-Final Office Action dated Jan. 20, 2023, 17 pages.
Pending U.S. Appl. No. 16/865,772, Preliminary Amendment filed May 4, 2020, 6 pages.
Pending U.S. Appl. No. 16/865,772, Response to Apr. 11, 2022 Non-Final Office Action, dated Jul. 11, 2022, 8 pages.
Pending U.S. Appl. No. 16/865,772, Response to Aug. 22, 2022 Final Office Action, dated Dec. 22, 2022, 8 pages.
Pending U.S. Appl. No. 16/865,772, Response to Jan. 20, 2023 Non-Final Office Action, dated Apr. 20, 2023, 8 pages.
Pending U.S. Appl. No. 16/865,772, Second Preliminary Amendment filed Jun. 30, 2020, 4 pages.
Pending U.S. Appl. No. 16/865,772, Third Preliminary Amendment, filed Sep. 17, 2021, 6 pages.
Pending U.S. Appl. No. 16/915,760, Applicant-Initiated Interview Summary dated Aug. 8, 2023, 2 pages.
Pending U.S. Appl. No. 16/915,760, Final Office Action dated Aug. 10, 2023, 9 pages.
Pending U.S. Appl. No. 16/915,760, Final Office Action dated Jun. 2, 2023, 8 pages.
Pending U.S. Appl. No. 16/915,760, Non-Final Office Action dated Jan. 19, 2023, 8 pages.
Pending U.S. Appl. No. 16/915,760, Notice of Allowance dated Nov. 29, 2023, 7 pages.
Pending U.S. Appl. No. 16/915,760, Preliminary Amendment filed Jul. 6, 2020, 5 pages.
Pending U.S. Appl. No. 16/915,760 Response to Aug. 10, 2023 Final Office Action, dated Nov. 10, 2023, 6 pages.
Pending U.S. Appl. No. 16/915,760, Response to Jan. 19, 2023 Non-Final Office Action, dated Apr. 19, 2023, 8 pages.
Pending U.S. Appl. No. 16/915,760, Response to Sep. 20, 2022 Restriction Requirement, filed Nov. 21, 2022, 2 pages.
Pending U.S. Appl. No. 16/915,760, Restriction Requirement dated Sep. 20, 2022, 6 pages.
Pending U.S. Appl. No. 16/938,778, Non-Final Office Action dated Jan. 2, 2024, 12 pages.
Pending U.S. Appl. No. 16/938,778, Response to Oct. 24, 2023 Restriction Requirement, dated Dec. 13, 2023, 3 pages.
Pending U.S. Appl. No. 16/938,778, Restriction Requirement dated Oct. 24, 2023, 6 pages.
Pending U.S. Appl. No. 17/000,049, Non-Final Office Action dated Dec. 11, 2023, 13 pages.
Pending U.S. Appl. No. 17/000,049, Response to Jul. 31, 2023 Restriction Requirement dated Nov. 9, 2023, 8 pages.
Pending U.S. Appl. No. 17/000,049, Restriction Requirement dated Jul. 31, 2023, 6 pages.
Pending U.S. Appl. No. 17/172,731, Final Office Action dated Jul. 12, 2023, 11 pages.
Pending U.S. Appl. No. 17/172,731, Non-Final Office Action dated Feb. 15, 2023, 7 pages.
Pending U.S. Appl. No. 17/172,731, Non-Final Office Action dated Oct. 31, 2023, 13 pages.
Pending U.S. Appl. No. 17/172,731, Preliminary Amendment, filed Jun. 27, 2022, 9 pages.
Pending U.S. Appl. No. 17/172,731, Preliminary Amendment, filed Sep. 17, 2021, 7 pages.
Pending U.S. Appl. No. 17/172,731, Response to Feb. 15, 2023 Non-Final Office Action, dated May 15, 2023, 8 pages.
Pending U.S. Appl. No. 17/172,731, Response to Jul. 12, 2023 Final Office Action, dated Oct. 12, 2023, 10 pages.
Pending U.S. Appl. No. 17/172,731, Response to Oct. 31, 2023 Non-Final Office Action, dated Jan. 31, 2024, 7 pages.
Pending U.S. Appl. No. 17/277,662 Non-Final Office Action dated May 5, 2023, 9 pages.
Pending U.S. Appl. No. 17/277,662 Notice of Allowance dated Oct. 2, 2023, 7 pages.
Pending U.S. Appl. No. 17/277,662 Preliminary Amendment filed Mar. 18, 2021, 8 pages.
Pending U.S. Appl. No. 17/277,662 Response to May 5, 2023 Non-Final Office Action, dated Aug. 7, 2023, 8 pages.
Pending U.S. Appl. No. 17/338,960, Ex Parte Quayle Action dated May 24, 2023, 6 pages.
Pending U.S. Appl. No. 17/338,960, Response to May 24, 2023 Ex Parte Quayle Action, dated Aug. 8, 2023, 6 pages.
Pending U.S. Appl. No. 17/338,960, Response to Notice to File Missing Parts and Amendment, filed Aug. 16, 2021, 7 pages.
Pending U.S. Appl. No. 17/591,992, Non-Final Office Action dated Jan. 24, 2024, 7 pages.
Pending U.S. Appl. No. 17/591,992, Preliminary Amendment dated Sep. 20, 2023, 9 pages.
Pending U.S. Appl. No. 18/027,824, Preliminary Amendment dated Mar. 22, 2023, 8 pages.
Pending U.S. Appl. No. 18/100,835, Preliminary Amendment filed Jan. 26, 2023, 8 pages.
Mir, Therapeutic Perspectives of In Vivo Cell Electropermeabilization, Bioelectrochemistry, vol. 53, pp. 1-10, 2000.
Mulhall et al., "Cancer, pre-cancer and normal oral cells distinguished by dielectrophoresis." Analytical and Bioanalytical Chemistry, vol. 401, pp. 2455-2463 (2011).
Narayan, et al., Establishment and Characterization of a Human Primary Prostatic Adenocarcinoma Cell Line (ND-1), The Journal of Urology, vol. 148, 1600-1604, Nov. 1992.
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.
Naslund, Michael J., Transurethral Needle Ablation of the Prostate, Urology, vol. 50, No. 2, Aug. 1997.
Neal II et al., "A Case Report on the Successful Treatment of a Large Soft-Tissue Sarcoma with Irreversible Electroporation," Journal of Clinical Oncology, 29, pp. 1-6, 2011.
Neal II et al., "Experimental Characterization and Numerical Modeling of Tissue Electrical Conductivity during Pulsed Electric Fields for Irreversible Electroporation Treatment Planning," Biomedical Engineering, IEEE Transactions on Biomedical Engineering, vol. 59, pp. 1076-1085, 2012.
Neal II, R. E. et al. In Vitro and Numerical Support for Combinatorial Irreversible Electroporation and Electrochemotherapy Glioma Treatment. Annals of Biomedical Engineering, Oct. 29, 2013, 13 pages.
Neal II, R. E., et al., "Successful Treatment of a Large Soft Tissue Sarcoma with Irreversible Electroporation", Journal of Clinical Oncology, 29:13, e372-e377 (2011).
Neal II, R.E., et al., "Treatment of breast cancer through the application of irreversible electroporation using a novel minimally invasive single needle electrode." Breast Cancer Research and Treatment, 2010. 123(1): p. 295-301.
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
Neal RE II, et al. (2013) Improved Local and Systemic Anti-Tumor Efficacy for Irreversible Electroporation in Immunocompetent versus Immunodeficient Mice. PLoS ONE 8(5): e64559. https://doi.org/10.1371/journal.pone.0064559.
Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).

(56) References Cited

OTHER PUBLICATIONS

Neumann, et al., Gene Transfer into Mouse Lyoma Cells by Electroporation in High Electric Fields, J. Embo., vol. 1, No. 7, pp. 841-845, 1982.
Neumann, et al., Permeability Changes Induced by Electric Impulses in Vesicular Membranes, J. Membrane Biol., vol. 10, pp. 279-290, 1972.
Nikolova, B., et al., "Treatment of Melanoma by Electroporation of Bacillus Calmette-Guerin". Biotechnology & Biotechnological Equipment, 25(3): p. 2522-2524 (2011).
Nuccitelli, R., et al., "A new pulsed electric field therapy for melanoma disrupts the tumor's blood supply and causes complete remission without recurrence", Int J Cancer, 125(2): p. 438-45 (2009).
O'Brien et al., "Investigation of the Alamar Blue (resazurin) fluorescent dye for the assessment of mammalian cell cytotoxicity." European Journal of Biochemistry, vol. 267, pp. 5421-5426 (2000).
O'Brien, T. J. et al., "Effects of internal electrode cooling on irreversible electroporation using a perfused organ model," Int. J. Hyperth., vol. 35, No. 1, pp. 44-55, 2018.
Okino, et al., Effects of High-Voltage Electrical Impulse and an Anticancer Drug on In Vivo Growing Tumors, Japanese Journal of Cancer Research, vol. 78, pp. 1319-1321, 1987.
Onik, et al., Sonographic Monitoring of Hepatic Cryosurgery in an Experimental Animal Model, AJR American J. of Roentgenology, vol. 144, pp. 1043-1047, May 1985.
Onik, et al., Ultrasonic Characteristics of Frozen Liver, Cryobiology, vol. 21, pp. 321-328, 1984.
Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.
Onik, G., P. Mikus, and B. Rubinsky, "Irreversible electroporation: implications for prostate ablation." Technol Cancer Res Treat, 2007. 6(4): p. 295-300.
Organ, L.W., Electrophysiological principles of radiofrequency lesion making, Apply. Neurophysiol., 1976. 39: p. 69-76.
Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.
Pakhomova, O. N., Gregory, B., Semenov I., and Pakhomov, A. G., BBA—Biomembr., 2014, 1838, 2547-2554.
Partridge, B. R. et al., "High-Frequency Irreversible Electroporation for treatment of Primary Liver Cancer: A Proof-of-Principle Study in Canine Hepatocellular Carcinoma," J. Vasc. Interv. Radiol., vol. 31, No. 3, 482-491.e4, Mar. 2020, 19 pages.
Paszek et al., "Tensional homeostasis and the malignant phenotype." Cancer Cell, vol. 8, pp. 241-254 (2005).
Patent No. JP 7051188, Notice of Reasons for Revocation dated Jan. 30, 2023 (3 pages) with English translation (5 pages).
Patent No. JP 7051188, Opposition dated Jul. 4, 2022 (16 pages) with English translation (13 pages).
Patent No. JP 7051188, Response to Jan. 30, 2023 Notice of Reasons for Revocation, dated Apr. 27, 2023 (9 pages) with English translation (10 pages).
Patent No. JP 7051188, Response to Opposition dated Aug. 22, 2023 (21 pages) with English translation (25 pages).
Pavselj, N. et al. The course of tissue permeabilization studied on a mathematical model of a subcutaneous tumor in small animals. IEEE Trans Biomed Eng 52, 1373-1381 (2005).
Pavselj, N., et al., "A numerical model of skin electroporation as a method to enhance gene transfection in skin. 11th Mediterranean Conference on Medical and Biological Engineering and Computing", vols. 1 and 2, 16(1-2): p. 597-601 (2007).
PCT Application No. PCT/2011/062067, International Preliminary Report on Patentability dated May 28, 2013.
PCT Application No. PCT/2011/066239, International Preliminary Report on Patentability dated Jun. 25, 2013.
PCT Application No. PCT/US09/62806, International Search Report (Jan. 19, 2010), Written Opinion (Jan. 19, 2010), and International Preliminary Report on Patentability (Jan. 4, 2010), 15 pgs.
PCT Application No. PCT/US10/53077, International Search Report (Aug. 2, 2011), Written Opinion (Aug. 2, 2011), and International Preliminary Report on Patentability (Apr. 17, 2012).
PCT Application No. PCT/US15/30429, International Search Report and Written Opinion dated Oct. 16, 2015, 19 pages.
PCT Application No. PCT/US15/30429, International Report on Patentability dated Nov. 15, 2016.
PCT Application No. PCT/US15/65792, International Search Report (Feb. 9, 2016), Written Opinion (Feb. 9, 2016), and International Preliminary Report on Patentability (Jun. 20, 2017), 15 pages.
PCT Application No. PCT/US19/51731, International Preliminary Report on Patentability dated Mar. 23, 2021, 13 pages.
PCT Application No. PCT/US19/51731, International Search Report and Written Opinion dated Feb. 20, 2020, 19 pgs.
PCT Application No. PCT/US19/51731, Invitation to Pay Additional Search Fees dated Oct. 28, 2019, 2 pgs.
PCT Application No. PCT/US2004/043477, International Search Report (Aug. 26, 2005), Written Opinion (Aug. 26, 2005), and International Preliminary Report on Patentability (Jun. 26, 2006).
PCT Application No. PCT/US2009/042100, International Search Report (Jul. 9, 2009), Written Opinion (Jul. 9, 2009), and International Preliminary Report on Patentability (Nov. 2, 2010).
PCT Application No. PCT/US2010/029243, International Search Report, 4 pgs, (Jul. 30, 2010), Written Opinion, 7 pgs, (Jul. 30, 2010), and International Preliminary Report on Patentability, 8 pgs, (Oct. 4, 2011).
PCT Application No. PCT/US2010/030629, International Search Report (Jul. 15, 2010), Written Opinion (Jul. 15, 2010), and International Preliminary Report on Patentability (Oct. 11, 2011).
PCT Application No. PCT/US2011/062067, International Search Report and Written Opinion dated Jul. 25, 2012.
Appelbaum, L., et al., "US Findings after Irreversible Electroporation Ablation: Radiologic-Pathologic Correlation" Radiology 262(1), 117-125 (2012).
Arena et al. "High-Frequency Irreversible Electroporation (H-FIRE) for Non-thermal Ablation without Muscle Contraction." Biomed. Eng. Online, vol. 10, 20 pages (2011).
Arena, C. B. et al., "Theoretical Considerations of Tissue Electroporation With High-Frequency Bipolar Pulses," IEEE Trans. Biomed. Eng., vol. 58, No. 5, 1474-1482, 2011, 9 pages.
Arena, C.B., et al., "A three-dimensional in vitro tumor platform for modeling therapeutic irreversible electroporation." Biophysical Journal, 2012.103(9): p. 2033-2042.
Arena, Christopher B., et al., "Towards the development of latent heat storage electrodes for electroporation-based therapies", Applied Physics Letters, 101, 083902 (2012).
Arena, Christopher B., et al., "Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Asami et al., "Dielectric properties of mouse lymphocytes and erythrocytes." Biochimica et Biophysica Acta (BBA)—Molecular Cell Research, 1010 (1989) pp. 49-55.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).
Baker, et al., Calcium-Dependent Exocytosis in Bovine Adrenal Medullary Cells with Leaky Plasma Membranes, Nature, vol. 276, pp. 620-622, 1978.
Ball, C., K.R. Thomson, and H. Kavnoudias, "Irreversible electroporation: a new challenge in "out of-operating theater" anesthesia." Anesth Analg, 2010. 110(5): p. 1305-9.
Bancroft, et al., Design of a Flow Perfusion Bioreactor System for Bone Tissue-Engineering Applications, Tissue Engineering, vol. 9, No. 3, 2003, p. 549-554.
Baptista et al., "The Use of Whole Organ Decellularization for the Generation of a Vascularized Liver Organoid," Heptatology, vol. 53, No. 2, pp. 604-617 (2011).

(56) References Cited

OTHER PUBLICATIONS

Barber, Electrical Impedance Tomography Applied Potential Tomography, Advances in Biomedical Engineering, Beneken and Thevenin, eds., IOS Press, pp. 165-173, 1993.
Beebe, S.J., et al., "Diverse effects of nanosecond pulsed electric fields on cells and tissues", DNA and Cell Biology, 22(12): 785-796 (2003).
Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.
Beebe, S.J., et al.,, "Nanosecond, high-intensity pulsed electric fields induce apoptosis in human cells", FASEB J, 17 (9): p. 1493-5 (2003).
Beitel-White, N., S. Bhonsle, R. Martin, and R. V. Davalos, "Electrical characterization of human biological tissue for irreversible electroporation treatments," in 2018 40th Annual International Conference of the IEEE Engineering in Medicine and Biology Society (EMBC). IEEE, 2018, pp. 4170-4173.
Belehradek, J., et al., "Electropermeabilization of Cells in Tissues Assessed by the Qualitative and Quantitative Electroloading of Bleomycin", Biochimica Et Biophysica Acta—Biomembranes, 1190(1): p. 155-163 (1994).
Ben-David, E. et al., "Irreversible Electroporation: Treatment Effect Is Susceptible to Local Environment and Tissue Properties," Radiology, vol. 269, No. 3, 2013, 738-747.
Ben-David, E.,et al., "Characterization of Irreversible Electroporation Ablation in In Vivo Procine Liver" Am. J. Roentgenol. 198(1), W62-W68 (2012).
Benz, R., et al. "Reversible electrical breakdown of lipid bilayer membranes: a charge-pulse relaxation study". J Membr Biol, 48(2): p. 181-204 (1979).
Bhonsle, S. et al., "Characterization of Irreversible Electroporation Ablation with a Validated Perfused Organ Model," J. Vasc. Interv. Radiol., vol. 27, No. 12, pp. 1913-1922.e2, 2016.
Bhonsle, S. P. et al., "Mitigation of impedance changes due to electroporation therapy using bursts of high-frequency bipolar pulses," Biomed. Eng. (NY)., vol. 14, No. Suppl 3, 14 pages, 2015.
Bhonsle, S., M. F. Lorenzo, A. Safaai-Jazi, and R. V. Davalos, "Characterization of nonlinearity and dispersion in tissue impedance during high-frequency electroporation," IEEE Transactions on Biomedical Engineering, vol. 65, No. 10, pp. 2190-2201, 2018.
Blad, et al., Impedance Spectra of Tumour Tissue in Comparison with Normal Tissue; a Possible Clinical Application for Electrical Impedance Tomography, Physiol. Meas. 17 (1996) A105-A115.
Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.
Bonakdar, M., E. L. Latouche, R. L. Mahajan, and R. V. Davalos, "The feasibility of a smart surgical probe for verification of IRE treatments using electrical impedance spectroscopy," IEEE Trans. Biomed. Eng., vol. 62, No. 11, pp. 2674-2684, 2015.
Bondarenko, A. and G. Ragoisha, Eis spectrum analyser (the program is available online at http://www.abc.chemistry.bsu.by/vi/analyser/.
Boone, K., Barber, D. & Brown, B. Review—Imaging with electricity: report of the European Concerted Action on Impedance Tomography. J. Med. Eng. Technol. 21, 201-232 (1997).
Boussetta, N., N. Grimi, N. I. Lebovka, and E. Vorobiev, "Cold" electroporation in potato tissue induced by pulsed electric field, Journal of food engineering, vol. 115, No. 2, pp. 232-236, 2013.
Bower et al., "Irreversible electroporation of the pancreas: definitive local therapy without systemic effects." Journal of surgical oncology, 2011. 104(1): p. 22-28.
BPH Management Strategies: Improving Patient Satisfaction, Urology Times, May 2001, vol. 29, Supplement 1.
Brown, et al., Blood Flow Imaging Using Electrical Impedance Tomography, Clin. Phys. Physiol. Meas., 1992, vol. 13, Suppl. A, 175-179.
Brown, S.G., Phototherapy of tumors. World J. Surgery, 1983. 7: p. 700-9.
Buist et al., "Efficacy of multi-electrode linear irreversible electroporation," Europace, vol. 23, No. 3, pp. 464-468, 2021, 5 pages.
Bulvik, B. E. et al. "Irreversible Electroporation versus Radiofrequency Ablation : A Comparison of Local and Systemic Effects in a Small Animal Model," Radiology, vol. 280, No. 2, 2016, 413-424.
Butikofer, R. et al., "Electrocutaneous Nerve Stimulation-I: Model and Experiment," IEEE Trans. Biomed. Eng., vol. BME-25, No. 6, 526-531, 1978,6 pages.
Butikofer, R. et al., "Electrocutaneous Nerve Stimulation-II: Stimulus Waveform Selection," IEEE Trans. Biomed. Eng., vol. BME-26, No. 2, 69-75, 1979, abstract only, 2 pages.
Cannon et al., "Safety and early efficacy of irreversible electroporation for hepatic tumors in proximity to vital structures." Journal of Surgical Oncology, 6 pages (2012).
Carpenter A.E. et al., "CellProfiler: image analysis software for identifying and quantifying cell phenotypes." Genome Biol. 2006; 7(10): R100. Published online Oct. 31, 2006, 11 pages.
Castellvi, Q., B. Mercadal, and A. Ivorra, "Assessment of electroporation by electrical impedance methods," in Handbook of electroporation. Springer-Verlag, 2016, pp. 671-690.
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Chang, D.C., "Cell Poration and Cell-Fusion Using an Oscillating Electric-Field". Biophysical Journal, 56(4): p. 641-652 (1989).
Charpentier, K.P., et al., "Irreversible electroporation of the pancreas in swine: a pilot study." HPB: the official journal of the International Hepato Pancreato Biliary Association, 2010. 12(5): p. 348-351.
Chen et al., "Classification of cell types using a microfluidic device for mechanical and electrical measurement on single cells." Lab on a Chip, vol. 11, pp. 3174-3181 (2011).
Chen, M.T., et al., "Two-dimensional nanosecond electric field mapping based on cell electropermeabilization", PMC Biophys, 2(1):9 (2009).
Clark et al., "The electrical properties of resting and secreting pancreas." The Journal of Physiology, vol. 189, pp. 247-260 (1967).
Coates, C.W., et al., "The Electrical Discharge of the Electric Eel, Electrophorous Electricus," Zoologica, 1937, 22(1), pp. 1-32.
Cook, et al., ACT3: A High-Speed, High-Precision Electrical Impedance Tomograph, IEEE Transactions on Biomedical Engineering, vol. 41, No. 8, Aug. 1994.
Pending Application No. JP 2019-133057, Request for Appeal and Amended Claims (8 pages) with English translation of amended claims (2 pages) dated Dec. 23, 2021.
Pending Application No. JP 2019-133057, Response to Sep. 14, 2020 Office Action filed Mar. 18, 2021 (6 pages) with English Version of claims and response (5 pages).
Pending Application No. PCT/US21/51551, International Search Report and Written Opinion dated Dec. 29, 2021, 14 pages.
Pending Application No. PCT/US23/15118, International Search Report and Written Opinion dated Jul. 31, 2023, 18 pages.
Pending Application No. PCT/US23/15118, Invitation to Pay Additional Fees dated May 17, 2023, 3 pages.
Phillips, M., Maor, E. & Rubinsky, B. Non-Thermal Irreversible Electroporation for Tissue Decellularization. J. Biomech. Eng, doi: 10.1115/1.4001882 (2010).
Piñero, et al., Apoptotic and Necrotic Cell Death Are Both Induced by Electroporation in HL60 Human Promyeloid Leukaemia Cells, Apoptosis, vol. 2, No. 3, 330-336, Aug. 1997.
Polajžer, T. et al., "Cancellation effect is present in high-frequency reversible and irreversible electroporation," Bioelectrochemistry, vol. 132, 2020, 11 pages.

(56) References Cited

OTHER PUBLICATIONS

Polak et al., "On the Electroporation Thresholds of Lipid Bilayers: Molecular Dynamics Simulation Investigations." The Journal of Membrane Biology, vol. 246, pp. 843-850 (2013).
Pucihar et al., "Numerical determination of transmembrane voltage induced on irregularly shaped cells." Annals of Biomedical Engineering, vol. 34, pp. 642-652 (2006).
Qiao et al. Electrical properties of breast cancer cells from impedance measurement of cell suspensions, 2010, Journal of Physics, 224, 1-4 (2010).
Rajagopal, V. and S.G. Rockson, Coronary restenosis: a review of mechanisms and management, The American Journal of Medicine, 2003, 115(7): p. 547-553.
Reberšek, M. and D. Miklavčič, "Advantages and Disadvantages of Different Concepts of Electroporation Pulse Generation," Automatika 52(2011) 1, 12-19.
Reilly, J. P. et al., "Sensory Effects of Transient Electrical Stimulation—Evaluation with a Neuroelectric Model," IEEE Trans. Biomed. Eng., vol. BME-32, No. 12, 1001-1011, 1985, 11 pages.
Ringel-Scaia, V. M. et al., High-frequency irreversible electroporation is an effective tumor ablation strategy that induces immunologic cell death and promotes systemic anti-tumor immunity. EBioMedicine, 2019, 44, 112-125.
Rogers, W. R. et al., "Strength-duration curve an electrically excitable tissue extended down to near 1 nanosecond," IEEE Trans. Plasma Sci., vol. 32, No. 4 II, 1587-1599, 2004, 13 pages.
Rols, M.P., et al., Highly Efficient Transfection of Mammalian Cells by Electric Field Pulses: Application to Large Volumes of Cell Culture by Using a Flow System, Eur. J. Biochem. 1992, 206, pp. 115-121.
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-TIRE)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rossmeisl, John H. et al. Safety and feasibility of the NanoKnife system for irreversible electroporation ablative treatment of canine spontaneous intracranial gliomas. J. Neurosurgery 123.4 (2015): 1008-1025.
Rubinsky et al., "Optimal Parameters for the Destruction of Prostate Cancer Using Irreversible Electroporation." The Journal of Urology, 180 (2008) pp. 2668-2674.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. vol. 2 2000. 157-187.
Rubinsky, B., et al., "Irreversible Electroporation: A New Ablation Modality—Clinical Implications" Technol. Cancer Res. Treatment 6(1), 37-48 (2007).
Rubinsky, L. et al., "Electrolytic Effects During Tissue Ablation by Electroporation," Technol. Cancer Res. Treat., vol. 15, No. 5, NP95-103, 2016, 9 pages.
Sabuncu et al., "Dielectrophoretic separation of mouse melanoma clones." Biomicrofluidics, vol. 4, 7 pages (2010).
SAI Infusion Technologies, "Rabbit Ear Vein Catheters", https://www.sai-infusion.com/products/rabbit-ear-catheters, Aug. 10, 2017 webpage printout, 5 pages.
Salford, L.G., et al., "A new brain tumour therapy combining bleomycin with in vivo electropermeabilization", Biochem. Biophys. Res. Commun., 194(2): 938-943 (1993).
Salmanzadeh et al., "Investigating dielectric properties of different stages of syngeneic murine ovarian cancer cells" Biomicrofiuidics 7, 011809 (2013), 12 pages.
Salmanzadeh et al., "Dielectrophoretic differentiation of mouse ovarian surface epithelial cells, macrophages, and fibroblasts using contactless dielectrophoresis." Biomicrofluidics, vol. 6, 13 Pages (2012).
Salmanzadeh et al., "Sphingolipid Metabolites Modulate Dielectric Characteristics of Cells in a Mouse Ovarian Cancer Progression Model." Integr. Biol., 5(6), pp. 843-852 (2013).
Sanchez, B., G. Vandersteen, R. Bragos, and J. Schoukens, "Basics of broadband impedance spectroscopy measurements using periodic excitations," Measurement Science and Technology, vol. 23, No. 10, p. 105501, 2012.
Sanchez, B., G. Vandersteen, R. Bragos, and J. Schoukens, "Optimal multisine excitation design for broadband electrical impedance spectroscopy," Measurement Science and Technology, vol. 22, No. 11, p. 115601, 2011.
Sano et al., "Contactless Dielectrophoretic Spectroscopy: Examination of the Dielectric Properties of Cells Found in Blood." Electrophoresis, 32, pp. 3164-3171, 2011.
Sano et al., "In-vitro bipolar nano- and microsecond electro-pulse bursts for irreversible electroporation therapies." Bioelectrochemistry vol. 100, pp. 69-79 (2014).
Sano et al., "Modeling and Development of a Low Frequency Contactless Dielectrophoresis (cDEP) Platform to Sort Cancer Cells from Dilute Whole Blood Samples." Biosensors & Bioelectronics, 8 pages (2011).
Sano, M. B. et al., "Burst and continuous high frequency irreversible electroporation protocols evaluated in a 3D tumor model," Phys. Med. Biol., vol. 63, No. 13, 2018, 17 pages.
Sano, M. B. et al., "Reduction of Muscle Contractions During Irreversible Electroporation Therapy Using High-Frequency Bursts of Alternating Polarity Pulses: A Laboratory Investigation in an Ex Vivo Swine Model," J. Vasc. Interv. Radiol., vol. 29, No. 6, 893-898.e4, Jun. 2018, 18 pages.
Sano, M. B., et al., "Towards the creation of decellularized organ constructs using irreversible electroporation and active mechanical perfusion", Biomedical Engineering Online, Biomed Central LTD, London, GB, vol. 9, No. 1, Dec. 10, 2010, p. 83.
Saur et al., "CXCR4 expression increases liver and lung metastasis in a mouse model of pancreatic cancer." Gastroenterology, vol. 129, pp. 1237-1250 (2005).
Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.
Schoenbach et al., "Intracellular effect of ultrashort electrical pulses." Bioelectromagnetics, 22 (2001) pp. 440-448.
Seibert et al., "Clonal variation of MCF-7 breast cancer cells in vitro and in athymic nude mice." Cancer Research, vol. 43, pp. 2223-2239 (1983).
Seidler et al., "A Cre-loxP-based mouse model for conditional somatic gene expression and knockdown in vivo by using avian retroviral vectors." Proceedings of the National Academy of Sciences, vol. 105, pp. 10137-10142 (2008).
Sel, D. et al. Sequential finite element model of tissue electropermeabilization. IEEE Transactions on Biomedical Engineering 52, 816-827, doi: 10.1109/tbme.2005.845212 (2005).
Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Sersa, et al., Reduced Blood Flow and Oxygenation in SA-1 Tumours after Electrochemotherapy with Cisplatin, British Journal of Cancer, 87, 1047-1054, 2002.
Sersa, et al., Tumour Blood Flow Modifying Effects of Electrochemotherapy: a Potential Vascular Targeted Mechanism, Radiol. Oncol., 37(1): 43-8, 2003.
Shao, Qi et al. Engineering T cell response to cancer antigens by choice of focal therapeutic conditions, International Journal of Hyperthermia, 2019, DOI: 10.1080/02656736.2018.1539253.
Corovic et al., "Analytical and numerical quantification and comparison of the local electric field in the tissue for different electrode configurations," Biomed Eng Online, 6, 14 pages, 2007.

(56) References Cited

OTHER PUBLICATIONS

Cosman, E. R. et al., "Electric and Thermal Field Effects in Tissue Around Radiofrequency Electrodes," Pain Med., vol. 6, No. 6, 405-424, 2005, 20 pages.
Cowley, Good News for Boomers, Newsweek, Dec. 30, 1996/Jan. 6, 1997.
Cox, et al., Surgical Treatment of Atrial Fibrillation: A Review, Europace (2004) 5, S20-S-29.
Creason, S. C., J. W. Hayes, and D. E. Smith, "Fourier transform faradaic admittance measurements iii. comparison of measurement efficiency for various test signal waveforms," Journal of Electroanalytical chemistry and interfacial electrochemistry, vol. 47, No. 1, pp. 9-46, 1973.
Crowley, Electrical Breakdown of Biomolecular Lipid Membranes as an Electromechanical Instability, Biophysical Journal, vol. 13, pp. 711-724, 1973.
Dahl et al., "Nuclear shape, mechanics, and mechanotransduction." Circulation Research vol. 102, pp. 1307-1318 (2008).
Daskalov, I., et al., "Exploring new instrumentation parameters for electrochemotherapy—Attacking tumors with bursts of biphasic pulses instead of single pulses", IEEE Eng Med Biol Mag, 18(1): p. 62-66 (1999).
Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos et al., "Electrical impedance tomography for imaging tissue electroporation," IEEE Transactions on Biomedical Engineering, 51, pp. 761-767, 2004.
Davalos et al., "Theoretical analysis of the thermal effects during in vivo tissue electroporation." Bioelectrochemistry, vol. 61(1-2): pp. 99-107, 2003.
Davalos, et al., A Feasibility Study for Electrical Impedance Tomography as a Means to Monitor T issue Electroporation for Molecular Medicine, IEEE Transactions on Biomedical Engineering, vol. 49, No. 4, Apr. 2002.
Davalos, et al., Tissue Ablation with Irreversible Electroporation, Annals of Biomedical Engineering, vol. 33, No. 2, p. 223-231, Feb. 2005.
Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.
De Senneville, B. D. et al., "MR thermometry for monitoring tumor ablation," European radiology, vol. 17, No. 9, pp. 2401-2410, 2007.
De Vuyst, E., et al., "In situ bipolar Electroporation for localized cell loading with reporter dyes and investigating gap junctional coupling", Biophysical Journal, 94(2): p. 469-479 (2008).
Dean, Nonviral Gene Transfer to Skeletal, Smooth, and Cardiac Muscle in Living Animals, Am J. Physiol Cell Physiol 289: 233-245, 2005.
Demirbas, M. F., "Thermal Energy Storage and Phase Change Materials: An Overview" Energy Sources Part B 1(1), 85-95 (2006).
Dev, et al., Medical Applications of Electroporation, IEEE Transactions of Plasma Science, vol. 28, No. 1, pp. 206-223, Feb. 2000.
Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.
Duraiswami, et al., Boundary Element Techniques for Efficient 2-D and 3-D Electrical Impedance Tomography, Chemical Engineering Science, vol. 52, No. 13, pp. 2185-2196, 1997.
Duraiswami, et al., Efficient 2D and 3D Electrical Impedance Tomography Using Dual Reciprocity Boundary Element Techniques, Engineering Analysis with Boundary Elements 22, (1998) 13-31.
Duraiswami, et al., Solution of Electrical Impedance Tomography Equations Using Boundary Element Methods, Boundary Element Technology XII, 1997, pp. 226-237.
Edd et al., "Mathematical modeling of irreversible electroporation for treatment planning." Technology in Cancer Research and Treatment, vol. 6, No. 4, pp. 275-286 (2007).
Edd, J., et al., In-Vivo Results of a New Focal Tissue Ablation Technique: Irreversible Electroporaton, IEEE Trans. Biomed. Eng. 53 (2006) p. 1409-1415.
Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).
Eppich et al., "Pulsed electric fields for selection of hematopoietic cells and depletion of tumor cell contaminants." Nature Biotechnology 18, pp. 882-887 (2000).
Erez, et al., Controlled Destruction and Temperature Distributions in Biological Tissues Subjected to Monoactive Electrocoagulation, Transactions of the ASME: Journal of Mechanical Design, vol. 102, Feb. 1980.
Ermolina et al., "Study of normal and malignant white blood cells by time domain dielectric spectroscopy." IEEE Transactions on Dielectrics and Electrical Insulation, 8 (2001) pp. 253-261.
Esser, A.T., et al., "Towards solid tumor treatment by irreversible electroporation: intrinsic redistribution of fields and currents in tissue". Technol Cancer Res Treat, 6(4): p. 261-74 (2007).
Esser, A.T., et al., "Towards Solid Tumor Treatment by Nanosecond Pulsed Electric Fields", Technology in Cancer Research & Treatment, 8(4): p. 289-306 (2009).
Faroja, M., et al., "Irreversible Electroporation Ablation: Is the entire Damage Nonthermal?", Radiology, 266(2), 462-470 (2013).
Fischbach et al., "Engineering tumors with 3D scaffolds." Nat Meth 4, pp. 855-860 (2007).
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).
Foster RS, "High-intensity focused ultrasound in the treatment of prostatic disease", European Urology, 1993, vol. 23 Suppl 1, pp. 29-33.
Foster, R.S., et al., Production of Prostatic Lesions in Canines Using Transrectally Administered High-Intensity Focused Ultrasound. Eur. Urol., 1993; 23: 330-336.
Fox, et al., Sampling Conductivity Images via MCMC, Mathematics Department, Auckland University, New Zealand, May 1997.
Frandsen, S. K., H. Gissel, P. Hojman, T. Tramm, J. Eriksen, and J. Gehl. Direct therapeutic applications of calcium electroporation to effectively induce tumor necrosis. Cancer Res. 72:1336-41, 2012.
Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).
Garcia et al., "Irreversible electroporation (IRE) to treat brain cancer." ASME Summer Bioengineering Conference, Marco Island, FL, Jun. 25-29, 2008, 2 pages.
Garcia P.A., et al., "7.0-T Magnetic Resonance Imaging Characterization of Acute Blood-Brain-Barrier Disruption Achieved with Intracranial Irreversible Electroporation", Plos One, Nov. 2012, 7:11, e50482.
Garcia P.A., et al., "Pilot study of irreversible electroporation for intracranial surgery", Conf Proc IEEE Eng Med Biol Soc, 2009:6513-6516, 2009.
Garcia, et al., "A Parametric Study Delineating Irreversible Electroporation from Thermal Damage Based on a Minimally Invasive Intracranial Procedure," Biomed Eng Online, vol. 10:34, 22 pages, 2011.
Garcia, P. A., et al., "Towards a predictive model of electroporation-based therapies using pre-pulse electrical measurements," Conf Proc IEEE Eng Med Biol Soc, vol. 2012, pp. 2575-2578, 2012.
Garcia, P. A., et al., "Non-thermal Irreversible Electroporation (N-TIRE) and Adjuvant Fractioned Radiotherapeutic Multimodal

(56) References Cited

OTHER PUBLICATIONS

Therapy for Intracranial Malignant Glioma in a Canine Patient" Technol. Cancer Res. Treatment 10(1), 73-83 (2011).
Garcia, P. et al. Intracranial nonthermal irreversible electroporation: in vivo analysis. J Membr Biol 236, 127-136 (2010).
Garcia, Paulo A., Robert E. Neal II and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010, 22 pages.
García-Sánchez, T., A. Azan, I. Leray, J. Rosell-Ferrer, R. Bragos, and L. M. Mir, "Interpulse multifrequency electrical impedance measurements during electroporation of adherent differentiated myotubes," Bioelectrochemistry, vol. 105, pp. 123-135, 2015.
PCT Application No. PCT/US2011/066239, International Search Report (Aug. 22, 2012), and Written Opinion (Aug. 22, 2012).
Pending U.S. Appl. No. 14/686,380, Advisory Action dated Oct. 20, 2021, 3 pages.
Pending U.S. Appl. No. 14/686,380, Amendment After Board Decision dated Apr. 3, 2023, 8 pages.
Pending U.S. Appl. No. 14/686,380, Appeal Brief filed Nov. 5, 2021, 21 pages.
Pending U.S. Appl. No. 14/686,380, Appeal Decision dated Jan. 30, 2023, 15 pages.
Pending U.S. Appl. No. 14/686,380, Applicant Initiated Interview Summary dated Feb. 9, 2021, 3 pages.
Pending U.S. Appl. No. 14/686,380, Applicant Initiated Interview Summary dated Mar. 8, 2021, 2 pages.
Pending U.S. Appl. No. 14/686,380, Examiner's Answer to Appeal Brief, dated Feb. 18, 2022, 16 pages.
Pending U.S. Appl. No. 14/686,380, Final Office Action dated May 9, 2018, 14 pages.
Pending U.S. Appl. No. 14/686,380, Final Office Action dated Oct. 6, 2020, 14 pages.
Pending U.S. Appl. No. 14/686,380, Final Office Action dated Sep. 3, 2019, 28 pages.
Pending U.S. Appl. No. 14/686,380, Non-Final Office Action dated Feb. 13, 2020, 11 pages.
Pending U.S. Appl. No. 14/686,380, Non-Final Office Action dated May 1, 2019, 18 pages.
Pending U.S. Appl. No. 14/686,380, Non-Final Office Action dated Nov. 22, 2017, 11 pages.
Pending U.S. Appl. No. 14/686,380, Notice of Non-Compliant Amendment dated May 25, 2023, 3 pages.
Pending U.S. Appl. No. 14/686,380, Reply Brief, dated Apr. 12, 2022, 4 pages.
Pending U.S. Appl. No. 14/686,380, Response to Feb. 13, 2020 Non-Final Office Action, filed Jul. 1, 2020, 8 pages.
Pending U.S. Appl. No. 14/686,380, Response to Jul. 19, 2017 Restriction Requirement, dated Sep. 15, 2017, 2 pages.
Pending U.S. Appl. No. 14/686,380, Response to May 9, 2018 Final Office Action with RCE, dated Aug. 30, 2018, 14 pages.
Pending U.S. Appl. No. 14/686,380, Response to Non-Final Office Action Filed Aug. 1, 2019, 11 pages.
Pending U.S. Appl. No. 14/686,380, Response to Nov. 22, 2017 Non-Final Office Action dated Mar. 28, 2018, 11 pages.
Pending U.S. Appl. No. 14/686,380, Response to Oct. 6, 2020 Final Office Action with RCE, dated Jan. 6, 2020, 11 pages.
Pending U.S. Appl. No. 14/686,380, Response to Sep. 3, 2019 Final Office Action, filed Jan. 3, 2020, 10 pages.
Pending U.S. Appl. No. 14/686,380, Restriction Requirement Jul. 19, 2017, 7 pages.
Pending U.S. Appl. No. 14/686,380, Amendment after Notice of Appeal, dated Oct. 12, 2021, 6 pages.
Pending U.S. Appl. No. 14/686,380, Non-Final Office Action dated May 7, 2021, 17 pages.
Pending U.S. Appl. No. 16/375,878, Applicant-Initiated Interview Summary dated Aug. 23, 2022, 7 pages.
Pending U.S. Appl. No. 16/375,878, Final Office Action dated Apr. 15, 2022, 8 pages.
Pending U.S. Appl. No. 16/375,878, Final Office Action dated Aug. 18, 2023, 11 pages.
Pending U.S. Appl. No. 16/375,878, Non-Final Office Action dated Jan. 23, 2023, 8 pages.
Pending U.S. Appl. No. 16/375,878, Non-Final Office Action dated Jun. 24, 2021, 8 pages.
Pending U.S. Appl. No. 16/375,878, Notice of Allowance dated Nov. 15, 2023, 6 pages.
Pending U.S. Appl. No. 16/375,878, Preliminary Amendment, filed Apr. 9, 2019, 9 pages.
Pending U.S. Appl. No. 16/375,878, Response to Apr. 15, 2022 Final Office Action, dated Aug. 15, 2022, 8 pages.
Pending U.S. Appl. No. 16/375,878, Response to Aug. 18, 2023 Final Office Action, dated Oct. 18, 2023, 9 pages.
Pending U.S. Appl. No. 16/375,878, Response to Jan. 23, 2023 Non-Final Office Action, dated Apr. 24, 2023, 10 pages.
Pending U.S. Appl. No. 16/375,878, Response to Jun. 24, 2021 Non-Final Office Action, dated Dec. 22, 2021, 8 pages.
Pending U.S. Appl. No. 16/375,878, Second Preliminary Amendment, filed Feb. 5, 2020, 3 pages.
Pending U.S. Appl. No. 16/747,219, Applicant-Initiated Interview Summary dated Aug. 3, 2022, 4 pages.
Pending U.S. Appl. No. 16/747,219, Final Office Action dated Nov. 10, 2022, 12 pages.
Pending U.S. Appl. No. 16/747,219, Non-Final Office Action dated Mar. 31, 2022, 12 pages.
Pending U.S. Appl. No. 16/747,219, Non-Final Office Action dated May 25, 2023, 13 pages.
Pending U.S. Appl. No. 16/747,219, Notice of Allowance dated Dec. 26, 2023, 12 pages.
Pending U.S. Appl. No. 16/747,219, Preliminary Amendment filed Jan. 20, 2020, 5 pages.
Pending U.S. Appl. No. 16/747,219, Preliminary Amendment filed Jan. 4, 2021, 5 pages.
Pending U.S. Appl. No. 16/747,219, Response to Mar. 31, 2022 Non-Final Office Action, dated Aug. 1, 2022, 8 pages.
Pending U.S. Appl. No. 16/747,219, Response to May 25, 2023 Non-Final Office Action, dated Aug. 25, 2023, 9 pages.
Pending U.S. Appl. No. 16/747,219, Response to Nov. 10, 2022 Final Office Action, dated Feb. 10, 2023, 6 pages.
Pending U.S. Appl. No. 16/865,031, Final Office Action dated May 24, 2023, 18 pages.
Pending U.S. Appl. No. 16/865,031, Non-Final Office Action dated Nov. 28, 2022, 16 pages.
(Aycock, Kenneth N. et al.) Co-pending U.S. Appl. No. 19/368,292, filed Oct. 24, 2025, Specification, Claims, and Figures.
(Davalos, Rafael et al.) Co-Pending U.S. Appl. No. 18/846,198, filed Sep. 11, 2024, Specification, Claims, Figures.
(Davalos, Rafael et al.) Co-Pending U.S. Appl. No. 19/120,676, filed Apr. 11, 2025, Specification, Claims, Figures.
(Davalos, Rafael V. et al.) Co-pending U.S. Appl. No. 18/767,746, filed Jul. 9, 2024, Specification, Claims, Figures.
(Davalos, Rafael V. et al.) Co-pending U.S. Appl. No. 19/026,703, filed Jan. 17, 2025, Specification, Claims, Drawings.
(Garcia, Paulo A. et al.) Co-pending U.S. Appl. No. 19/302,564, filed Aug. 18, 2025, Specification, Claims, Figures.
(Lorenzo, Melvin F. et al.) Co-pending U.S. Appl. No. 19/044,045, filed Feb. 3, 2025, Specification, Claims, Figures.
(Neal, Robert E. et al.) Co-pending U.S. Appl. No. 18/930,252, filed Oct. 29, 2024, Specification, Claims, Figures.
(Neal, Robert E. et al.) Co-pending U.S. Appl. No. 19/019,625, filed Jan. 14, 2025, Specification, Claims, Figures.
(O'Brien, Timothy J. et al.) Co-Pending U.S. Appl. No. 18/608,958, filed Mar. 19, 2024, Specification, Claims, Figures.
AutoMACS Pro Separator Miltenyi Biotec User Manual (2019), 169 pages.
Korohoda, W. et al. "Reversible and Irreversible Electroporation of Cell Suspensions Flowing Through a Localized DC Electric Field", Cellular & Molecular Biology Letters, vol. 18 (2013), pp. 102-119 (published Dec. 27, 2012).

(56) References Cited

OTHER PUBLICATIONS

Lv, Y. et al. "The Englargement of Ablation Area by Electrolytic Irreversible Electroporation (E-IRE) Using Pulsed Field with Bias DC Field", Annals of Biomedical Engineering, vol. 50, No. 12, Dec. 2022, 10 pages.
Manuel, E. R. *Salmonella*-Based Therapy Targeting Indoleamine 2,3-Dioxygenase Coupled with Enzymatic Depletion of Tumor Hyaluronan Induces Complete Regression of Aggressive Pancreatic Tumors, Cancer Immunology Res., (2015), 3(9): 1096-1107.
Pending U.S. Appl. No. 16/938,778, Interview Summary dated Jun. 21, 2024, 1 page.
Pending U.S. Appl. No. 16/938,778, Notice of Allowance dated Jun. 21, 2024, 10 pages.
Pending U.S. Appl. No. 16/938,778, Response to Jan. 2, 2024 Non-Final Office Action, dated Apr. 2, 2024, 13 pages.
Pending U.S. Appl. No. 17/000,049, Examiner Interview Summary dated Jul. 8, 2024, 7 pages.
Pending U.S. Appl. No. 17/000,049, Final Office Action dated Mar. 29, 2024, 15 pages.
Pending U.S. Appl. No. 17/000,049, Response to Dec. 11, 2023 Non-Final Office Action, dated Mar. 11, 2024, 9 pages.
Pending U.S. Appl. No. 17/152,379, Final Office Action dated Dec. 11, 2024, 8 pages.
Pending U.S. Appl. No. 17/152,379, Non-Final Office Action dated Apr. 23, 2024, 14 pages.
Pending U.S. Appl. No. 17/152,379, Response to Apr. 23, 2024 Non-Final Office Action, filed Aug. 23, 2024, 7 pages.
Pending U.S. Appl. No. 17/172,731, Final Office Action dated Apr. 10, 2024, 5 pages.
Pending U.S. Appl. No. 17/172,731, Notice of Allowance dated Jun. 27, 2024, 7 pages.
Pending U.S. Appl. No. 17/172,731, Response to Apr. 10, 2024 Final Office Action, dated Jun. 10, 2024, 6 pages.
Pending U.S. Appl. No. 17/535,742, Final Office Action dated Apr. 29, 2025, 11 pages.
Pending U.S. Appl. No. 17/535,742, Non-final Office Action dated Dec. 13, 2024, 12 pages.
Pending U.S. Appl. No. 17/535,742, Notice of Allowance dated Aug. 20, 2025, 8 pages.
Pending U.S. Appl. No. 17/535,742, Response to Apr. 29, 2025 Final Office Action dated Jul. 22, 2025, 7 pages.
Pending U.S. Appl. No. 17/535,742, Response to Dec. 13, 2024 Non-final Office Action, dated Apr. 14, 2025, 9 pages.
Pending U.S. Appl. No. 17/591,992, Final Office Action dated Jul. 30, 2024, 10 pages.
Pending U.S. Appl. No. 17/591,992, Non-Final Office Action dated Feb. 23, 2024, 9 pages.
Pending U.S. Appl. No. 17/591,992, Non-Final Office Action dated Nov. 18, 2024, 9 pages.
Pending U.S. Appl. No. 17/591,992, Notice of Allowance dated Apr. 1, 2025, 7 pages.
Pending U.S. Appl. No. 17/591,992, Response to Feb. 23, 2024 Non-Final Office Action dated May 23, 2024, 10 pages.
Pending U.S. Appl. No. 17/591,992, Response to Jul. 30, 2024 Final Office Action, dated Sep. 30, 2024, 9 pages.
Pending U.S. Appl. No. 17/591,992, Response to Nov. 18, 2024 Non-Final Office Action, dated Feb. 15, 2025, 7 pages.
Pending U.S. Appl. No. 17/862,486, Non-final Office Action dated Aug. 22, 2025, 8 pages.
Pending U.S. Appl. No. 17/862,486, Response to Aug. 22, 2025 Non-final Office Action dated Nov. 6, 2025, 3 pages.
Pending U.S. Appl. No. 18/027,824, Non-Final Office Action dated Nov. 3, 2025, 26 pages.
Pending U.S. Appl. No. 18/100,835, Final Office Action dated Dec. 11, 2025, 9 pages.
Pending U.S. Appl. No. 18/100,835, Final Office Action dated Mar. 6, 2025, 12 pages.
Pending U.S. Appl. No. 18/100,835, Non-Final Office Action dated Jun. 23, 2025, 12 pages.
Pending U.S. Appl. No. 18/100,835, Non-Final Office Action dated Oct. 23, 2024, 10 pages.
Pending U.S. Appl. No. 18/100,835, Response to Jun. 23, 2025 Non-Final Office Action dated Oct. 23, 2025, 8 pages.
Pending U.S. Appl. No. 18/100,835, Response to Jun. 28, 2024 Restriction Requirement, dated Aug. 28, 2024, 5 pages.
Pending U.S. Appl. No. 18/100,835, Response to Mar. 6, 2025 Final Office Action, dated Jun. 6, 2025, 12 pages.
Pending U.S. Appl. No. 18/100,835, Response to Oct. 23, 2024 Non-Final Office Action, dated Jan. 23, 2025, 8 pages.
Pending U.S. Appl. No. 18/100,835, Restriction Requirement dated Jun. 28, 2024, 6 pages.
Pending U.S. Appl. No. 18/120,158, Non-Final Office Action dated Jun. 20, 2024, 13 pages.
Pending U.S. Appl. No. 18/120,158, Notice of Allowance dated Oct. 2, 2024, 5 pages.
Pending U.S. Appl. No. 18/120,158, Response to Jun. 20, 2024 Non-Final Office Action, dated Sep. 20, 2024, 8 pages.
Pending U.S. Appl. No. 18/123,719, Non-Final Office Action dated Sep. 23, 2025, 8 pages.
Pending U.S. Appl. No. 18/130,330, Second Preliminary Amendment dated Feb. 26, 2024, 3 pages.
Pending U.S. Appl. No. 18/348,605, Examiner Interview Summary dated Jun. 6, 2025, 3 pages.
Pending U.S. Appl. No. 18/348,605, Examiner Interview Summary dated Nov. 17, 2025, 3 pages.
Pending U.S. Appl. No. 18/348,605, Final Office Action dated Feb. 5, 2025, 9 pages.
Pending U.S. Appl. No. 18/348,605, Final Office Action dated Jan. 21, 2026, 11 pages.
Pending U.S. Appl. No. 18/348,605, Non-Final Office Action dated Jul. 14, 2025, 8 pages.
Pending U.S. Appl. No. 18/348,605, Non-Final Office Action dated Sep. 5, 2024, 10 pages.
Pending U.S. Appl. No. 18/348,605, Response to Jul. 14, 2025 Non-Final Office Action, dated Nov. 14, 2025, 11 pages.
Pending U.S. Appl. No. 18/348,605, Response to Sep. 5, 2024 Non-Final Office Action, dated Dec. 5, 2024, 7 pages.
Pending U.S. Appl. No. 18/402,231, Non-Final Office Action dated Dec. 13, 2024, 8 pages.
Pending U.S. Appl. No. 18/402,231, Notice of Allowance dated Apr. 10, 2025, 7 pages.
Pending U.S. Appl. No. 18/402,231, Preliminary Amendment dated Mar. 5, 2024, 5 pages.
Pending U.S. Appl. No. 18/402,231, Response to Dec. 13, 2024 Non-Final Office Action, dated Mar. 13, 2025, 3 pages.
Pending U.S. Appl. No. 18/404,473, Preliminary Amendment dated May 13, 2024, 6 pages.
Pending U.S. Appl. No. 18/502,967, Non-Final Office Action dated Jun. 18, 2024, 25 pages.
Pending U.S. Appl. No. 18/502,967, Notice of Allowance dated Dec. 2, 2024, 9 pages.
Pending U.S. Appl. No. 18/502,967, Response to Jun. 18, 2024 Non-Final Office Action dated Sep. 18, 2024, 12 pages.
Pending U.S. Appl. No. 18/608,958, Non-Final Office Action dated Jan. 15, 2026, 10 pages.
Pending U.S. Appl. No. 18/767,746, Preliminary amendment dated Oct. 4, 2024, 5 pages.
Pending U.S. Appl. No. 18/846,198, Preliminary Amendment dated Sep. 11, 2024, 8 pages.
Pending U.S. Appl. No. 18/930,252, Preliminary Amendment dated Apr. 25, 2025, 118 pages.
Pending U.S. Appl. No. 19/019,625, Preliminary Amendment dated Apr. 4, 2025, 194 pages.
Pending U.S. Appl. No. 19/026,703, Preliminary Amendment dated Mar. 3, 2025, 6 pages.
Pending U.S. Appl. No. 19/044,045, Preliminary amendment dated Jul. 9, 2025, 6 pages.
Pending U.S. Appl. No. 19/120,676, Preliminary Amendment dated Apr. 11, 2025, 8 pages.
Pending Application No. EP 15793361.5, Brief Communication from the EPO, dated Aug. 19, 2024, 1 page.

(56) References Cited

OTHER PUBLICATIONS

Pending Application No. EP 15793361.5, Communication dated Feb. 8, 2024, 4 pages.
Pending Application No. EP 15793361.5, EPO Result of Consultation, Aug. 12, 2024, 3 pages.
Pending Application No. EP 15793361.5, Response to Feb. 8, 2024 Communication, Filed Aug. 2, 2024, 40 pages.
Pending Application No. EP 15793361.5, Supplemental Response to Feb. 8, 2024 Communication, Filed Aug. 16, 2024, 9 pages.
Pending Application No. PCT/US23/76626, International Search Report and Written Opinion, dated Apr. 17, 2024, 12 pages.
Pending Application No. PCT/US23/76626, Invitation to Pay Additional Fees dated Feb. 21, 2024, 2 pages.
Reti, I. M. and Davydow, D. S., "Electroconvulsive Therapy and Antibiotics: A Case Report", J. ECT, vol. 23, No. 4, Dec. 2007, pp. 289-290.
Sano, M. B. et al., Bursts of Bipolar Microsecond Pulses Inhibit Tumor Growth, Scientific Reports, (2015), 5: 14999, 13 pages.
U.S. Appl. No. 14/686,380, file history through Dec. 2023, 265 pages.
U.S. Appl. No. 16/865,772, file history through Aug. 2023, 110 pages.
Pending U.S. Appl. No. 17/862,486, Notice of Allowance dated Apr. 24, 2026, 7 pages.
Pending U.S. Appl. No. 18/100,835, Notice of Allowance dated Apr. 21, 2026, 7 pages.
Pending U.S. Appl. No. 18/130,330, Non-Final Rejection dated Apr. 6, 2026, 18 pages.
Pending U.S. Appl. No. 18/348,605, Response to Jan. 21, 2026 Final Office Action, dated May 21, 2026, 12 pages.
Pending U.S. Appl. No. 18/608,958, Response to Jan. 15, 2026 Non-Final Office Action dated May 15, 2026, 10 pages.
Pending U.S. Appl. No. 18/767,746, Non-Final Office Action dated May 12, 2026, 9 pages.
Pending U.S. Appl. No. 18/846,198, Non-Final Office Action dated May 19, 2026, 18 pages.
Pending U.S. Appl. No. 19/368,292, Preliminary Amendment dated Apr. 20, 2026, 7 pages.
Pending U.S. Appl. No. 19/302,564, Preliminary Amendment filed May 4, 2026, 7 pages.
Pending U.S. Appl. No. 18/027,824, Notice of Allowance dated Sep. 24, 2026, 9 pages.
Pending U.S. Appl. No. 18/123,719, Notice of Allowance dated Aug. 6, 2026, 7 pages.
Pending U.S. Appl. No. 18/130,330, Response to Apr. 6, 2026 Non-Final Rejection, dated Aug. 6, 2026, 11 pages.
Pending U.S. Appl. No. 18/348,605, Non-Final Office Action dated Jul. 16, 2026, 11 pages.
Pending U.S. Appl. No. 18/404,473, Non-Final Office Action dated Aug. 10, 2026, 8 pages.
Pending U.S. Appl. No. 18/608,958, Response to Notice of Non-Compliant Amendment, dated Sep. 9, 2026, 8 pages.
Pending U.S. Appl. No. 18/767,746, Notice of Allowance dated Sep. 30, 2026, 7 pages.
Pending U.S. Appl. No. 18/767,746, Response to May 12, 2026 Non-Final Office Action, dated Aug. 12, 2026, 6 pages.
Pending U.S. Appl. No. 18/846,198, Response to May 19, 2026 Non-Final Office Action, dated Aug. 19, 2026, 12 pages.
Pending U.S. Appl. No. 18/930,252, Non-Final Office Action dated Jul. 29, 2026, 9 pages.
Pending Application No. CN 202011281572.3, First Office Action dated Aug. 18, 2026 (15 pages) with English translation (22 pages).

* cited by examiner

SYSTEM AND METHOD FOR ABLATING A TISSUE SITE BY ELECTROPORATION WITH REAL-TIME MONITORING OF TREATMENT PROGRESS

Cross Reference to Related Applications

The present application claims priority to and is a Continuation application of U.S. application Ser. No. 16/280,511, filed on Feb. 20, 2019, which published as U.S. Patent Application Publication No. 2019/0175248 on Jun. 13, 2019, which is a Continuation application of U.S. application Ser. No. 14/940,863, filed on Nov. 13, 2015, which published as U.S. Patent Application Publication No. 2016/0066977 on Mar. 10, 2016, and which issued as U.S. Pat. No. 10,238,447 on Mar. 26, 2019. The '863 application claims priority to and the benefit of the filing date of U.S. Provisional Application No. 62/079,061 filed on Nov. 13, 2014, and U.S. Provisional Application No. 62/173,538 filed on Jun. 10, 2015. The '863 application is also a Continuation-in-Part (CIP) application of parent application U.S. application Ser. No. 14/012,832, filed on Aug. 28, 2013, which published as U.S. Patent Application Publication No. 2013/0345697 on Dec. 26, 2013 and issued as U.S. Pat. No. 9,283,051 on Mar. 15, 2016. The '832 application is a Continuation-in-Part (CIP) application of U.S. application Ser. No. 12/491, 151, filed on Jun. 24, 2009, which published as U.S. Patent Application Publication No. 2010/0030211 on Feb. 4, 2010, and issued as U.S. Pat. No. 8,992,517 on Mar. 31, 2015. The '151 application claims priority to and the benefit of the filing dates of U.S. Provisional Patent Application Nos. 61/171,564, filed on Apr. 22, 2009, 61/167,997, filed on Apr. 9, 2009, and 61/075,216, filed on Jun. 24, 2008, and the '151 application is a Continuation-in-Part application of U.S. patent application Ser. No. 12/432,295, filed on Apr. 29, 2009, which published as U.S. Patent Application Publication No. 2009/0269317 on Oct. 29, 2009 and issued as U.S. Pat. No. 9,598,691 on Mar. 21, 2017. The '295 application claims priority to and the benefit of the filing date of U.S. Provisional Patent Application No. 61/125,840, filed on Apr. 29, 2008. All of these applications, publications and patents are incorporated by reference herein in their entireties.

FIELD OF THE INVENTION

The present invention relates to a control system for controlling an electroporation medical treatment device and more particularly, to such devices with real- time monitoring of electroporation treatment progress.

BACKGROUND OF THE INVENTION

Medical devices for delivering therapeutic energy such as electrical pulses to tissue include one or more electrodes and a pulse generator. The pulse generator allows the electrode to deliver the therapeutic energy to a targeted tissue, thereby causing ablation of the tissue.

Electroporation procedure parameters that influence the size and shape of their affected region include the nature of the tissue (cellularity, extracellular constituent composition, anisotropy, conductivity, metabolic demand), patient specific anatomy, the pulse delivery apparatus (number of electrodes, their size, and relative geometry), and pulse parameters (voltage, number of pulses, pulse length, pulse delivery rate). In addition to the above, the generator's maximum pulse intensity capabilities (maximum voltage and current) dictate the maximum achievable treatment region. Where controllable and large lesions are desired, it is important to maintain pulses that are capable of inducing electroporation effects to the tissue while remaining below the maximum generator capacity.

In conventional electroporation devices, before the treatment procedure a physician would decide on a particular pulse delivery apparatus and select the pulse parameters. As can be appreciated, the electroporation therapy treatment plans selected by the physician are limited to using a retrospective dimension data approach, where a pre-determined pulse parameter protocol is delivered between each electrode pair in an array and the pulse parameters are selected from previously existing ablation data. Once the treatment procedure starts, the electroporation device follows the pre-treatment programming set by the physician and delivers the pulses according to the pre-selected pulse parameters.

However, this approach ignores the specifics of the actual case, which will vary both in terms of initial tissue properties and tissue response to the electroporation pulses for each patient. Specifically, there is no way to monitor the progress of the treatment procedure or alter the settings other than to stop the procedure manually. Thus, even when the procedure completes normally, there was no assurance that there were clinically sufficient electroporation of the targeted region due to the unpredictable nature of patient environments and living tissue.

Therefore, it would be desirable to provide a system and method for monitoring the progress of an electroporation treatment procedure in real-time and to determine in real-time whether an end point has been reached for particular patients.

SUMMARY OF THE DISCLOSURE

According to one aspect of the present invention, a medical system for ablating a tissue site with real-time monitoring during an electroporation treatment procedure includes at least two electrodes and a pulse generator configured to generate electroporation pulses for ablation of tissue in a target region. The pulse generator also generates a pre-treatment (PT) test signal having a frequency of at least 1 MHz prior to the treatment procedure and intra-treatment (IT) test signals during the treatment procedure. Use of the PT test signal provides a baseline value that is specific to the patient being treated. A treatment control module determines impedance values from the PT test signal and IT test signals and determines a progress of electroporation in real- time based on the determined impedance values while the treatment procedure progresses.

According to another aspect of the present invention, a method of determining a progress of an electroporation treatment procedure for ablating a tissue site is provided. The method applies a PT test signal having a frequency of at least 1 MHZ to a target region of a tissue site through at least one electrode and determines an impedance value based on the applied PT test signal. Use of the PT test signal provides a baseline impedance value that is specific to the patient being treated. During the treatment procedure, a plurality of IT test signals are applied and an impedance value for each applied IT test signal is determined. The method then determines a progress of electroporation of the target tissue site, based on the determined impedance values of the IT test signals and PT test signal. The method can also determine an end of treatment based on the determined impedance values of the IT test signals and PT test signal.

Advantageously, use of a baseline value which is specific to the particular patient being treated for monitoring the progress and determining an end of treatment in real-time will result in improved treatment delivery and improved likelihood for successful outcome.

DETAILED DESCRIPTION OF THE INVENTION

Figure 1:
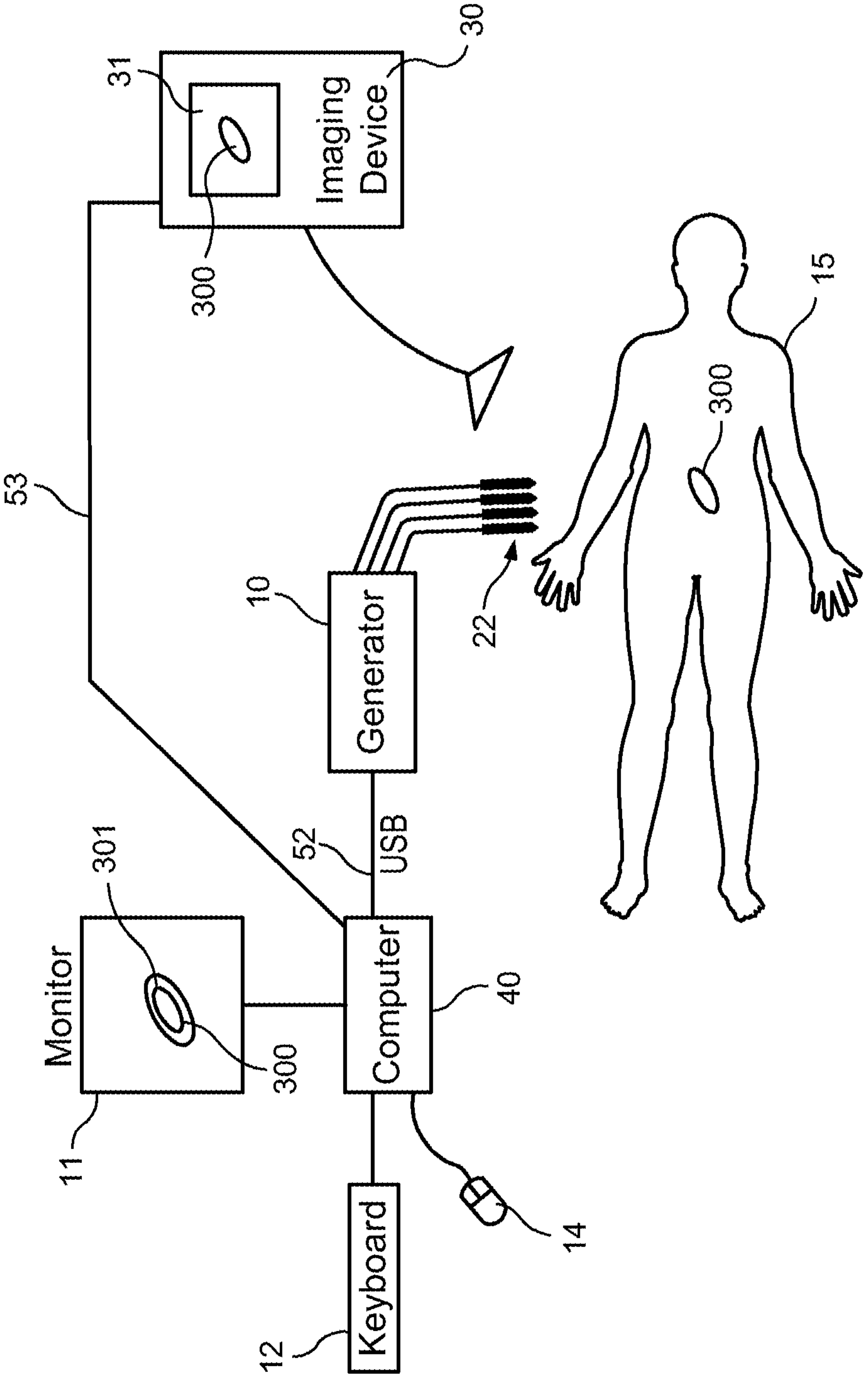
FIG. 1 is a block diagram of an electroporation device according to one aspect of the present invention.

Throughout the present teachings, any and all of the one, two, or more features and/or components disclosed or suggested herein, explicitly or implicitly, may be practiced and/or implemented in any combinations of two, three, or more thereof, whenever and wherever appropriate as understood by one of ordinary skill in the art. The various features and/or components disclosed herein are all illustrative for the underlying concepts, and thus are non-limiting to their actual descriptions. Any means for achieving substantially the same functions are considered as foreseeable alternatives and equivalents, and are thus fully described in writing and fully enabled. The various examples, illustrations, and embodiments described herein are by no means, in any degree or extent, limiting the broadest scopes of the claimed inventions presented herein or in any future applications claiming priority to the instant application.

In the present specification, the voltage value of any AC signals refers to root mean square (RMS) voltage, rather than peak voltage, unless specifically mentioned otherwise. Throughout the present specification, tissue properties are discussed in terms of an impedance. Both impedance and conductance measure the resistance of tissue in passing current. Thus, any reference to an impedance of tissue necessarily encompasses conductivity and vice versa.

Irreversible Electroporation (IRE), a new minimally invasive technique we invented to treat tumors, can be enhanced using carbon nanotubes (CNTs). The technique can be used on a variety of tumors including liver, prostate, pancreatic adenocarcinoma and renal carcinoma. In the present invention, biofeedback in the form of local bulk tissue electrical properties and their change in response to electroporation (EP) or irreversible electroporation (IRE) therapy are used to guide the user and indicate the extent or progress of electroporation during the electroporation procedure and to determine an end point for the procedure while the procedure is in progress. Specifically, impedance of test signals is used to enable a refined determination of EP effects and dimension, thus improving tolerances for ablation dimensions and ensuring successful electroporation in the desired regions. Ultimately, this will result in improved treatment delivery, more accurate determination of treated tissue dimensions and margins, provide users with feedback information on determining success of the procedure, faster treatment times, and improved likelihood for successful ablation outcomes in EP ablation treatment.

The tissue properties can be measured through dedicated measurement electrodes, or through the same electrodes that apply electroporation pulses. In the case of the latter, if there are more than one pair of electrodes that apply electroporation pulses, e.g., 2 pairs, the tissue property measurements can be made with one pair while the other pair is applying electroporation treatment pulses. The measurements are generally made during the quiet times between electroporation pulses.

Figure 6:
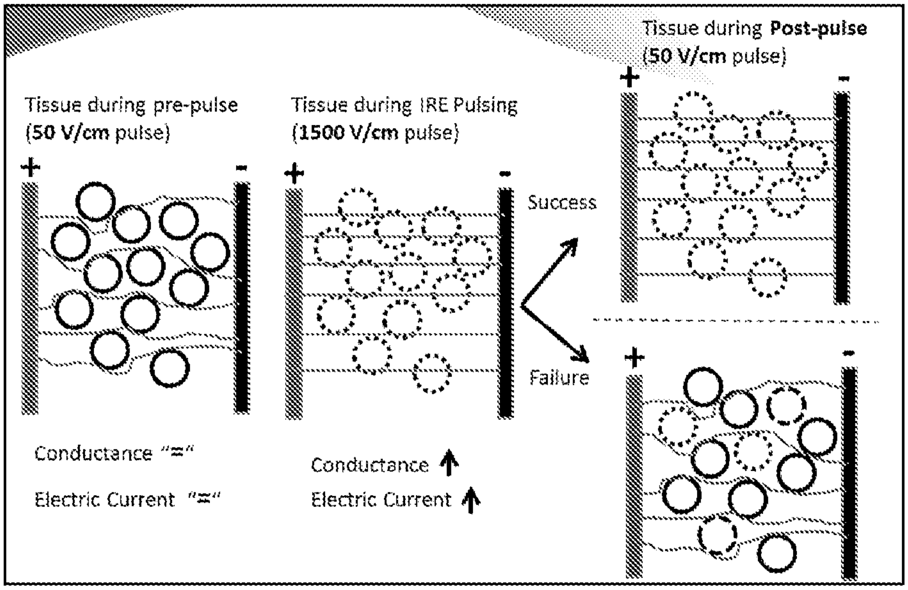
FIG. 6 is a schematic depiction of successful and failed electroporation treatment procedures.

It relies on the fact that electroporated cell membranes no longer serve a significant barrier to electrolyte mobility and electrical current flow through the cells in tissue. In turn, electroporated regions will increase the bulk tissue conductivity. When irreversible, this change at the cellular level is permanent. This increased conductivity may then serve as an artifact to indicate the extent of tissue electroporation. As a result, it is likely that pulse metric behavior and trends correlate with ablation dimensions. By measuring and analyzing tissue property changes, such as a change in conductivity and/or impedance, that result from the electroporation therapy, the present invention deduces the dimensions or completeness of an IRE lesion and uses this information to control the progress of an electroporation therapy. This information provides the user with feedback that can be used to set or adjust the pulse parameters (voltage, pulse length, number of pulses) to tailor the treatment protocol to the specific patient, and/or indicate when a particular electrode pair has satisfied their required ablation dimensions to attain complete coverage of the targeted region. This phenomenon is illustrated in FIG. 6. Prior to the treatment procedure, as shown in the left image, electrical current from a DC test voltage of 50 V/cm flows around the cells without electroporation because the DC current cannot penetrate the cell membranes (shown as dark circles). The impedance/conductance and current are steady and do not change from one test pulse to the next. Once electroporation pulses start to be delivered as the middle image shows, however, the membranes start to develop holes and electrical current start to flow through the punctured cell membranes (shown as dotted circles). As a result, conductance and current from the DC test pulse increase from one test pulse to the next.

If the irreversible electroporation treatment procedure was successful, the electroporated cells would be unable to close the membrane holes, and the electrical current and the associated impedance/conductance from the test pulses would stabilize to certain predetermined known values. However, if the irreversible electroporation treatment procedure was not successful, that means either at least some of the cells were able to repair and close the holes or membranes of some of the cells were never punctured. In that case, the current would only be able to flow through the punctured membranes and not through the repaired cell membranes. As a result, the current and conductance would not reach the known threshold values.

There are several possible methods of determining the progress and end point of a treatment procedure.

One method uses a desired ultimate current value for a given electrode geometry and pulse protocol to indicate completeness or progress (e.g., percentage of completion) of the treatment procedure. Preferably, the current values are obtained from test signals prior to and in between IRE treatment pulses. If the desired threshold value is not reached, the voltage or pulse length could be increased, or the application of treatment electroporation pulses would continue until the threshold value is reached by relying on the concept of a current-creep where electrical currents have a tendency to increase over the course of a procedure due to increasing electroporated volume and cell electroporation density as well as cumulative temperature increases. An exemplary threshold current value may be 0.35 Amps.

Another method is to use a relative/changing current. Rather than relying on a threshold target current, this procedure relies on a change in the electrical current in the test signals to indicate the changing tissue properties over the course of an IRE sequence between electrodes. Preferably, this method would employ an averaging algorithm, such as a simple moving average (SMA) or exponential moving average (EMA) over several consecutive test signal, which provides for a more stable evaluation of electric current change, and factors out signal-by-signal anomalies in current. As an example, two SMA's would be used with one lagging the other by several test signals.

It uses either a difference in current relative to that from an earlier pulse ($\Delta i = i_k - i_0$) or as a relative change (% $\Delta i = \Delta i / i_0$) as the threshold value. As a very simple example, the threshold difference in current can be 0.02 Amps and the threshold relative change in percentage can be 1.0%. If the desired threshold value is not reached, pulsing would continue until it does (relying on current-creep while factoring out thermal influence on rise in current) or the voltage or pulse length could be increased based on user input.

Another method is to use a desired final threshold impedance value (either absolute impedance value or relative/changing impedance value) for a given electrode geometry and pulse protocol to indicate completeness or progress (e.g., percentage of completion) of the treatment procedure. Similar to the method discussed above with respect to measuring the current values, this method would also employ an averaging algorithm, such as a simple moving average (SMA) or exponential moving average (EMA) over several consecutive test signal, which provides for a more stable evaluation values and factors out signal-by-signal anomalies.

In a preferred embodiment, only the real part of the impedance value is used. If using the absolute impedance value (preferably the real part of impedance if AC test signals are used), pulsing is continued until the desired threshold value (e.g., 150 Ohm) is reached. The desired threshold value can be derived from a pre-treatment test signal and/or the type of tissue being treated. If the desired threshold impedance value is not reached, the voltage or pulse length could be increased, or the pulsing would continue until the threshold value is reached by relying on the concept of an impedance-creep where electrical impedance has a tendency to decrease over the course of a procedure due to increasing electroporated volume and cell electroporation density, while controlling to factor out current-creep due to cumulative temperature increases.

If using a relative impedance value (preferably the real part of impedance) as the threshold value, a change in the electrical impedance can be monitored for indicating the changing tissue properties over the course of an IRE sequence between electrodes. It uses either a difference in impedance relative to that from an earlier pulse ($\Delta R = R_k - R_0$) or as a relative change (% $\Delta R = \Delta R / R_0$) as the threshold value. For example, the threshold difference in impedance can be 10 Ohms and the threshold relative change in percentage can be 1.0%. If the desired threshold value is not reached, pulsing would continue until it does (relying on impedance-creep) or the voltage or pulse length could be increased based on user input. An advantage of using impedance values is that the influence of what voltage is applied is factored out, resulting in a more accurate and reliable method of monitoring the treatment progress and determining the end point of the treatment procedure.

Using pulse metrics derived from the actual therapeutic EP or IRE pulses to indicate tissue properties and their response to electroporation pulses does not account for the transiently altered tissue properties resulting from reversibly electroporated cells. As a result, monitoring purely therapy pulse metrics may give a false-read on the extent of electroporation, due to the 2 to 5-fold increase in electrical conductivity of many tissues during electroporation pulses. To more effectively attain a determination of the completeness and size of irreversibly electroporated tissue, a low-strength test signal can be applied between adjacent therapy pulses or sets of pulses. This low-voltage test signal would not inherently permeabilize the cells, and thus changes in its current or resistance may better indicate bulk tissue property changes resulting from IRE. Thus, in utilizing this type of indicator to control pulse protocols, the changes indicated would then mimic those aforementioned for the therapy pulses (current and resistance; absolute thresholds and relative changes). An upper limit for the desired post-pulse resistance could potentially be derived from the effective resistance of the tissue during the electroporation therapy pulses.

One embodiment of the present invention is illustrated in FIG. 1. The components used with the present invention are illustrated in FIG. 1. One or more electrodes/probes 22 deliver therapeutic energy and are powered by a voltage pulse generator 10 that generates high voltage pulses as therapeutic energy such as pulses capable of irreversibly electroporating the tissue cells. In the embodiment shown, the voltage pulse generator 10 includes six separate receptacles for receiving up to six individual probes 22 which are adapted to be plugged into the respective receptacle. The receptacles are each labeled with a number in consecutive order. In other embodiments, the voltage pulse generator 10 can have any number of receptacles for receiving more or less than six probes.

Each probe 22 includes either a monopolar electrode, bipolar electrodes having at least two electrodes (electrode conducting regions) separated by an insulating sleeve, or multipolar electrodes having greater than two electrode surfaces separated by one or more insulating sleeves which can be energized simultaneously or at different times. In one embodiment, if the probe includes a monopolar electrode, the amount of exposure of the active portion of the electrode can be adjusted by retracting or advancing an insulating sleeve relative to the electrode. See, for example, U.S. Pat. No. 7,344,533, which is incorporated by reference herein. In embodiments, an electrode may be a ground pad electrode positionable at an exterior position on the patient. In the embodiment shown, the probes 22 are monopolar electrodes. The generator 10 is connected to a treatment control computer 40 having input devices such as keyboard 12 and a pointing device 14, and an output device such as a display device 11 for viewing an image of a target treatment area such as a lesion 300 surrounded by a safety margin 301. The therapeutic energy delivery device 20 is used to treat a lesion 300 inside a patient 15. An imaging device 30 includes a monitor 31 for viewing the lesion 300 inside the patient 15 in real time. Examples of imaging devices 30 include ultrasonic, CT, MRI and fluoroscopic devices as are known in the art.

For purposes of this application, the terms "code", "software", "program", "application", "software code", "software module", "module" and "software program" are used interchangeably to mean software instructions that are executable by a processor.

The "user" can be a physician or other medical professional. The treatment control module 54 (FIG. 2) executed by a processor outputs various data including text and graphical data to the monitor 11 associated with the generator 10.

Figure 2:
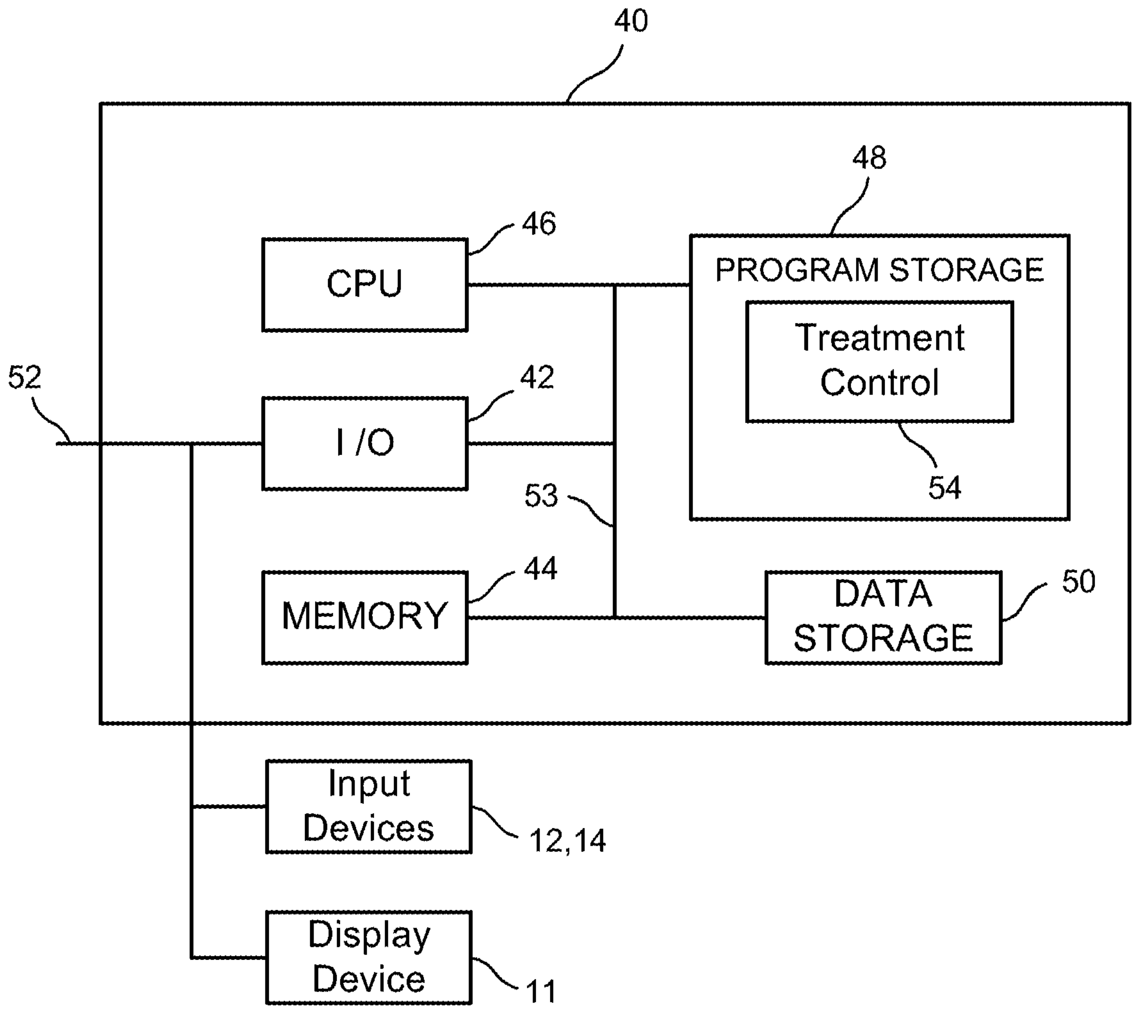
FIG. 2 is a block diagram of a treatment control computer of FIG. 1.

Referring now to FIG. 2, the treatment control computer 40 of the present invention is connected to the communication link 52 through an I/O interface 42 such as a USB (universal serial bus) interface, which receives information from and sends information over the communication link 52 to the voltage generator 10. The computer 40 includes memory storage 44 such as RAM, processor (CPU) 46, program storage 48 such as ROM or EEPROM, and data storage 50 such as a hard disk, all commonly connected to each other through a bus 53. The program storage 48 stores, among others, computer software (treatment control module 54) which assists a user/physician to plan for, execute, and review the results of a medical treatment procedure. The treatment control module 54, executed by the processor 46, assists a user to plan for a medical treatment procedure by enabling a user to more accurately position each of the probes 22 of the therapeutic energy delivery device 20 in relation to the lesion 300 in a way that will generate the most effective treatment zone. The treatment control module 54 can display the anticipated treatment zone based on the position of the probes and the treatment parameters. Using any of the above described methods, the treatment control module 54 can display the progress of the treatment in real time and can display the results of the treatment procedure after it is completed. This information can be used to determine whether the treatment was successful and whether it is necessary to re-treat the patient.

Figure 5:
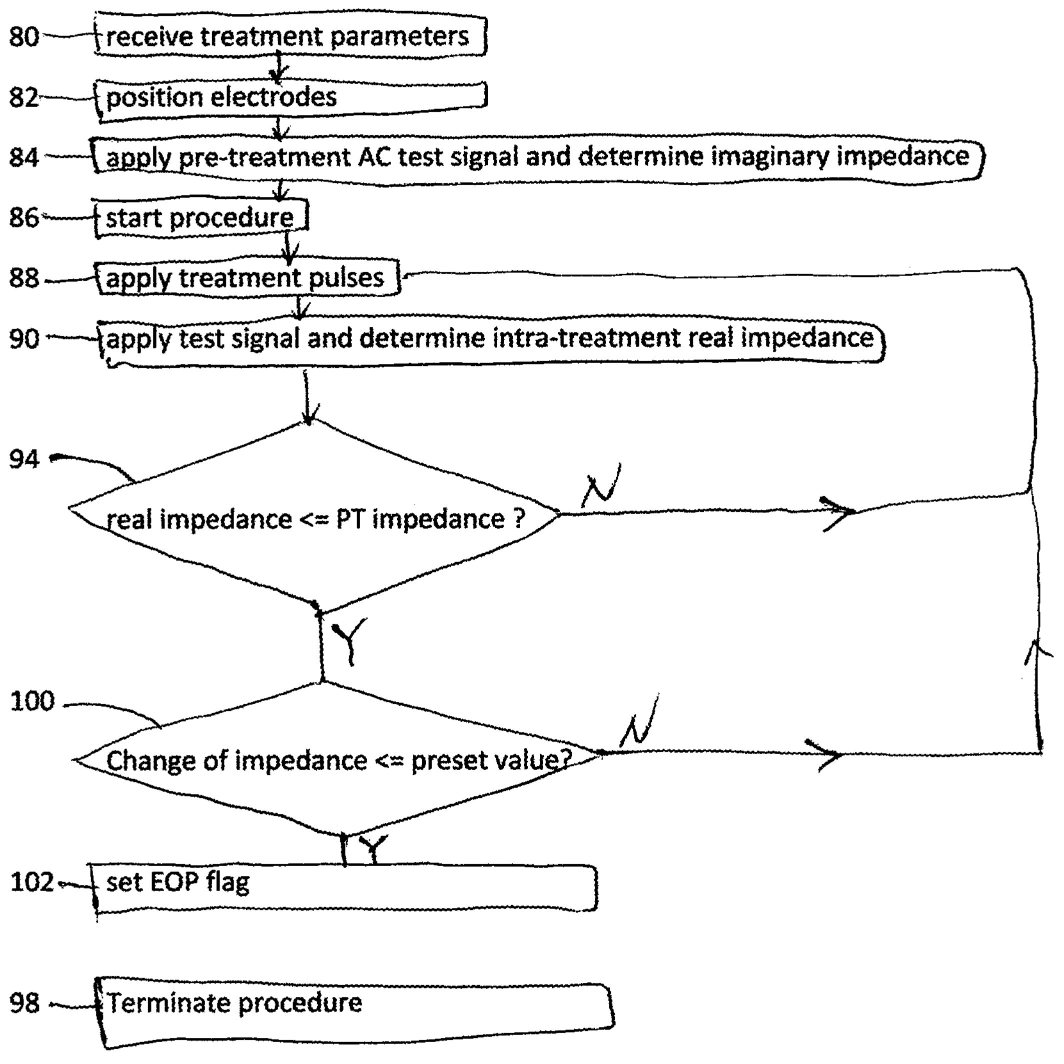
FIG. 5 is a flowchart of a method of ablating a tissue site by electroporation with real-time monitoring of treatment progress during an electroporation procedure.

The module 54 is also adapted to monitor and display the progress of the electroporation procedure and to determine a successful end point based on the electrical properties of the tissue prior to and during the treatment procedure as will be explained in more detail with reference to FIG. 5. Being able to in real-time monitor and see the end point of the treatment procedure is a huge advantage over the current method in which the physician is performing the treatment essentially blindly without having any idea about whether the treatment is progressing or at what point the treatment procedure is finished.

The program storage 48 stores various electrical threshold values that are used to monitor the treatment procedure. When the programmed sequence of pulses have been delivered and the end point of the procedure has not been reached, the user interface portion of the control module 54 retrieves the recommended parameter changes from the database and presents them to the user through the display 11. The treatment control module 54 can also change the threshold values for determining the progress and the end point of the procedure based on initial treatment pulse parameters programmed by the user. For example, different body parts/organs or different health/age of patients may require different thresholds as their conductivity and susceptibility to irreversible electroporation may differ. User can manually input the various thresholds for different tissue types or the system can have these thresholds stored electronically.

Alternatively, the treatment control module 54 can also automatically derive or adjust the threshold values for determining the progress and the end point of the procedure based on test signals (e.g., AC test signals) that are applied and determining electrical properties of the cells such as impedance values. The control module 54 may then store the changed threshold values in the program storage 48 for later use as the new criteria for comparison.

Further, AC intra-treatment test signals may continue to be delivered in addition to the comparative DC intra-treatment test signals. By tracking the change in impedance for the AC-signal, the treatment control module 54 determines and factors out the effects on impedance occurring due to temperature rise. This enables more accurately tracking changes in the real-part of the impedance by reflecting changes encountered solely due to persistent electroporated cells. A more detailed discussion of the control module 54 will be made later herein with reference to FIG. 5.

Any of the software program modules in the program storage 48 and data from the data storage 50 can be transferred to the memory 44 as needed and is executed by the CPU 46.

In one embodiment, the computer 40 is built into the voltage generator 10. In another embodiment, the computer 40 is a separate unit which is connected to the voltage generator through the communications link 52. The communication link 52 can be, for example, a USB link.

In one embodiment, the imaging device 30 is a standalone device which is not connected to the computer 40. In the embodiment as shown in FIG. 1, the computer 40 is connected to the imaging device 30 through a communications link 53. As shown, the communication link 53 is a USB link. In this embodiment, the computer can determine the size and orientation of the lesion 300 by analyzing the data such as the image data received from the imaging device 30, and the computer 40 can display this information on the monitor 11. In this embodiment, the lesion image generated by the imaging device 30 can be directly displayed on the monitor 11 of the computer running the treatment control module 54. This embodiment would provide an accurate representation of the lesion image on the grid 200, and may eliminate the step of manually inputting the dimensions of the lesion in order to create the lesion image on the grid 200. This embodiment would also be useful to provide an accurate representation of the lesion image if the lesion has an irregular shape.

It should be noted that the software can be used independently of the generator 10. For example, the user can plan the treatment in a different computer as will be explained below and then save the treatment parameters to an external memory device, such as a USB flash drive (not shown). The data from the memory device relating to the treatment parameters can then be downloaded into the computer 40 to be used with the generator 10 for treatment.

Figure 3:
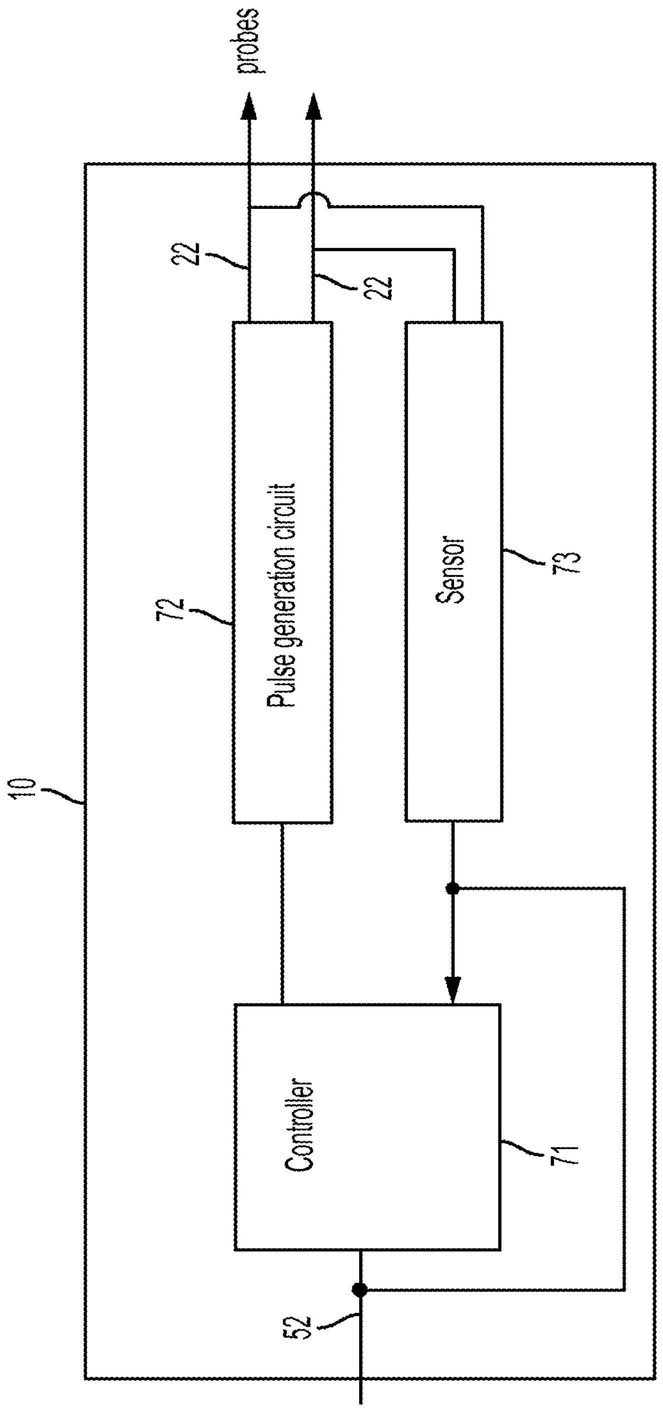
FIG. 3 is a block diagram of a pulse generator shown in FIG. 1.

FIG. 3 is a functional block diagram of a pulse generator 10 shown in FIG. 1. FIG. 2 illustrates one embodiment of a circuitry to monitor the progress of and determine an end point of the treatment procedure. A USB connection 52 carries instructions from the user computer 40 to a controller 71. The controller 71 can be a computer similar to the computer 40 as shown in FIG. 2. The controller 71 can include a processor, ASIC (application-specific integrated circuit), microcontroller or wired logic. The controller 71 then sends the instructions to a pulse generation circuit 72. The pulse generation circuit 72 generates the pulses and sends electrical energy to the probes. For clarity, only one pair of probes/electrodes is shown. However, the generator

10 can accommodate any number of probes/electrodes such as 6 probes. In the embodiment shown, the pulses are applied one pair of electrodes at a time, and then switched to another pair. The pulse generation circuit 72 includes a switch, preferably an electronic switch that switches the probe pairs based on the instructions received from controller 71.

A sensor 73 can sense the current and voltage between each pair of the probes in real time and communicate such information to the controller 71, which in turn, communicates the information to the computer 40. Although the treatment control module 54 houses the software code for monitoring the treatment procedure, it may be beneficial for the controller 71 to store such module as the speed of monitoring can be important in some cases.

Figure 4:
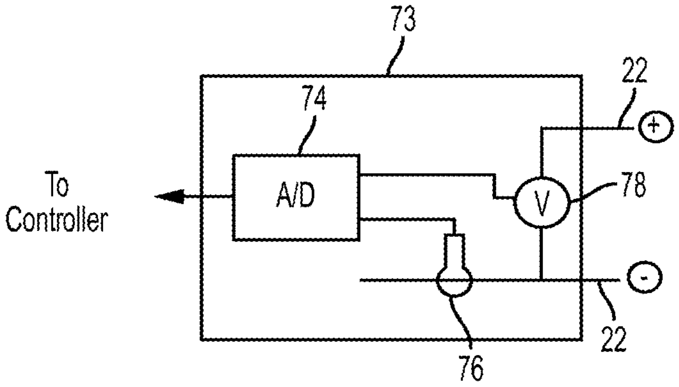
FIG. 4 is a block diagram of a sensor of FIG. 3.

FIG. 4 is a functional block diagram of a sensor 73 of FIG. 3. The sensor 73 includes a voltage sensor 78 connected across a pair of electrodes 22 and a current sensor 78 connected to a negative electrode (return conduit) in the pair of electrodes. Although FIGS. 3-4 show two electrodes from two wires 22, there may be multiple electrodes between the two wires 22. The sensed values are continuously received and digitized by an A/D converter 74 and transmitted to the controller 71. Preferably, the A/D converter 74 can sample the sensed values at a very fast rate and preferably at a rate of at least 100 MHz (100 million samples per second) for the control module 54 to be able to accurately assess the complex impedance of test signals which may be an AC signal at a relatively high frequency.

The current sensor 76 can be a Hall effect sensor/probe which is positioned around an electrode so as to measure the electric current without directly interfering with the pulse signal. Typically, the current sensor 76 is placed on the negative signal connection of the electrode pair. If the electrode pairs are switched, then only one current sensor connected at the input side of the switch is needed. Otherwise, if there are 3 pairs of electrodes, for example, and all are firing at the same time, there will be 3 current sensors so as to measure the electric current of each pair separately. In that case, the current from the three sensors will need to be added, The voltage sensor 78 can be a conventional voltage divider, comprised of two serially connected resistors, that measures a voltage drop across a known resistance value. The voltage sensor 78 uses resistors which are of much higher resistance than the tissue (kΩ-MΩ, versus tissue, which is hundreds of Ω), and thus induces negligible effect on the strength of the pulses delivered to the tissue. A correction factor is calculated for the divider circuit based on the resistances of the two resistors in the voltage divider circuit and the resistance of the load (tissue resistance) to determine the true delivered voltage to the tissue based on the measured voltage drop across the resistor.

A method of ablating a tissue site with real-time monitoring during an electroporation treatment procedure will now be explained with reference to FIG. 5.

The steps executed are part of the treatment control module 54 which can be part of the computer 40 or a part of the controller 71 in the pulse generator 10 itself for faster response. Referring to FIG. 5, in step 80, the treatment control module 54 graphically interacts with the user to receive treatment parameters which include voltage between electrodes, electrode separation distance, firing sequence among the electrode pairs, pulse delivery/firing rate, pulse duty cycle, number of pulses in a pulse set/train, number of pulse sets/trains, inter-pulse delay, inter pulse train delay, electrode exposure length, pulse parameter changes for each abnormal condition and the like. In step 82, a user/physician positions the electrodes 22 at a tissue site such that the electroporation field covers the target region. The target region is now ready to be treated.

Prior to the start of the actual treatment procedure (prior to delivering electroporation pulses), however, at least one pre-treatment (PT) test signal is delivered to establish a baseline parameter to be compared to similar parameters during the treatment so that a progress and an end of treatment can be determined during the treatment procedure.

In step 84, the pulse control module 54 instructs the controller 71 in the pulse generator 10 to generate the PT test signal through the electrodes 22 that have been placed in the patient. Preferably, the pulse generation circuit 72 generates an alternating current (AC) sine wave signal as the PT test signal whose voltage amplitude (RMS) is insufficient to cause an electroporation of a majority of tissue cells in the target region, and more preferably is insufficient to cause electroporation of any tissue cells in the target region. Although the voltage of the PT test signal depends to a certain extent on the type of tissue cells to be ablated, it is generally less than 500 volts/cm and is preferably between 10 and 200 volts/cm. The frequency of the PT test signal is between 1 KHz and 2 GHz. More preferably, the frequency of the PT test signal is at least 1 MHz and at most 1 GHz. At 1 MHz, the effect of the cellular membrane on impedance starts to diminish as the current at that frequency would start to bypass the capacitive nature of the membranes.

Most preferably, however, the frequency of the PT test signal is at least 100 MHz at which frequency the cell membrane's effects on impedance is substantially diminished and/or at most 500 MHz. At 100 MHz, the frequency is higher than the Beta dispersion frequency (approximately 1 KHz to 1 MHZ) to minimize the effect of the cellular membranes to resist current flow and maximize the effects of the intra-cellular structures on current flow. The duration of the PT test signal can vary but should be sufficiently long (e.g., 1-10 milliseconds) to establish a stable impedance value. If needed, several PT test signals can be made to ensure that the impedance value is consistent.

While the PT test signal is being applied, the sensor 73 continuously senses the current values which are sent to the controller 71. The treatment control module 54 then determines a complex impedance from the measured current values along with the applied voltage as measured from the voltage sensor 78. In some embodiment, the complex impedance could be in the form of conductance. As well known in the art, the complex impedance can be written as the following equation.

$$Z=R+JX \tag{1}$$

R represent the real part, X represents the imaginary part and J represents a phase of the voltage relative to the current. The unit for both R and X is Ω (Ohm). The value of the imaginary impedance X is a positive number in absolute value regardless of whether the voltage leads (+J) or lags (−J) the current. Alternatively, a plurality of PT test signals can be delivered to the electrodes and the complex impedance values are averaged.

Once the complex impedance value is determined, it is stored in the memory 44 by the treatment control module 54 to be used as a baseline to compare against later determined impedance values in order to determine an end of treatment. In one particularly preferred embodiment, the imaginary part X of the complex impedance Z is used as the baseline value because it represents the internal resistance of the cells which excludes the effects on the current flow of the cell membranes.

In some embodiments, the calculated imaginary impedance value may be adjusted down by a selected resistance value (or preselected percentage such as 5-10%) before being stored in the memory 44 as the baseline value in order to account for the fact that the resistance of the tissue cells may decrease by the selected resistance as the applied electroporation pulses increase the temperature of the tissue being ablated. For example, if the obtained impedance value is 150 Ohms (imaginary part of the impedance), a set value of 20 Ohms may be subtracted to account for the fact that the temperature rise may reduce the impedance by that amount. Thus, the value of 130 Ohms may be stored as the baseline value for comparison.

In step 86, based on the received parameters, the treatment control module 54 instructs the controller 71 in the pulse generator 10 to start an electroporation procedure. In step 88, under the control of the controller 71, the pulse generation circuit 72 starts delivering electroporation pulses through the electrodes 22 that have been placed in the patient.

In step 90, while the treatment procedure is in progress, the pulse control module 54 instructs the controller 71 in the pulse generator 10 to generate and apply an intra-treatment (IT) test signal through the electrodes 22. In one embodiment, the IT test signal is generated between electroporation pulses so as not to interfere with the treatment pulses and to receive a cleaner signal. The IT test signal is typically a direct current (DC) signal because only the real part of the impedance value is needed. Alternatively, the IT test signal can be the same type of signal as the PT test signal. In that case, the real part R is used as the comparison against the stored baseline value as will be explained in more detail below.

Preferably, the IT test signal has a voltage whose amplitude is insufficient to cause an electroporation of a majority of tissue cells in the target region, and more preferably is insufficient to cause electroporation of any tissue cells in the target region. Although the voltage of the IT test signal depends to a certain extent on the type of tissue cells to be ablated, it is generally less than 500 volts/cm and is preferably between 10 and 200 volts/cm. Similar to the PT test signal, the duration of the IT test signal can vary but should be sufficiently long (e.g., 10 to 100 microseconds for a DC test signal, 1-10 milliseconds for an AC test signal) to establish a stable impedance value. If needed, several IT test signals can be made to ensure that the impedance value is consistent.

The frequency of applying the IT test signals to obtain comparison values to compare against the baseline value can vary depending on the tissue type being treated and other treatment parameters. Typically, the IT test signal can be applied after every treatment electroporation pulse or after several electroporation pulses. In an alternative embodiment, the IT test signal can be applied after every train of pulses (e.g., after a train of 10 electroporation pulses).

While the IT test signal is being applied, the sensor 73 continuously senses the current values which are sent to the controller 71. The treatment control module 54 then determines an impedance from the measured current values along with the applied voltage. In a preferred embodiment, regardless of whether the IT test signal is an AC or DC signal, the treatment control module 54 determines the real part of the impedance in a known manner and stores it in the memory 44 as a comparison value for comparison against the stored baseline value.

In a preferred embodiment, a progress of the electroporation procedure is determined and displayed on the monitor 11 as the treatment procedure progresses. To do so, prior to the treatment procedure, a second PT test signal (e.g., DC test signal having 50 volts/cm) is applied and a DC resistance value (i.e., real resistance) is obtained. The difference between the baseline value and the DC resistance value from the second PT test signal is obtained and stored in the memory 44. Then, the progress of the treatment can be calculated by dividing a numerator value (comparison resistance value from step 90 less the baseline resistance value) by the difference value to obtain the percentage of ablation that still needs to be completed. As an example, assume that the baseline value and the DC resistance value are 150 Ohms and 600 Ohms, respectively. The difference value then is 450 Ohms. As IT test signals are applied, assume that the comparison resistance values are calculated to be 550, 300, 200 and 170. Then, the progress percentage are calculated as (550-150)/450, (300-150)/450, (200-150)/450, and (170-150)/450. Accordingly, the percentage of ablation that needs to be completed are displayed on the monitor 11 as 89%, 33%, 11% and 4%, respectively. When the number goes to 0%, then the treatment control module 54 determines that an end point of the treatment procedure has been reached. If percentage of completion is desired, of course, the numbers would be subtracted from 100%.

Similarly, the progress of the treatment can be determined from the current values. As an example, assume that the current value from the DC PT test signal is 50 V/600 Ohms=0.08 Amps and the target current value is 50 V/150 Ohms=0.33 Amps. Accordingly, current measurements of 0.1 Amps and 0.3 Amps from the IT test signals during the treatment would indicate the treatment progress of 8% ((0.1-0.08)/(0.33-0.08)) and 88% ((0.3-0.08)/(0.33-0.08)), respectively.

Figure 8:
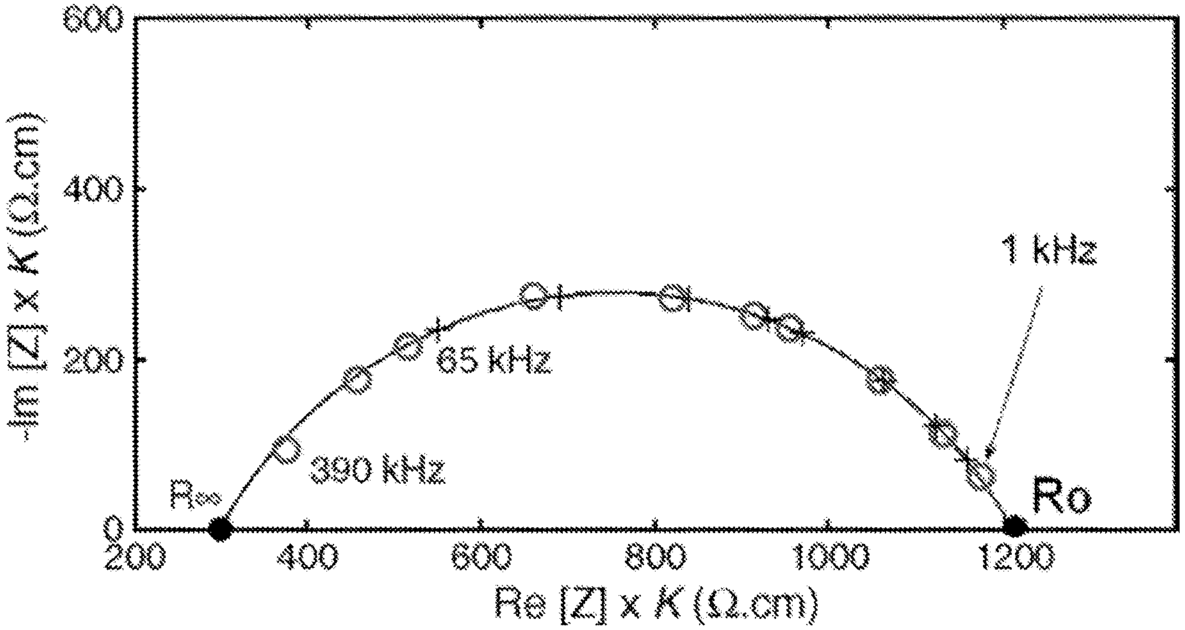
FIG. 8 is a graph of predicted impedance values across a frequency spectrum as predicted by a Cole model and a superimposed impedance values from a rat liver.

In an alternative to or in addition to applying a test signal at a single frequency, a plurality of test signals at different frequencies can be applied prior to and during the treatment procedure. FIG. 8 illustrates a graph of predicted impedance values across a frequency spectrum as predicted by a Cole model and superimposed impedance values from an actual rat liver prior to electroporation. As the electroporation pulses are applied, the circular shaped curve becomes narrower with real impedance values at lower frequencies approaching those of higher frequencies.

To monitor the progress and determine the progress percentage for display on the display 11 and to determine an end point of the treatment procedure, the reduction of the real part of the impedance values at various test signal frequencies can be monitored. As an example, an AC test signal at frequencies of 1 KHz, 10 KHz, 100 KHz, 1 MHz, 10 MHz, 100 MHz and 300 MHZ (both pre-treatment and intra-treatment) may be used. By experiment and model calculations, the real impedance values at the end of the treatment procedure at those frequencies can be obtained and stored in the memory 44. At step 84, the AC test signals can be applied sequentially in a frequency sweep prior to the treatment and corresponding impedance values (particularly the real part) are obtained and stored. As the electroporation pulses are delivered, the AC test signals at the same frequencies between electroporation pulses are applied and the real impedance values are obtained. They are then compared to the stored values in a similar manner as discussed above to obtain the progress percentage and to determine the end point of the treatment procedure. This method can be more robust than the others as confirmation of the progress level and end point are made at multiple frequencies.

In addition, the imaginary component from the test signals at the various frequencies can be monitored as well, which could serve as a surrogate for changes due to temperature rise. For example, if the imaginary component of the sweep increases by an average of 15% over the different frequencies (or at the peak value from the plot), the target final impedance values from the IT test signals can be adjusted by the 15% as well (i.e., shift down the final impedance value from 150 ohm to 150−150*0.15=127.5 ohm).

Alternatively, rather than applying test signals in step 90, the treatment control module 54 uses the electroporation pulses themselves (as applied in step 88) to measure the real impedance values based on the voltage applied and the current sensed by the sensor 73 as the electroporation pulses are being applied.

In step 94, the treatment control module 54 determines whether the impedance value (real part of the impedance value obtained in step 90) of the IT test signal has reached the baseline impedance value (imaginary part of the complex impedance obtained from step 84) of the PT test signal. Specifically, the module 54 determines whether the impedance value from step 90 is less than or equal to the baseline value from step 84. If the answer is NO, then the method under the control of the treatment control module 54 automatically goes back to step 88 where the electroporation pulses are applied again.

If the answer is YES, however, the treatment control module 54 executes a second comparison step (step 100) to make sure that the treatment has reached an end. In step 100, the module 54 determines whether the change of real impedance values from successive IT test signals is less than a preset threshold value. As discussed earlier, preferably, SMA or EMA values are used to remove signal-to-signal fluctuation. For example, the preset threshold value may be 25 Ohms, which may be preset or user-programmed or user-adjusted. The assumption is that when the real impedance value does not vary by much, e.g., less than 25 Ohms, between successive IT test signals, then the treatment has reached an end.

If the answer is NO, then the method goes back to step 88 where the electroporation pulses are applied again. If the answer is YES, however, the treatment control module 54 determines that the end of treatment has been reached. As a result, in step 102, the treatment control module 54 sets an End-of-Treatment flag.

In step 98, the module 54 terminates the treatment procedure. Alternatively, rather than terminating the procedure, the treatment control module 54 may provide an option to the user/physician to complete the programmed number of electroporation pulses. Of course, if there are multiple pairs of electrodes and treatment procedure for the target region represented by only one pair is completed, the method automatically goes to the next pair of electrodes and repeats the steps starting at step 84 or 88.

As a realistic example, assume that the baseline impedance value (imaginary part of the complex impedance obtained from step 84) is determined to be 150 Ohms. Since the AC signal effectively short circuits the cell membrane, the baseline imaginary impedance value generally represents the electrical resistance of the tissue cells without the effects of their membranes. At the beginning of the treatment, as the electroporation pulses are applied in step 88, the impedance (real part) of the IT test signal may be relatively high, e.g., 650 Ohms, because the cell membranes block the flow of electricity. However, as treatment progresses, the electroporation pulses start to puncture holes in the membranes and the electrically conductive fluid from inside the cells starts to flow out through the punctured holes. This results in a conductance increase and an impedance (real impedance) decrease. At some point during the delivery of treatment pulses, the real impedance reaches the baseline impedance value of 150 Ohm or the scaled targeted value (e.g., 130 Ohms) based on change in temperature factor. At that point, the treatment control module 54 determines that the end of treatment has been reached.

In an alternative embodiment, the comparison in step 94 is sufficient to determine that the end of treatment has been reached and step 100 is not executed. Conversely, in another alternative embodiment, the comparison in step 100 is sufficient to determine that the end of treatment has been reached and step 94 is not executed.

In yet another alternative embodiment, steps 94 and 100 are reversed such that the change of real impedance values from successive IT test signals need to fall below a preset threshold value before the comparison of whether the impedance value (real part of the impedance value obtained in step 90) of the IT test signal is less than or equal to the baseline impedance value (imaginary part of the complex impedance obtained from step 84) of the PT test signal occurs.

In another aspect of the present invention, IRE and other electroporation procedures would benefit greatly by utilizing the available tissue property data to gain insight into the response of the tissue relative to expectations (e.g., tissue response such as current and impedance from PT alternating current test signals and IT test signals) and adjust or control the electroporation protocol accordingly. By involving actual tissue response for the case and electrode pair at-hand, it should be possible to predict completeness and dimensions of ablation with higher reliability and tighter tolerances than that using a prescribed pulsing protocol alone.

In another aspect of the invention, the pulse metrics and their trends are incorporated with the user-input electrode separation distances in a system analyzer to predict lesion dimensions for the present electrode pulsing pair. A detailed discussion of predicting lesion dimensions is disclosed in PCT International Application Number PCT/US10/29243, filed Mar. 30, 2010 and entitled "System and Method for Estimating a Treatment Region for a Medical Treatment Device and for Interactively Planning a Treatment of a Patient", which is incorporated herein by reference.

Figure 7:
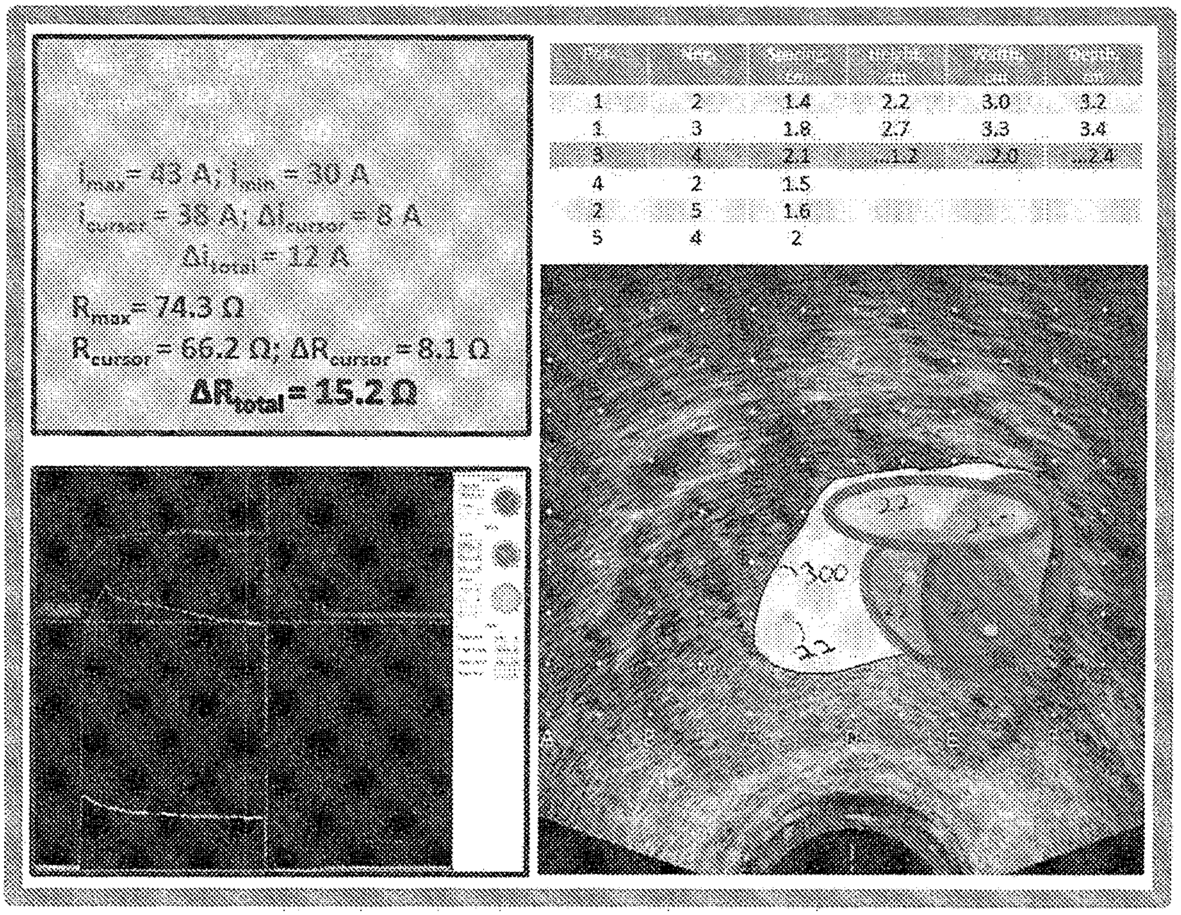
FIG. 7 is a screen shot of an electroporation treatment procedure in progress with real-time monitoring of the treatment progress.

As shown in FIG. 7, as the procedure progresses for the given electrode pair and the pulse metrics reflect growth in the lesion, the treatment control module 54 will update with the most current predictions of ablation dimensions, thus enabling the user to determine when the pair has attained satisfactory ablation dimensions and the electroporation protocol can progress onto the next electrode pair. The dimensions are given as tabulated data and also included on a graphical depiction of electrode locations, both of which are in the user interface screen.

The treatment control module 54 also records the accumulation of ablated areas for each electrode pair in the protocol, enabling the user to monitor their superimposition and ensure the overall ablation protocol addresses all targeted regions. As shown in FIG. 7, the lesion 300 to be ablated is shown with electrode 22 placements and the corresponding predicted ablation area for each pair of electrodes, which are superimposed on the actual imaged tissue area (e.g., ultrasound image) in real-time.

The treatment control module 54 is able to control the progress of the electroporation protocol by directing the therapeutic pulse generator. In essence, once a satisfactory ablation zone has been achieved for a given electrode pair, the control module 54 is able to rapidly move the pulses to the next electrode pair to continue the procedure. This includes detection of when the lesion is too small and the system can control the generator to deliver additional pulses or ones of greater magnitude (higher voltage, longer pulse length).

The treatment control module 54 interprets the pulse metric data in relation to the tissue type, electrode separation from the generator input, and previous pulse data. This information is integrated with previously calibrated information that correlates ablation dimensions with these metrics. The result of the integration is to predict the ablation dimensions for the given electrode pair. This dimension prediction is updated with every pulse as the pulse metrics continue to change through the procedure with the help of IT test signals. This information is sent to a graphical user interface of the treatment control module for display in the monitor 11.

The system 2 has a feedback screen, which is a graphical user interface that conveys all relevant information regarding the pulse analysis and ablation zone predictions. This includes the previous pulse waveforms of voltage, current, and resistance calculation (bottom left portion of FIG. 7). It also retrieves the relevant data from the pulse metrics stored in the memory 44 and conveys this information in a tabulated form for the user to see (top left portion). The ablation zone predictions are conveyed to the user for each electrode pair undergoing pulsing during the electroporation protocol, where the previous final zones are stored, and the active electrode pair has dimensions that will grow as pulsing and electroporated volume continues, as predicted by the pulse metrics (top right portion). Finally, an overlay of a medical image, such as ultrasound, CT, or MRI is displayed, where the user can trace the region of interest, and also displays the electrode array provided from the generator input (bottom right portion). The predicted ablation zones for each electrode pair previously performed (electrode pairs 1-2 and 1-3) are superimposed on this image, as well as the currently active electrode pulsing pair (electrodes 3-4), which will change in dimension based on the ablation zone predictions as the pulse metric data changes. The ablation zone predictions can be calculated based on the test signals (PT and IT signals) as the treatment progresses. For example, the calculations can be made based on adjustments to the Cassini oval equations as described in applicant's own PCT International Application Number PCT/US10/29243, filed Mar. 30, 2010 and entitled "System and Method for Estimating a Treatment Region for a Medical Treatment Device and for Interactively Planning a Treatment of a Patient", which is incorporated herein by reference.

In addition, the treatment control module 54 is used to guide the progression of the electroporation process based on data provided by the user and the sensor 73 data. The module controls the electroporation pulse generator 10 by altering the inputs to reflect the intentions of the user. This includes changing the pulse parameters to increase the ablation zone 300 if the pulse metrics indicate that the zone is too small as visually seen on the display 11 (see FIG. 7) and greater voltage, pulse length, or pulse number is necessary. In addition, the module 54 determines when the ablation zone for a given electrode pair has reached a satisfactory size for the demands of the user, and indicates to the generator 10 to move to the next electrode pair in the protocol sequence.

Among the many concepts encompassed by the present invention, mention may be made of several exemplary concepts relating to engineered tissues. For example, in creating engineered organs, the initial organ can be completely removed of cells using irreversible electroporation prior to reseeding (this is especially relevant for organs having at least one dimension that is less than 1 mm); the organ can be irreversibly electroporated in sections and reseeded to allow the human cells to infiltrate small sections at a time; the organ can be irreversibly electroporated in incremental slices introducing the cells in stages, so that no human viable cells are in contact with the viable animal cells they are replacing; the organ can be irreversibly electroporated entirely or in sections and the human cells can be injected into targeted locations in the organ; the entire organ can be irreversibly electroporated to kill the animal cells, then human cells can be replanted on top of the organ to infiltrate the scaffold and replace the other cells (as the animal cells die, the human cells will fill in and substitute, thereby creating a new organ.)

Having provided isolated engineered tissues and organs, it is possible to provide methods of using them. The invention contemplates use of the engineered tissues in both in vitro and in vivo settings. Thus, the invention provides for use of the engineered tissues for research purposes and for therapeutic or medical/veterinary purposes. In research settings, an enormous number of practical applications exist for the technology. One example of such applications is use of the engineered tissues in an ex vivo cancer model, such as one to test the effectiveness of various ablation techniques (including, for example, radiation treatment, chemotherapy treatment, or a combination) in a lab, thus avoiding use of ill patients to optimize a treatment method. For example, one can attach a recently removed liver (e.g., pig liver) to a bioreactor or scaffold and treat the liver to ablate tissue. Another example of an in vivo use is for tissue engineering.

The engineered tissues of the present invention have use in vivo. Among the various uses, mention can be made of methods of in vivo treatment of subjects (used interchangeably herein with "patients", and meant to encompass both human and animals). In general for certain embodiments, methods of treating subjects comprise implanting an engineered tissue according to the invention into or on the surface of a subject, where implanting of the tissue results in a detectable change in the subject. The detectable change can be any change that can be detected using the natural senses or using man-made devices. While any type of treatment is envisioned by the present invention (e.g., therapeutic treatment of a disease or disorder, cosmetic treatment of skin blemishes, etc.), in many embodiments, the treatment will be therapeutic treatment of a disease, disorder, or other affliction of a subject. As such, a detectable change may be detection of a change, preferably an improvement, in at least one clinical symptom of a disease or disorder affecting the subject. Exemplary in vivo therapeutic methods include regeneration of organs after treatment for a tumor, preparation of a surgical site for implantation of a medical device, skin grafting, and replacement of part or all of a tissue or organ, such as one damaged or destroyed by a disease or disorder (e.g., the liver). Exemplary organs or tissues include: heart, lung, liver, kidney, urinary bladder, brain, ear, eye, or skin. In view of the fact that a subject may be a human or animal, the present invention has both medical and veterinary applications.

The above disclosure is intended to be illustrative and not exhaustive. This description will suggest many modifications, variations, and alternatives may be made by ordinary skill in this art without departing from the scope of the invention. Those familiar with the art may recognize other equivalents to the specific embodiments described herein. Accordingly, the scope of the invention is not limited to the foregoing specification.

The invention claimed is:

1. A method of treating a tissue of a patient, the method comprising:

advancing at least one electrode to the tissue to be treated;

activating a generator to apply a plurality of electrical pulses, via the at least one electrode, to the tissue and inducing irreversible electroporation of cells of the tissue or the tissue;

continuing to apply the plurality of electrical pulses when a measured current value is within an acceptable threshold range; and stopping application of the plurality of electrical pulses when the measured current value is outside of the acceptable threshold range, wherein a controller is operatively coupled to the generator and configured to:

measure the current value associated with the plurality of electrical pulses;

apply an algorithm to evaluate the current value, wherein the applied algorithm includes comparing (1) a difference between an actual current value from an intra-treatment test signal and a current value from a pre-treatment test signal with (2) a difference between a target current value and the current value from the pre-treatment test signal; and determine whether the measured current value is within the acceptable threshold range.

2. The method of claim 1, wherein the plurality of electrical pulses have a frequency of 1 KHz, 10 KHz, 100 KHz, 1 MHz, 10 MHz, 100 MHz or 300 MHZ.

3. The method of claim 1, wherein the controller further:

generates one or more of the pre-treatment test signals to the tissue and one or more of the intra-treatment test signals to the tissue.

4. The method of claim 3, wherein the controller further:

determines an effect on the tissue by the plurality of electrical pulses based on a difference between one or more electrical properties of the tissue associated with application of one or more of the pre-treatment test signals to the tissue and one or more electrical properties of the tissue associated with application of one or more of the intra-treatment test signals to the tissue.

5. The method of claim 1, wherein the controller further:

measures the current value associated with the application of the electrical pulses via a current sensor.

6. The method of claim 1, wherein the tissue includes at least one of:

heart, lung, liver, kidney, urinary bladder, brain, ear, eye, skin, pancreas, and prostate.

7. A method comprising:

applying, via at least one electrode, a plurality of electrical treatment pulses to tissue of a patient and inducing irreversible electroporation of cells of the tissue or the tissue;

measuring a current value associated with the application of the plurality of electrical treatment pulses via a current sensor;

applying an algorithm to evaluate the current value; and determining whether the measured current value is within an acceptable threshold range;

wherein, when the current value is within the acceptable threshold range, continuing to apply the plurality of electrical treatment pulses;

wherein, when the current value is outside the acceptable threshold range, (1) adjusting at least one of a voltage and/or pulse length of the plurality of electrical treatment pulses or (2) stopping application of the plurality of electrical treatment pulses; and wherein the applied algorithm includes comparing (1) a difference between an actual current value from an intra-treatment test signal and a current value from a pre-treatment test signal with (2) a difference between a target current value and the current value from the pre- treatment test signal.

8. The method of claim 7, further comprising:

based on the comparing, determining a completeness of progress of the irreversible electroporation of cells of the tissue or the tissue.

* * * * *